United States Patent
Gomurashvili et al.

(10) Patent No.: US 7,649,022 B2
(45) Date of Patent: Jan. 19, 2010

(54) BIOABSORBABLE ELASTOMERIC POLYMER NETWORKS, CROSS-LINKERS AND METHODS OF USE

(75) Inventors: Zaza D. Gomurashvili, La Jolla, CA (US); Ramaz Katsarava, Tbilisi (GE); Giorgi Chumburdze, Tbilisi (GE); Nino Mumladze, Tbilisi (GE); David Tugushi, Tbilisi (GE)

(73) Assignee: MediVas, LLC, San Diego, CA (US)

( * ) Notice: Subject to any disclaimer, the term of this patent is extended or adjusted under 35 U.S.C. 154(b) by 99 days.

(21) Appl. No.: 12/058,613

(22) Filed: Mar. 28, 2008

(65) Prior Publication Data
US 2009/0253809 A1 Oct. 8, 2009

Related U.S. Application Data

(60) Provisional application No. 60/920,962, filed on Mar. 30, 2007.

(51) Int. Cl.
*A61K 47/00* (2006.01)
*A61K 47/30* (2006.01)
*A61F 13/00* (2006.01)

(52) U.S. Cl. ............... 514/772; 514/772.3; 424/442
(58) Field of Classification Search ........... 424/422; 514/772, 772.3
See application file for complete search history.

(56) References Cited

U.S. PATENT DOCUMENTS

| | | | |
|---|---|---|---|
| 4,221,787 A | 9/1980 | Bodor et al. | 514/176 |
| 5,554,692 A | 9/1996 | Ross | 525/124 |
| 5,849,841 A | 12/1998 | Muhlebach et al. | 525/59 |
| 5,852,155 A | 12/1998 | Bussink et al. | 528/170 |
| 5,972,027 A | 10/1999 | Johnson | 623/1.42 |
| 6,299,597 B1 | 10/2001 | Buscemi et al. | 604/101.03 |
| 2004/0110285 A1 | 6/2004 | Lendlein et al. | 435/366 |
| 2005/0216074 A1 | 9/2005 | Sahatjian et al. | 623/1.11 |
| 2006/0036311 A1 | 2/2006 | Nakayama et al. | 623/1.15 |
| 2006/0177416 A1 | 8/2006 | Turnell et al. | 424/78.27 |
| 2007/0071790 A1 | 3/2007 | Ameer et al. | 424/423 |
| 2007/0141100 A1 | 6/2007 | Sung et al. | 424/423 |

FOREIGN PATENT DOCUMENTS

| | | |
|---|---|---|
| WO | WO 94/04642 A2 | 3/1994 |
| WO | WO 97/30104 A1 | 8/1997 |
| WO | WO 98/32398 A1 | 7/1998 |

*Primary Examiner*—Raymond J Henley, III
(74) *Attorney, Agent, or Firm*—DLA Piper LLP (US)

(57) ABSTRACT

The invention provides elastomeric polymer networks and semi-interpenetrating networks in which a linear PEA, PEUR or PEU polymer is crosslinked by ester or alpha-amino-acid containing cross-linkers that polymerize upon exposure to active species. Bioabsorbable elastomeric internal fixation devices fabricated using such polymer networks and semi-interpenetrating networks are useful for in vivo implant and delivery of a variety of different types of molecules in a time release fashion. Alpha-amino-acid containing ester amide cross-linkers are also provided by the invention.

24 Claims, 8 Drawing Sheets

BIOABSORBABLE ELASTOMERIC POLYMER NETWORKS, CROSS-LINKERS AND METHODS OF USE

RELATED APPLICATIONS

This application claims priority under 35 U.S.C. §119(e) of U.S. Provisional applications, Ser. No. 60/920,962, filed Mar. 30, 2007, which is hereby incorporated by reference in its entirety.

FIELD OF THE INVENTION

The invention relates, in general, to drug delivery systems and, in particular, to polymer compositions that can be used to fabricate internal fixation devices for in vivo implant and for delivery of a variety of different types of molecules in a time release fashion.

BACKGROUND INFORMATION

Biodegradable polymers are becoming widely used in various fields of biotechnology and bioengineering, as implants for tissue engineering, surgical devices and for drug delivery. For example, regular AA-BB-type bio-analogous poly(ester amides) (PEAs), poly(ester urethanes) (PEURs), and poly(ester ureas) (PEUs), which consist of nontoxic building blocks, such as hydrophobic α-amino acids, aliphatic diols and di-carboxylic acids. These bio-analogous polymers have been proven to be important materials for biomedical applications because of their excellent blood and tissue compatibility (K. DeFife et al. *Transcatheter Cardiovascular Therapeutics—TCT2004 Conference. Poster presentation.* Washington D.C. 2004; J. Da, Poster presentation, ACS Fall National Meeting, San Francisco, 2006) and biologic degradation profiles (G. Tsitlanadze, et al. *J. Biomater. Sci. Polymer Edn.* (2004). 15:1-24). Controlled enzymatic degradation and low nonspecific degradation rates of PEAs make them attractive for drug delivery applications.

Because many biomedical devices are implanted in a bodily environment that undergoes dynamic stress, the implants must be sufficiently elastic to undergo and recover from deformation without subjecting the host's surrounding tissue to irritation and without mechanical breakdown of the polymer. Ideally such implants would have properties resembling those of the extracellular matrix, a soft, tough and elastomeric proteinaceous network that provides mechanical stability and structural integrity to tissues and organs. Such a polymer network would allow ready recovery from substantial deformations.

Various classes of biodegradable polymer elastomers have been disclosed: Elastin-like peptide elastomers are based on protein polymers and are produced recombinantly. Polyhydroxyalkanoates, such as poly-4-hydroxybutyrate, have also been used as elastomeric polymers. Hydrogels have been proposed based on such various compounds as alginate, vegetal proteins crosslinked with synthetic water soluble polymer (PEG), and cross-linked hyularonic acid. Recently a covalently cross-linked and hydrogen bonded three-dimensional polymer network in which at least one monomer is trifunctional has been described for use in polymer implants (Y Wang et al., *Nat. Biotech* (2002) 20:602-606).

Heretofore interpenetrating networks have found many applications as automotive parts (tires, belts, and bumpers), hoses, cables, gaskets, damping compounds, ion-exchange resins, optical fibers, medical gear, artificial teeth, and dental fillings, In addition, U.S. Pat. No. 5,837,752 describes a polymer composition that forms a semi-interpenetrating network made from a linear biodegradable hydrophobic or nonbiodegradable hydrophilic polymer and cross-linkers that include a degradable linkage, such as an anhydride linkage.

Despite such progress in the art, there is need for new and better polymer blends, such as those that can form non-biodegradable or biodegradable interpenetrating networks. In particular there is a need for polymer compositions suitable for forming elastomeric implantable devices of various types, including those used in tissue, tooth, and bone replacement.

SUMMARY OF THE INVENTION

The present invention is based on the discovery that an elastomeric polymer network, and in particular a semi-interpenetrating network, can be formed utilizing linear polymers, preferably bioabsorbable α-amino acid-based linear polymers, such as a poly(ester amide) (PEA), poly(ester urethane) (PEUR), or poly(ester urea) (PEU), and a variety of di- and poly-functional cross-linkers that contain one or more hydrolytically degradable functional groups and that polymerize upon exposure to an active species. The cross-linking provides increased elasticity to the composition by imparting a plasticizing effect. After cross-linkers are polymerized, the composition also possesses increased toughness.

Accordingly in one embodiment the invention provides compositions containing at least one linear polymer and a di- or poly-functional cross-linker that contains at least one hydrolyzable functional group and two or more functional groups that polymerize upon exposure to an active species.

A BRIEF DESCRIPTION OF THE FIGURES

A DETAILED DESCRIPTION OF THE INVENTION

Figure 1:
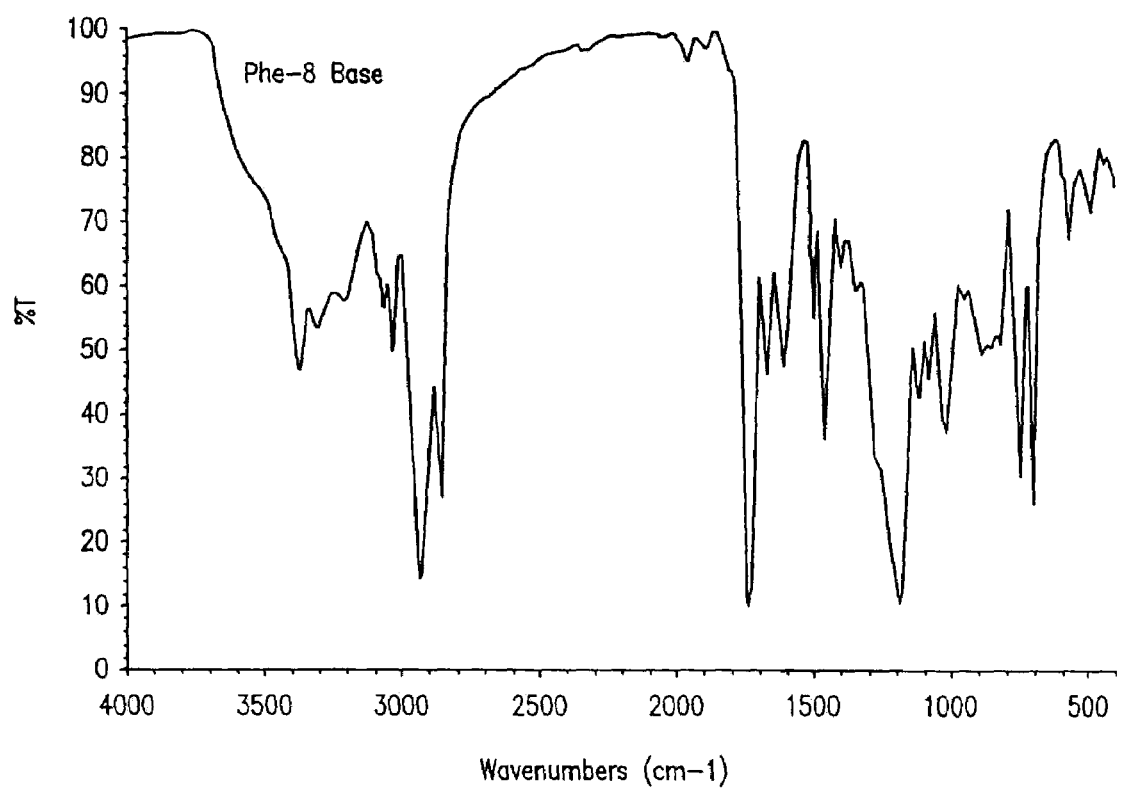
FIG. 1 is a trace of an FTIR spectrum of di-amino-diester free base (Phe-8,b) prepared according to Scheme 4 wherein $R^3=CH_2(C_6H_5)$; and $R^4=(CH_2)_8$.

The present invention is based on the discovery that elastomeric non-biodegradable or biodegradable polymeric networks, and in particular semi-interpenetrating networks, can be formed using di- and poly-functional cross-linkers and linear polymer(s). The cross-linkers used in the invention compositions contain one or more hydrolyzable functional groups and polymerize upon exposure to an active species. Polymerization of the cross-linkers provides increased elasticity to the composition by imparting a plasticizing effect. After the cross-linkers are polymerized, the elastomeric composition also possesses increased toughness.

Due to these properties, in certain embodiments, the invention composition can be introduced in vivo in a liquid state (i.e., prior to cross-linking), for example by injection, and cross-linked in place to create a polymer with a combination of elasticity and toughness suitable for use in an implantable fixation device. Alternatively the composition can be cross-linked (i.e., polymerized) ex vivo and implanted. When polymerized ex vivo, the composition readily can be shaped into various devices. For example, the polymerized composition can be fashioned into expandable bioabsorbable stents for stabilization and repair of diseased vasculature, or into internal fixation devices, such as surgical pins, screws, and hollow tubes, which can be used, for example, to repair broken bones and repair damaged tendons and cartilage. Therefore, a beneficial end use of the invention elastomeric composition is in the form of an implantable biodegradable internal fixation device.

The invention compositions comprise at least two components. The first component is at least one linear polymer. The linear polymer can be either a homopolymer or a copolymer and can be biodegradable or non-biodegradable. The preferred linear polymers contain at least one amino acid and a non-amino acid moiety per repeat unit. The second component of the invention composition is at least one di- or poly-functional cross-linker containing one or more hydrolyzable groups, such as an ester group, and at least two polymerizable groups, such that the at least one cross-linker in the composition polymerizes upon exposure to an active species. Polymerizable groups can undergo free radical, cationic or cycloaddition crosslinking. Upon polymerization of the crosslinker, a biodegradable semi-interpenetrating network of polymers is formed. After these components are mixed, and the crosslinker has been crosslinked, a tough polymer network, or semi-interpenetrating network, is formed.

The invention compositions can optionally further include a reactive diluent, which can be used to modify the viscosity of the composition and/or to adjust the cure rate, and one or more non reactive viscosity modifiers.

The invention compositions can further include various excipients, fillers, inorganic particles (such as hydroxyapatite, calcium phosphate, dissolvable salts), therapeutic and diagnostic agents; the compositions optionally can further or alternatively contain a dispersant, a photo-initiator and/or a photosensitizer (which can improve quantum yield of photoinitiation). A variety of factors determine the photochemical reactivity of the composition. For example, such factors as the reaction temperature, intensity of photo irradiation, presence or absence of oxygen, and the type and concentration of initiator can determine the photochemical reactivity of the composition. These factors influence the kinetic parameters, such as the rate constants of the initiation, propagation and termination of the photochemical reaction.

As used herein, the term "interpenetrating network" means a polymer blend formed by two or more mixed, cross-linked polymers. When one of the polymers in the blend is completely linear, such composition is called a "semi-interpenetrating network" herein.

As used herein the term "bioactive agent" means a chemical agent or molecule that affects or can be used to diagnose a biological process and thus the term includes reference to therapeutic, palliative and diagnostic agents. The bioactive agents may be contained within polymer conjugates or otherwise dispersed in the polymers of the composition, as described below. Such bioactive agents may include, without limitation, diagnostic agents used in a variety of imaging techniques, as well as drugs, peptides, proteins, DNA, cDNA, RNA, sugars, lipids and whole cells. One or more such bioactive agents may be included in the invention compositions.

As used herein, the term "dispersed" is used to refer to the bioactive agents and means that the bioactive agent is dispersed, mixed, or dissolved into, homogenized with, and/or covalently bound to a linear polymer, for example attached to a functional group in the linear polymer of the composition or to the surface of an article of manufacture, such as an internal fixation device, made using the polymers described herein.

In one embodiment, the linear polymer contains at least one amino acid and a non-amino acid moiety per repeat unit. As used herein, the terms "amino acid" and "α-amino acid" mean a chemical compound containing an amino group, a carboxyl group and a pendent R group, such as the $R^3$ groups defined herein. As used herein, the term "biological α-amino acid" means the amino acid(s) used in synthesis are selected from phenylalanine, leucine, glycine, alanine, valine, isoleucine, methionine, or a mixture thereof.

The term "non-amino acid moiety" as used herein includes various chemical moieties, but specifically excludes amino acids, amino acid derivatives and peptidomimetics thereof as described herein. In addition, the term "at least one amino acid" is not contemplated to include poly(amino acid) segments, such as naturally occurring polypeptides, unless specifically described as such. In one embodiment, the non-amino acid is placed between two adjacent α-amino acids in the repeat unit. The polymers may comprise at least two different amino acids per repeat unit and a single polymer molecule may contain multiple different α-amino acids in the polymer molecule, depending upon the size of the molecule. In other embodiments, the non-amino acid moiety is hydrophobic or hydrophilic.

The linear polymer can constitute from about 10% to about 90% by weight of the composition, for example from about 30% to about 70% by weight of the composition. The crosslinked polymer can constitute from about 30% to about 70% by weight of the semi-interpenetrating network composition, for example, from about 40% to about 60% by weight of the composition, with the balance being excipients, bioactive or diagnostic agents, and other components as described herein. In this embodiment, the composition forms a semi-interpenetrating polymer network when the above-described weight percents of the components are mixed, and the crosslinker is crosslinked.

As used herein, the term "semi-interpenetrating network" means a combination of two or more polymers in network form, at least one of which is polymerized and/or crosslinked in the immediate presence of the other(s). Formation of the semi-interpenetrating network influences the molecular interpenetration of immiscible polymer networks to avoid phase separation. In the embodiment of the invention wherein the linear polymer is itself polymerized, the composition forms a fully-interpenetrating network. Semi- and fully-interpenetrating networks, therefore, are part of the broad class of polymeric compositions described herein.

The invention compositions can have a viscosity before crosslinking anywhere between a viscous liquid suitable for injection into a body to a moldable, paste-like putty. The viscosity can be adjusted by adding reactive diluents and/or by adding appropriate solvents. When crosslinked, however, the compositions are semi- or fully-interpenetrating networks with mechanical properties capable of supporting bone growth and repair.

Upon being polymerized, the cross-linker increases elasticity of the composition by imparting a plasticizing effect thereto. Therefore, the composition can be introduced into the body as a viscous liquid, for example by injection or plastic implant, and then be increased in rigidity and toughness by crosslinking the cross-linker of the composition in vivo. In another embodiment, the linear polymer is itself auto-crosslinking without exposure to active species, for example by photoinduced cycloaddition.

The invention compositions can be introduced (injected) into a patient and polymerized in situ or can be polymerized ex vivo and implanted. In certain embodiments, when polymerized ex vivo, the composition can be shaped into various articles, such as bioabsorbable stents for vascular repair, or biodegradable surgical pins, screws, plates and hollow tubes, which can be used in repair of broken bones and in various additional orthopaedic applications.

Although initially ductile and shape-resistant prior to cross-linking or polymerizing, when polymerized, the invention compositions and objects made thereof possess a combination of elasticity and toughness. For example, a photocurable polymeric vascular stent made using the invention composition is initially ductile (plasto-elastic) so that it can be expanded with the aid of balloon catheter for implant, yet retracts to a desired size upon removal of the balloon catheter. The stent then becomes hardened upon exposure to photoradiation or another energy source for creation of active species from initiators included in the composition to polymerize the cross-linker in the composition.

Although an initiator may be included in the invention composition, photochemical or thermal reactivity of the invention composition depends on the functionality and chemical structure of the cross-linker, its viscosity, and reaction conditions. Functionality of the cross-linker is provided, for example, by the non-amino acid moiety used in synthesis, for example, whether a vinyl, acryloyl, methacryloyl, cinnamoyl functionality is present therein, as is described more fully below.

Linear, Hydrophobic Biodegradable Polymers

Linear polymers are defined as homopolymers or block copolymers that are not crosslinked. Biodegradable linear polymers are well known to those of skill in the art. "Biodegradable" as used to describe the linear polymers are those that have a half life under physiological conditions of between about two hours and one year, preferably between about two months and six months, more preferably, between about two weeks and four months.

Examples of suitable biodegradable polymers include polyanhydrides, polyorthoesters, polyhydroxy acids, polydioxanones, polycarbonates, and polyaminocarbonates. Suitable hydrophilic polymers include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses, such as hydroxyethyl cellulose and methylhydroxypropyl cellulose, and natural polymers such as polypeptides, polysaccharides or carbohydrates such as Ficoll™ polysucrose, hyaluronic acid, dextran, heparan sulfate, chondroitin sulfate, heparin, or alginate, and proteins such as gelatin, collagen, albumin, or ovalbumin, as well as copolymers and blends thereof. As used herein, "celluloses" includes cellulose and derivatives of the types described above; "dextran" includes dextran and similar derivatives thereof.

Another type of linear biodegradable polymer comprises at least one α-amino acid conjugated to at least one non-amino acid moiety per repeat unit. The preferred biodegradable linear polymer for use in the invention compositions and methods of use comprises at least one of the following polymers: a PEA having a chemical formula described by general structural formula (I):

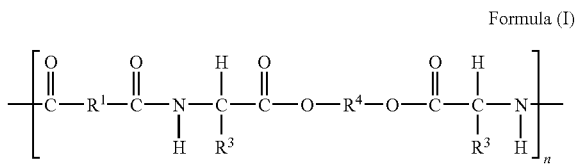

Formula (I)

wherein, n is about 10 to about 150; each $R^1$ is independently selected from the group consisting of $(C_2-C_{20})$ alkylene, $(C_2-C_{20})$ alkenylene, $(C_2-C_{12})$ epoxy-alkylene, residues of α,ω-bis(o,m, or p-carboxy phenoxy)-$(C_1-C_8)$ alkane, 3,3'-(alkenedioyldioxy) dicinnamic acid, 4,4'-(alkanedioyldioxy) dicinnamic acid, and combinations thereof; the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl, $(CH_2)_2SCH_3$, and combination thereof, and $R^4$ in each n monomer is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of general formula (II), and combinations thereof;

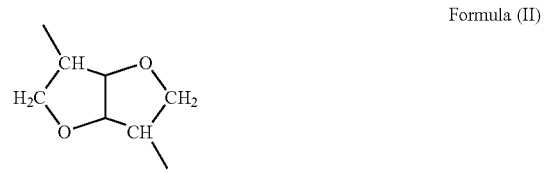

Formula (II)

or a PEA having a chemical structure described by general structural formula (III),

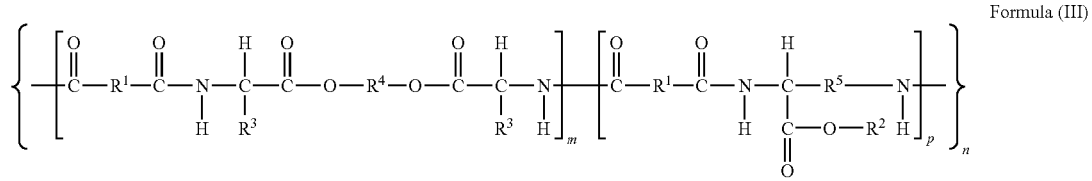

Formula (III)

wherein m is about 0.1 to about 0.9; p is about 0.9 to about 0.1, n is about 10 to about 150, each $R^1$ is independently selected from the group consisting of $(C_2-C_{20})$ alkylene, $(C_2-C_{20})$ alkenylene, $(C_2-C_{12})$ epoxy-alkylene, residues of α,ω-bis(o, m, or p-carboxy phenoxy)-$(C_1-C_8)$ alkane, 3,3'-(alkenedioyldioxy) dicinnamic acid, 4,4'-(alkanedioyldioxy) dicinnamic acid, and combinations thereof, $R^2$ is independently selected from the group consisting of hydrogen, $(C_6-C_{10})$ aryl $(C_1-C_6)$ alkyl, a protecting group, and combinations thereof; each $R^3$ is independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl $(CH_2)_2SCH_3$, and combinations thereof; and each $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of general formula (II), and combinations thereof; and $R^5$ is independently $(C_2-C_{20})$ alkyl or $(C_2-C_{20})$ alkenyl;

a PEUR having a chemical formula described by structural formula (IV),

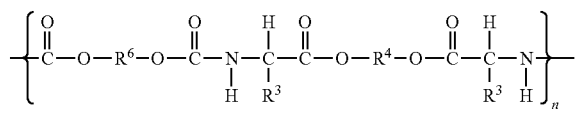

Formula (IV)

wherein n ranges from about 5 to about 150; wherein the $R^3$s in an individual n monomer are independently selected from the group consisting of hydrogen, $(C_1-C_6)$ alkyl, $(C_2-C_6)$ alkenyl, $(C_6-C_{10})$ aryl$(C_1-C_6)$ alkyl, $(CH_2)_2SCH_3$, and combinations thereof; $R^4$ and $R^6$ are independently selected from the group consisting of $(C_2-C_{20})$ alkylene, $(C_2-C_{20})$ alkenylene, $(C_2-C_{20})$ alkyloxy $(C_2-C_{20})$ alkylene, bicyclic-fragments of 1,4:3,6-dianhydrohexitols of structural formula (II), and combinations thereof;

or a PEUR having a chemical structure described by general structural formula (V),

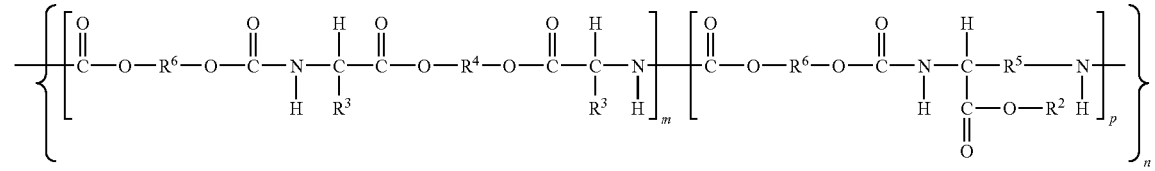

Formula (V)

wherein n ranges from about 5 to about 150, m ranges about 0.1 to about 0.9: p ranges from about 0.9 to about 0.1; $R^2$ is independently selected from the group consisting of hydrogen, $(C_1-C_{12})$ alkyl, $(C_2-C_8)$ alkyloxy, $(C_2-C_{20})$ alkyl $(C_6-C_{10})$ aryl, and a protecting group; the $R^3$s within an individual m monomer are independently selected from the group consisting of hydrogen, $(C_1-C_6)$ alkyl, $(C_2-C_6)$ alkenyl, $(C_6-C_{10})$ aryl $(C_1-C_6)$ alkyl, and $(CH_2)_2SCH_3$; $R^4$ and $R^6$ are independently selected from the group consisting of $(C_2-C_{20})$ alkylene, $(C_2-C_{20})$ alkenylene, $(C_2-C_{20})$ alkyloxy $(C_2-C_{20})$ alkylene, bicyclic-fragments of 1,4:3,6-dianhydrohexitols of structural formula (II), and combinations thereof, and $R^5$ is independently selected from the group consisting of $(C_1-C_{20})$ alkyl and $(C_2-C_{20})$ alkenyl, for example, $(C_3-C_6)$ alkyl or $(C_3-C_6)$ alkenyl, preferably —$(CH_2)_4$—;

or a PEU having a chemical formula described by structural formula (VI),

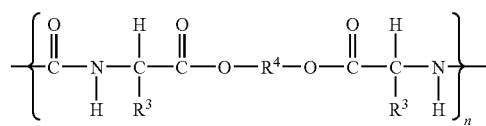

Formula (VI)

wherein n is about 10 to about 150; the $R^3$s within an individual n monomer are independently selected from the group consisting of hydrogen, $(C_1-C_6)$ alkyl, $(C_2-C_6)$ alkenyl, $(C_6-C_{10})$ aryl $(C_1-C_6)$ alkyl, and $(CH_2)_2SCH_3$; $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of a 1,4:3,6-dianhydrohexitol of structural formula (II) and combinations thereof;

or a PEU having a chemical formula described by structural formula (VII),

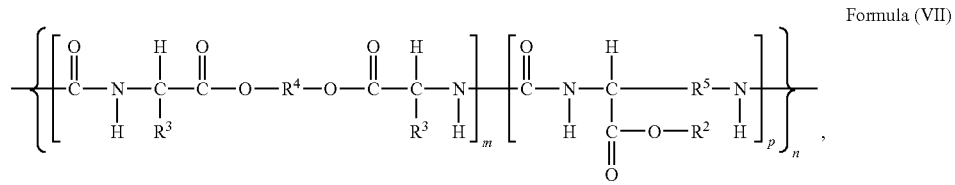

Formula (VII)

wherein m is about 0.1 to about 1.0; p is about 0.9 to about 0.1; n is about 10 to about 150; each $R^2$ is independently hydrogen, $(C_1-C_{12})$ alkyl, $(C_2-C_8)$ alkyloxy $(C_2-C_{20})$ alkyl, $(C_6-C_{10})$ aryl or a protecting group; and the $R^3$s within an individual m monomer are independently selected from hydrogen, $(C_1-C_6)$ alkyl, $(C_2-C_6)$ alkenyl, $(C_6-C_{10})$ aryl $(C_1-C_6)$ alkyl and $(CH_2)_2SCH_3$; $R^4$ is independently selected from $(C_2-C_{20})$ alkylene, $(C_2-C_{20})$ alkenylene, $(C_2-C_8)$ alkyloxy $(C_2-C_{20})$ alkylene; bicyclic-fragments of a 1,4:3,6-dianhydrohexitol of structural formula (II), and combinations thereof, and $R^5$ is independently selected from the group consisting of $(C_1-C_{20})$ alkyl and $(C_2-C_{20})$ alkenyl, for example, $(C_3-C_6)$ alkyl or $(C_3-C_6)$ alkenyl, preferably —$(CH_2)_4$—.

For example in one embodiment of the PEA polymer, at least one $R^1$ is a residue of α,ω-bis(4-carboxyphenoxy) $(C_1-C_8)$ alkane or 4,4'-(alkanedioyldioxy) dicinnamic acid and $R^4$ is a bicyclic-fragment of a 1,4:3,6-dianhydrohexitol of general formula (II). In another alternative, $R^1$ in the PEA polymer is either a residue of α,ω-bis(4-carboxyphenoxy) $(C_1-C_8)$ alkane, or a residue of 4,4'-(alkanedioyldioxy) dicinnamic acid, or a combination thereof. In yet another alternative in the PEA polymer, $R^1$ is a residue α,ω-bis(4-carboxyphenoxy) $(C_1-C_8)$ alkane, such as 1,3-bis(4-carboxyphenoxy)propane (CPP), or 4,4'-(adipoyldioxy) dicinnamic acid, and $R^4$ is a bicyclic-fragment of a 1,4:3,6-dianhydrohexitol of general formula (II), such as 1,4:3,6-dianhydrosorbitol (DAS).

In one alternative in the PEUR polymer, at least one of $R^4$ or $R^6$ is a bicyclic fragment of 1,4:3,6-dianhydrohexitol, such as 1,4:3,6-dianhydrosorbitol (DAS).

In one alternative in the PEU polymer, at least one $R^4$ is a bicyclic fragment of a 1,4:3,6-dianhydrohexitol, such as DAS. In yet another alternative in the PEU polymer, at least one $R^4$ is a bicyclic fragment of a 1,4:3,6-dianhydrohexitol, such as DAS.

In alternative embodiments of the PEA, PEUR and PEU polymers of Formulas II, V and VII, respectively, $R^5$ is preferably, $(C_3-C_6)$ alkyl or $(C_3-C_6)$ alkenyl, and most preferably —$(CH_2)_4$—.

Suitable protecting groups for use in practice of the invention include t-butyl and others as are known in the art. Suitable bicyclic-fragments of 1,4:3,6-dianhydrohexitols can be derived from sugar alcohols, such as D-glucitol, D-mannitol, and L-iditol. For example, 1,4:3,6-dianhydrosorbitol (isosorbide, DAS) is particularly suited for use as a bicyclic-fragment of 1,4:3,6-dianhydrohexitol.

The term, "biodegradable" as used herein to describe the PEA, PEUR and PEU linear polymers used in the invention compositions means the polymer is capable of being broken down into innocuous and bioactive products in the normal functioning of the body. In one embodiment, the entire composition is biodegradable. These biodegradable PEA, PEUR and PEU polymers have hydrolyzable ester and enzymatically cleavable amide linkages that provide the biodegradability, and are typically chain terminated predominantly with amino groups. Optionally, these amino termini can be acetylated or otherwise capped by conjugation to any other acid-containing, biocompatible molecule, to include without restriction organic acids, bioinactive biologics and bioactive compounds such as adjuvant molecules.

Many of the PEA, PEUR and PEU polymers described herein by structural formulas (I and III-VII), have built-in functional groups on side chains, and these built-in functional groups can react with other chemicals and lead to the incorporation of additional functional groups to expand the functionality of the polymers further. Therefore, such polymers used in the invention methods are ready for reaction with other chemicals having a hydrophilic structure to increase water solubility and/or with bioactive agents and covering molecules, without the necessity of prior modification.

In addition, the PEA, PEUR and PEU linear polymers used in the invention compositions display minimal hydrolytic degradation when tested in a saline (PBS) medium, but in an enzymatic solution, such as chymotrypsin or CT, display a uniform erosive behavior.

In one alternative, the $R^3$s in at least one n monomer of the polymers of Formulas (I and III-VII) are $CH_2Ph$ and the α-amino acid used in synthesis is L-phenylalanine. In alternatives wherein the $R^3$s within a monomer are —$CH_2$—H $(CH_3)_2$, the polymer contains the α-amino acid, leucine. By varying the $R^3$s, other α-amino acids can also be used, e.g., glycine (when the $R^3$s are —H), alanine (when the $R^3$s are —$CH_3$), valine (when the $R^3$s are —$CH(CH_3)_2$), isoleucine (when the $R^3$s are —$CH(CH_3)$—$CH_2$—$CH_3$), phenylalanine (when the $R^3$s are —$CH_2$—$C_6H_5$); lysine (when the $R^3$s are —$(CH_2)_4$—$NH_2$); or methionine (when the $R^3$s are $(CH_2)_2$ $SCH_3$).

In yet a further embodiment wherein the polymer comprises a PEA, PEUR or PEU of formula I or III-VII, in at least one monomer the $R^3$s further can be —$(CH_2)_3$— wherein the $R^3$s cyclize to form the chemical structure described by structural formula (VIII):

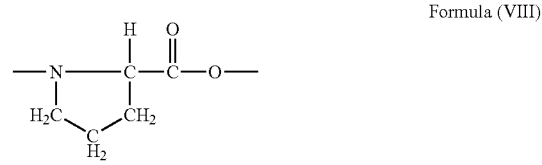

Formula (VIII)

When the $R^3$s are —$(CH_2)_3$—, an α-imino acid analogous to pyrrolidine-2-carboxylic acid (proline) is used.

The PEAs, PEURs and PEUs described by formulas (I and III-VII) are biodegradable polymers that biodegrade substantially by enzymatic action so as to release a dispersed bioactive agent over time. Due to structural properties of these polymers, when used in the invention methods, the compositions so formed provide for stable loading of the bioactive agent while preserving the three dimensional structure thereof and, hence, the bioactivity.

As used herein, "biodegradable" as used to describe the PEA, PEUR and PEU linear polymers in the invention compositions described by formulas (I and III-VII) means the polymer is capable of being broken down into innocuous products in the normal functioning of the body. In one embodiment, the entire composition is biodegradable. These biodegradable polymers have hydrolyzable ester linkages that provide the biodegradability, and are typically chain terminated, predominantly with amino groups.

As used herein, the terms "amino acid" and "α-amino acid" mean a chemical compound containing an amino group, a carboxyl group and a pendent R group, such as the $R^3$ groups defined herein. As used herein, the term "biological α-amino acid" means the amino acid(s) used in synthesis are selected from phenylalanine, leucine, glycine, alanine, valine, isoleucine, methionine, proline, or a mixture thereof. The term "non-amino acid moiety" as used herein includes various chemical moieties, but specifically excludes amino acid derivatives and peptidomimetics as described herein. In addition, the polymers containing at least one amino acid are not contemplated to include poly(amino acid) segments, such as naturally occurring polypeptides, unless specifically described as such. In one embodiment, the non-amino acid is placed between two adjacent α-amino acids in the repeat unit.

In the biodegradable PEA, PEUR and PEU polymers useful in practicing the invention, multiple different α-amino acids can be employed in a single polymer molecule. These polymers may comprise at least two different amino acids per repeat unit and a single polymer molecule may contain multiple different α-amino acids in the polymer molecule, depending upon the size of the molecule. In one alternative, at least one of the α-amino acids used in fabrication of the invention polymers is a biological α-amino acid.

The term "aryl" is used with reference to structural formulae herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulae herein to mean a divalent branched or unbranched hydrocarbon chain containing at least one unsaturated bond in the main chain or in a side chain.

In addition, the PEA, PEUR and PEU polymers used in the invention compositions biodegrade by enzymatic action at the surface, displaying a uniform erosive behavior, but display minimal hydrolytic degradation when tested in a saline (PBS) medium. Therefore, articles of manufacture made using compositions containing such polymers as the linear polymer, when implanted in vivo, may release a dispersed bioactive agent to the subject at a controlled release rate, which is specific and constant over a prolonged period.

Linear, Hydrophilic Non-Biodegradable Polymers

Linear, hydrophilic polymers are well known to those of skill in the art. Non-biodegradable polymers are those that have a half life longer than approximately one year under physiological conditions. Examples of suitable hydrophilic non-biodegradable polymers include poly(ethylene glycol), poly(ethylene oxide), partially or fully hydrolyzed poly(vinyl alcohol), poly(ethylene oxide)-co-poly(propylene oxide) block copolymers (poloxamers and meroxapols) and poloxamines. Preferred non-biodegradable polymers are poly(ethylene glycol), poloxamines, poloxamers and meroxapols.

Although in certain embodiments the polymers can be biodegradable, in some cases low molecular weight polymers are required to allow excretion. The maximum molecular weight to allow excretion in human beings (or other species in which use is intended) will vary with polymer type, but will often be about 20,000 Da or below.

The Cross-Linkers

A second component of the invention compositions is at least one bi- or poly-functional cross-linker selected from ester type cross-linkers (ESCs), ester-amide type cross-linkers (EACs), water soluble ester type cross-linkers (WESCs), and water soluble ester-amide type cross-linkers (WEACs). The terms "functionality" and "functional", as used to describe these cross-linkers, means the number of reactive functionalities (double bonds or primary amine groups) per molecule. For example, a di-functional cross-linker contains two double bonds. Functionality can also be expressed as the number of double bonds per kilogram of monomer. The cross-linkers described herein possess an acrylate, methacrylate and cinnamoyl functionality or a primary amine group.

Suitable free radical polymerizable groups include ethylenically unsaturated groups (i.e., vinyl groups) such as vinyl ethers, allyl groups, unsaturated monocarboxylic acids and unsaturated dicarboxylic acids. Unsaturated mono-carboxylic acids include acrylic acid, methacrylic acid and crotonic acid. Unsaturated dicarboxylic acids include maleic, fumaric, itaconic, mesaconic or citraconic acid.

Examples of commercially available di- and tetra functional monomers that can be used as cross-linkers in the invention compositions are alkyl fumarates; e.g., diethyl fumarate. Other examples include ester type multifunctional cross-linkers, such as tetra- and hexa-acrylates.

1.a. Alkyl fumarates with general formula (IX) below have been successfully used by several research groups as plasticizer or solvent and at same time as cross-linker in combination with unsaturated aliphatic polyester (J. P. Fisher et al., *Biomaterials* (2002) 22:4333-4343 and literature cited therein). When used as a cross-linker in combination with the polymers of structural formulas (I and III-VII) described herein, it has been discovered that, although functional as a cross-linker, diethyl fumarate, described by general structural formula (VIII) below, is rather inert during radical photo-crosslinking and requires longer exposure time than does fumaric acid-based oligo- or poly(ester amides) as cross-linkers.

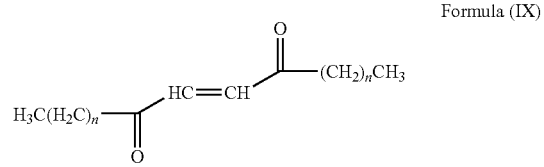

Formula (IX)

wherein, n=any integer from 0 to 12.

1.b. Ester type cross-linkers (ESC)s are the most inexpensive and widely available cross-linkers and can be synthesized by interaction of di-, tri-, tetra-, or poly-alcohols, such as polyvinyl alcohol, with unsaturated carbonic acid chlorides, such as acrylic, methacrylic, or cinnamic acid chloride. Examples of ESC cross-linkers include the following: 1,4-butanediol diacrylate, 1,4-butanediol di-methacrylate, 1,6-hexanediol diacrylate, 1,6-hexanediol di-methacrylate, penta-erythritol tri- and tetra-acrylates, which are commercially available, i.e. from Aldrich Chemicals. However, these commercial cross-linkers contain stabilizers that can inhibit photo-induced polymerization. Therefore, additional purification procedures are required. The use of freshly prepared inhibitor-free ESCs is advantageous for constructing polymeric architectures in combination with the polymers described herein having structural formulas (I and III-VII). The methods for preparing these types of compounds without using inhibitors are described in Example 1 below. Examples of di-functional ester type cross-linkers (ESC-2) suitable for use in the invention compositions and methods of use are based on non-toxic fatty diols, wherein the "2" designates (di-) functionality of the ESC (Formula X below):

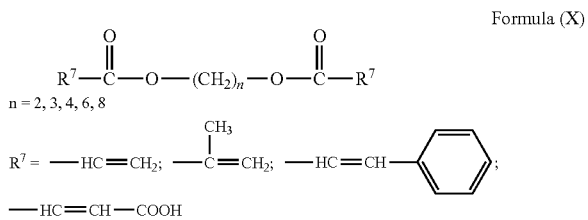

Formula (X)

1.c. Water soluble ester type cross-linkers (WESC) that are suitable for use in the invention compositions and methods have also been discovered. Di-functional WESC-2s are water soluble at pH greater than 7 and are maleic acid-based di-ester diacid-cross-linkers. When the linear polymer in an invention composition is an unsaturated derivative of a polysaccharide having average molecular weight from 10000 to 100000 Da, exposure of the cross-linker to active species forms a polymer network with properties of a hydrogel with an equilibrium swelling ratio percentage in water ranging from about 200 to about 1,500, for example from about 400 to about 1,200. The chemical structure of such water soluble cross-linkers is described by general structural formula (XI) below:

Formula (XI)

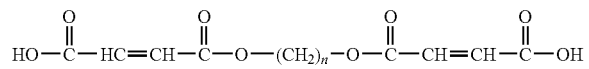

wherein n=any integer from 2 to 12.

Di-functional WESC-2s based on short aliphatic (fatty) diols have been synthesized by interaction of diols with maleic anhydride as described in Example 2 herein.

1.d. Polyfunctional ESCs, such as tri-, tetra- and higher functional cross-linkers, based on nontoxic poly-functional diols can be prepared analogously (as described in Examples 1 and 2 herein). Suitable poly-functional diols for use in preparation of such poly-functional cross-linkers include, but are not limited to, glycerol, tri-methylolpropane, penta-erytritol, tri-methylolpropane tri-acrylate, glycerol tri-acrylate, penta-erythritol tetraacrylate, di-pentaerythritol penta-/hexa-acrylate, and the like. Exemplary ESC-4s, have been prepared by condensing penta-erythritol with acryloyl, methacryloyl and cinnamoyl chlorides.

The general structural formula for oligo- and poly-meric ester type cross-linkers (ESC-P) based on poly(vinyl alcohol) is shown in Formula (XII) below:

Formula (XII)

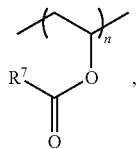

wherein n 2, 4, 6 or 8 and is $R^7$ is —CH=$CH_2$, —C($CH_3$)=$CH_2$, —CH=CH—($C_6H_5$), —CH=CH—COOH.

2.a. Diamine Type Non-Photo-Reactive Cross-Linkers

As illustrated in the Examples herein, diamines can also be applied for intra- and intermolecular crosslinking of unsaturated PEAs composed of fumaric acid, as well as epoxy-PEAs. Chemical crosslinking with model diamines (1,6-hexylene diamine, 1,12-dodecamethylene diamine) proceeds efficiently under mild (warming) conditions. Fatty diamines, however, are rather toxic and intermolecular links formed in these compounds are not biodegradable. Therefore, the more promising cross-linking agents are bis-(α-amino acid)-α,ω-alkylene diesters, i.e. (α-aminoacyl diols) separated from the corresponding di-p-toluenesulfonic acid salts as free bases. Bis-(α-amino acid)-α,ω-alkylene diesters represent key monomers used in formation of the above-described AABB type PEA, PEUR and PEU polymers (Formulas (I and III-VII).

Development of bis-(α-amino acid)-α,ω-alkylene diesters as non-photoreactive cross-linkers activated by diamine is consistent with the fact that the esters of N-acyl-L-α-amino acids are easily cleaved by the action of α-chymotrypsin, e.g. the rate of their hydrolysis is ~$10^5$ times higher than that of corresponding aliphatic amides (M. L. Bender and F. J. Kezdy, *Ann. Rev. Biochem*. (1965) 34:49 and I. V. Berezin, et al. *FEBS lett*. (1971) 15:125). Poly(ester amides) (PEAs) based on the same type of diester-diamine monomers have been known to be biodegradable in in-vitro biodegradation studies influenced by the esterases (G. Tsitlanadze, et al. *J. Biomater. Sci. Polymer Edn*. (2004). 15:1-24). Therefore, monomeric and oligomeric crosslinkers based on bis(α-aminoacyl)-α,ω-alkylene diesters also can be expected to be biodegradable when cross-linked due to the hydrolytically labile ester groups contained therein. Di-amine type non-photoreactive crosslinkers have been described in Example 3 herein.

3.a. The ester-amide type (EAC) cross-linkers are useful for preparation of fully biodegradable systems and when ester-type cross-linkers show low miscibility with (low affinity to) a crosslinkable scaffold polymer. The EAC cross-linkers are expected to show higher compatibility with PEAs, PEURs and PEUs disclosed herein than with other types of linear polymer due to their ester-amide nature and origin in non-toxic α-amino acids.

Three types of crosslinkers of the EAC family with photo-curable groups are herein disclosed: Di-functional ester-amide cross-linkers (EAC-2) are based on bis-(α-amino acyl) diol-diesters, which are also key monomers for the synthesis of AABB type biomedical polymers, have a chemical structure described by general structural formula (XIII) below:

Formula (XIII)

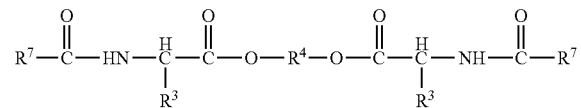

wherein, the $R^3$s in each n monomer are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and $(CH_2)_2SCH_3$; $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of general formula (II), and combinations thereof; and $R^7$ is independently selected from the group consisting of —CH=$CH_2$, —C($CH_3$)=$CH_2$, —CH=CH—($C_6H_5$), and —CH=CH—COOH.

3.b. The EAC crosslinker can also be poly-functional, such as a tri-, tetra-, penta- or hexa-functional crosslinker having a chemical structure as described by general structural formula (XIV) below:

Formula (XIV)

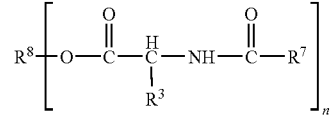

wherein n=3-6 and, wherein $R^8$ is the residue of a poly-functional aliphatic polyols, such as glycerol, trimethylol propane, pentaerythritol, di-pentaerythritol, and the like. For example $R^8$ can be selected from the group consisting of branched ($C_2$-$C_{12}$) alkylene or branched ($C_2$-$C_8$) alkyloxy ($C_2$-$C_{20}$) alkylene, Preferably $R^8$ is selected from the group consisting of —CH($CH_2$—$)_2$; $CH_3$—$CH_2$—C($CH_2$—$)_3$; C($CH_2$—$)_4$, and (—$CH_2)_3$C—$CH_2$—O—$CH_2$—C($CH_2$—$)_3$.

For example, tetra-functional cross-linker (EAC-4) described by structural formula (XV) below was synthesized based on tetra-p-toluenesulfonic acid salts of tetra-α-amino acyl) pentaerythritol was synthesized as described in Example 5 below:

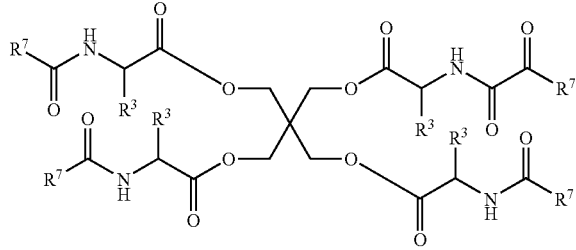

Formula (XV)

wherein, the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; and $R^5$ is selected from the group consisting of —CH=CH$_2$, —C(CH$_3$)=CH$_2$, —CH=CH—(C$_6$H$_5$), and —CH=CH—COOH.

3.c. Alternatively, the EAC cross-linker can be a polyamide type cross-linker (EAC-PA) having a chemical formula described by general formula (XVI).

Formula (XVI)

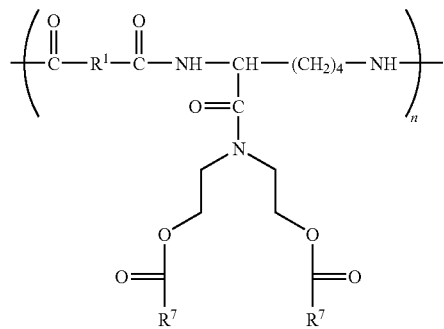

wherein n is about 10 to about 150; $R^1$ is independently selected from the group consisting of $(C_2-C_{20})$ alkylene, $(C_2-C_{20})$ alkenylene, residues of α,ω-bis(o,m, or p-carboxy phenoxy)-$(C_1-C_8)$ alkane, 3,3'-(alkenedioyldioxy) dicinnamic acid, 4,4'-(alkanedioyldioxy) dicinnamic acid, and combinations thereof; and $R^7$ is selected from the group consisting of —CH=CH$_2$, —C(CH$_3$)=CH$_2$, —CH=CH—(C$_6$H$_5$), and —CH=CH—COOH.

3.d. Alternatively still, the EAC crosslinker can be a poly (ester amide) crosslinker based on a PEA polymer (EAC-PEA) having a chemical formula described by general structural formula (XVII):

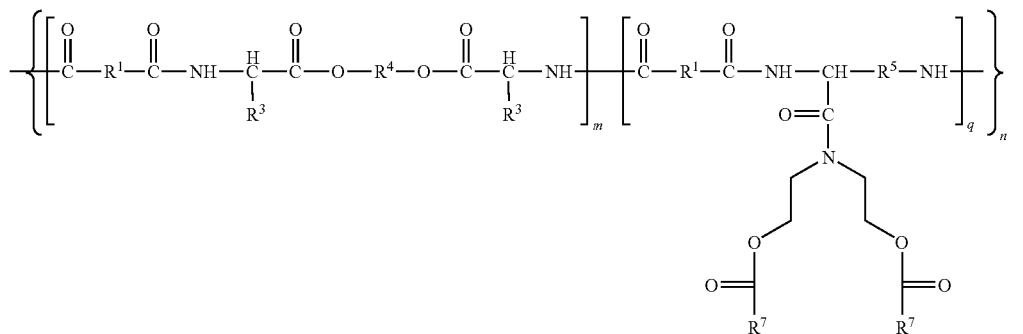

Formula (XVII)

wherein m is about 0.1 to about 0.9; q is about 0.9 to about 0.1, n is about 10 to about 150, each $R^1$ is independently selected from the group consisting of $(C_2-C_{20})$ alkylene, $(C_2-C_{20})$ alkenylene, residues of α,ω-bis(o,m, or p-carboxy phenoxy)-$(C_1-C_8)$ alkane, 3,3'-(alkenedioyldioxy) dicinnamic acid, 4,4'-(alkanedioyldioxy) dicinnamic acid, and combinations thereof; the $R^3$s in an m monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; and $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, a bicyclic-fragment of 1,4:3,6-dianhydrohexitol of general formula II, and combinations thereof; $R^5$ is independently $(C_2-C_{20})$ alkyl or $(C_2-C_{20})$ alkenyl; and $R^7$ is independently selected from the group consisting of —CH=CH$_2$, —C(CH$_3$)=CH$_2$, —CH=CH—(C$_6$H$_5$), and —CH=CH—COOH.

Reactive Diluents

The cross-linkers included in the invention compositions are considered reactive diluents if they modify the viscosity of the composition and adjust the cure rate of the composition. Reactive diluents include those cross-linkers, both monomers and macromers, described above.

Excipients

The compositions can also include particles of excipients, for example, ceramics. Suitable non-limiting examples of such excipients include hydroxy-apatite, plaster of paris, calcium carbonate, tri-calcium phosphate, polyphosphates, poly-phosphonate polyphosphates, and the like.

Bioactive Agents

The compositions can also include various bioactive agents of either therapeutic or diagnostic utility. The bioactive agents can be dispersed in the invention composition as described herein, or can be incorporated into microparticles, which are then incorporated into the composition. Incorporating the agents into microparticles can be advantageous for those agents that are undesirably reactive with one or more of the components of the invention composition, i.e., agents that have hydroxy or amine functionality and that are incorporated into compositions including ester linkages. Microparticles, and methods of preparation thereof, are well known to those of skill in the art.

Examples of bioactive agents that can be incorporated into the compositions include proteins, polysaccharides, nucleic acid molecules, and synthetic organic or inorganic molecules. These bioactive agents may be useful for therapeutic, palliative or diagnostic purposes. Drugs which can be used include anesthetics, antibiotics, antivirals, nucleic acids, chemotherapeutic agents, anti-angiogenic agents, hormones, drugs having an effect on vascular flow and anti-inflammatories.

The invention compositions can incorporate humoral factors to promote cell transplantation and engraftment. For example, the compositions can be combined with angiogenic factors, antibiotics, anti-inflammatories, growth factors, compounds which induce differentiation, and other factors of cell culture known to those skilled in the art that are suitable to achieve such goals. Nucleic acid molecules include genes, antisense molecules, which bind to complementary DNA to inhibit transcription, ribozymes and ribozyme guide sequences. Proteins are defined as consisting of 100 amino acid residues or more; peptides are less than 100 amino acid residues. Unless otherwise stated, the term protein refers to both proteins and peptides. Examples of such proteins include hormones. Polysaccharides, such as heparin, can also be administered. Compounds with a wide range of molecular weight, for example, between 50 and 500,000 Da, can be dispersed in the linear polymer incorporated into the composition or into the cross-linked composition prior to its drying and curing.

Bioactive agents for dispersion into and release from the invention compositions also include anti-proliferants, rapamycin and any of its analogs or derivatives, paclitaxel or any of its taxene analogs or derivatives, everolimus, Sirolimus, tacrolimus, or any of its limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-demethoxy-geldanamycin and other polyketide inhibitors of heat shock protein 90 (Hsp90), Cilostazol, and the like.

Additional bioactive agents contemplated for dispersion within the polymers used in the invention compositions include agents that, when freed or eluted from the polymer compositions, promote endogenous production of a therapeutic natural wound healing agent, such as nitric oxide, which is endogenously produced by endothelial cells. Alternatively the bioactive agents released from the polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such bioactive agents include, for example, aminoxyls, furoxans, nitrosothiols, nitrates and anthocyanins; nucleosides such as adenosine and nucleotides such as adenosine diphosphate (ADP) and adenosine triphosphate (ATP); neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

A variety of bioactive agents, coating molecules and ligands for bioactive agents can be attached, for example covalently, to polymers in the surface of the invention compositions. For example, targeting antibodies, polypeptides, drugs, and the like, can be covalently conjugated to the polymer at a surface of the composition. In addition, coating molecules, such as polyethylene glycol (PEG) as a ligand for attachment of antibodies or polypeptides or phosphatidylcholine (PC) as a means of blocking attachment sites on the surface of an article of manufacture to prevent the subject's non-target biological molecules and surfaces in the subject from sticking to the invention device.

For example, small proteinaceous motifs, such as the B domain of bacterial Protein A and the functionally equivalent region of Protein G are known to bind to, and thereby capture, antibody molecules by the Fc region. Such proteinaceous motifs can be attached to the polymers, especially to the polymers in surfaces of an internal fixation device. Such molecules will act, for example, as ligands to attach antibodies for use as targeting ligands or to capture antibodies to hold precursor cells or capture cells out of the patient's blood stream. Therefore, the antibody types that can be attached to polymer coatings using a Protein A or Protein G functional region are those that contain an Fc region. The capture antibodies will in turn bind to and hold precursor cells, such as progenitor cells, near the polymer surface while the precursor cells, which are preferably bathed in a growth medium within pores of the invention device secrete various factors and interact with other cells of the subject. In addition, one or more bioactive agents dispersed in the invention compositions or devices (e.g., in pores thereof), such as the bradykinins, may activate the precursor cells.

In addition, bioactive agents for attaching precursor cells or for capturing progenitor endothelial cells (PECs) from the subject's blood are monoclonal antibodies directed against a known precursor cell surface marker. For example, complementary determinants (CDs) that have been reported to decorate the surface of endothelial cells include CD31, CD34, CD102, CD105, CD106, CD109, CDw130, CD141, CD142, CD143, CD144, CDw145, CD146, CD147, and CD166. These cell surface markers can be of varying specificity and the degree of specificity for a particular cell/developmental type/stage is in many cases not fully characterized. In addition these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which the invention composition or device is implanted for local delivery of the active agents. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies.

The following bioactive agents (including organic or inorganic synthetic molecules (e.g., drugs)) will be particularly effective for dispersion within the polymers of the invention compositions when selected for their suitable therapeutic or palliative effect in treatment of a disease or conditions of interest, or symptoms thereof.

In one embodiment, the suitable bioactive agents are not limited to, but include, various classes of compounds that facilitate or contribute to wound healing, especially when presented in a time-release fashion. Such bioactive agents include wound-healing cells, including certain precursor cells, which can be protected and delivered by the invention compositions and devices. Such wound healing cells include, for example, pericytes and endothelial cells, as well as inflammatory healing cells. To recruit such cells to the site of implant in vivo of a device manufactured using the invention composition, ligands for such cells, such as antibodies and smaller molecule ligands, that specifically bind to "cellular adhesion molecules" (CAMs) can be used. Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD 106 antigen); Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1 or LECAM-2 (CD62E antigen), and the like.

In another aspect, the suitable bioactive agents include extra cellular matrix proteins, macromolecules that can be dispersed into the polymers used in the invention compositions and devices, e.g., attached either covalently or non-covalently. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used as the bioactive agent.

Proteinaceous growth factors are an additional category of bioactive agents suitable for dispersion in the invention compositions and devices described herein. Such bioactive agents are effective in promoting wound healing and other disease states as is known in the art. For example, Platelet Derived Growth Factor-BB (PDGF-BB), Tumor Necrosis Factor-alpha (TNF-$\alpha$), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF-beta), and Insulin-like Growth Factor-1 (IGF-1). Many of these proteinaceous growth factors are available commercially or can be produced recombinantly using techniques well known in the art.

Alternatively, growth factors such as VEGFs, PDGFs, FGF, NGF, and evolutionary and functionally related biologics, and angiogenic enzymes, such as thrombin, may also be used as bioactive agents in the invention.

Organic or inorganic synthetic molecules, such as drugs, are an additional category of bioactive agents suitable for dispersion in the invention compositions and devices described herein. Such drugs include, for example, antimicrobials and anti-inflammatory agents as well as certain healing promoters, such as, for example, vitamin A and synthetic inhibitors of lipid peroxidation.

A variety of antibiotics can be used in the invention compositions to indirectly promote natural healing processes by preventing or controlling infection. Suitable antibiotics include many classes, such as aminoglycoside antibiotics or quinolones or beta-lactams, such as cefalosporins, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc., 1997, 119, 12041-12047; and J. Amer. Chem. Soc., 1994, 116, 45734590, Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, included alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory bioactive agents are also useful for dispersion in polymer particles used in the invention compositions and methods. Depending on the body site of implant, disease to be treated, and desired effect, such anti-inflammatory bioactive agents include, e.g. analgesics (e.g., NSAIDS and salicyclates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician's Desk Reference,* 2001 Edition. Specifically, the anti-inflammatory agent can include dexamethasone, which is chemically designated as (11 1, 16I)-9-fluoro-11,17,21-trihydroxy-16-methylpregna-1,4-diene-3,20-dione. Alternatively, the anti-inflammatory bioactive agent can be or include sirolimus (rapamycin), which is a triene macrolide antibiotic isolated from *Streptomyces hygroscopicus.*

The polypeptide bioactive agents included in the invention compositions and methods can also include "peptide mimetics." Such peptide analogs, referred to herein as "peptide mimetics" or "peptidomimetics," are commonly used in the pharmaceutical industry with properties analogous to those of the template peptide. (Fauchere, J. (1986) *Adv. Bioactive agent Res.,* 15:29; Veber and Freidinger (1985) *TINS* p. 392; and Evans et al. (1987) J. Med. Chem., 30:1229) and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —CH$_2$NH—, —CH$_2$S—, —CH$_2$—CH$_2$—, —CH=CH— (cis and trans), —COCH$_2$—, —CH(OH)CH$_2$—, and —CH$_2$SO—, by methods known in the art and further described in the following references: Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.,* (1980) pp. 463-468 (general review); Hudson, D. et al., *Int. J. Pept. Prot. Res.,* (1979) 14:177-185 (—CH$_2$NH—, CH$_2$CH$_2$—); Spatola, A. F. et al., *Life Sci.,* (1986) 38:1243-1249 (—CH$_2$—S—); Harm, M. M., *J. Chem. Soc.* Perkin Trans I (1982) 307-314 (—CH=CH—, cis and trans); Almquist, R. G. et al., *J. Med. Chem.,* (1980) 23:2533 (—COCH$_2$—); Jennings-Whie, C. et al., *Tetrahedron Lett.,* (1982) 23:2533 (—COCH$_2$—); Szelke, M. et al., European Appln., EP 45665 (1982) CA: 97:39405 (1982) (—CH(OH) CH$_2$—); Holladay, M. W. et al., *Tetrahedron Lett.,* (1983) 24:4401-4404 (—C(OH)CH$_2$—); and Hruby, V. J., *Life Sci.,* (1982) 31:189-199 (—CH$_2$—S—). Such peptide mimetics may have significant advantages over natural polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide (e.g., with a D-Lysine in place of L-Lysine) may be used to generate more stable peptides and peptides resistant to endogenous peptidases. Alternatively, the synthetic polypeptides covalently bound to the biodegradable polymer, can also be prepared from D-amino acids, referred to as inverso peptides. When a peptide is assembled in the opposite direction of the native peptide sequence, it is referred to as a retro peptide. In general, polypeptides prepared from D-amino acids are very stable to enzymatic hydrolysis. Many cases have been reported of preserved biological activities for retro-inverso or partial retro-inverso polypeptides (U.S. Pat. No. 6,261,569 B1 and references therein; B. Fromme et al, *Endocrinology* (2003) 144:3262-3269.

The invention compositions optionally may comprise an "effective amount" of a bioactive agent(s) of interest. That is, an amount of a bio active agent may be included in the compositions that will cause the subject to produce a sufficient therapeutic, palliative or diagnostic response, for example, in order to prevent, reduce or eliminate symptoms. The exact amount necessary will vary, depending on the subject being treated; the age and general condition of the subject to be treated; the capacity of the subject's immune system, the degree of protection desired; the severity of the condition being treated; the particular active agent selected and mode of administration of the composition, among other factors. An appropriate effective amount can be readily determined by one of skill in the art. Thus, an "effective amount" will fall in a relatively broad range that can be determined through routine trials. For example, for purposes of the present invention, an effective amount will typically range from about 1 μg to about 100 mg, for example from about 5 μg to about 1 mg, or about 10 μg to about 500 μg of the active agent delivered per dose.

In one embodiment, the linear polymers bear functionalities that allow facile covalent attachment of the bioactive agent(s) or covering molecule(s) to the polymer. For example, a polymer bearing carboxyl groups can readily react with an amino moiety, thereby covalently bonding a peptide to the polymer via the resulting amide group. As will be described herein, the biodegradable polymer and the bioactive agent may contain numerous complementary functional groups that can be used to covalently attach the bioactive agent to the biodegradable polymer.

While the bioactive agents can be dispersed within the polymer matrix without chemical linkage to the linear polymer, it is also contemplated that a bioactive agent can be covalently bound to the biodegradable polymers via a wide variety of suitable functional groups. For example, when the biodegradable polymer is a polyester, the carboxyl group chain end can be used to react with a complimentary moiety on the bioactive agent or covering molecule, such as hydroxy, amino, thio, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

For example, many of the PEA, PEUR and PEU polymers described for use in the invention compositions and devices have built-in functional groups on side chains, and these built-in functional groups can react with other chemicals and lead to the incorporation of additional functional groups to expand the functionality of the polymers further. Therefore, such polymers used in the invention methods are ready for reaction with other chemicals having a hydrophilic structure to increase water solubility and with bioactive agents and covering molecules, without the necessity of prior modification.

In other embodiments, a bioactive agent can be linked to the PEA, PEUR or PEU polymers described herein through an amide, ester, ether, amino, ketone, thioether, sulfinyl, sulfonyl, or disulfide linkage. Such a linkage can be formed from suitably functionalized starting materials using synthetic procedures that are known in the art.

For example, in one embodiment a polymer can be linked to the bioactive agent via an end or pendent carboxyl group (e.g., COOH) of the polymer. For example, a compound of structures III, V, and VII can react with an amino functional group or a hydroxyl functional group of a bioactive agent to provide a biodegradable polymer having the bioactive agent attached via an amide linkage or carboxylic ester linkage, respectively. In another embodiment, the carboxyl group of the polymer can be benzylated or transformed into an acyl halide, acyl anhydride/"mixed" anhydride, or active ester. In other embodiments, the free —$NH_2$ ends of the polymer molecule can be acylated to assure that the bioactive agent will attach only via a carboxyl group of the polymer and not to the free ends of the polymer.

Water soluble covering molecule(s), such as poly(ethylene glycol) (PEG); phosphoryl choline (PC); glycosaminoglycans including heparin; polysaccharides including polysialic acid; poly(ionizable or polar amino acids) including polyserine, polyglutamic acid, polyaspartic acid, polylysine and polyarginine; chitosan and alginate, as described herein, and targeting molecules, such as antibodies, antigens and ligands, can also be conjugated to the polymer in the exterior of the particles after production of the particles to block active sites not occupied by the bioactive agent or to target delivery of the particles to a specific body site as is known in the art. The molecular weights of PEG molecules on a single particle can be substantially any molecular weight in the range from about 200 to about 200,000, so that the molecular weights of the various PEG molecules attached to the particle can be varied.

Alternatively, a bioactive agent can be attached to the linear polymer via a linker molecule. For example, to improve surface hydrophobicity of the biodegradable linear polymer, to improve accessibility of the biodegradable polymer towards enzymatic activation, and to improve the release profile of the invention composition, a linker may be utilized to indirectly attach the bioactive agent to the biodegradable linear polymer. In certain embodiments, the linker compounds include poly(ethylene glycol) having a molecular weight (MW) of about 44 to about 10,000, preferably 44 to 2000; amino acids, such as serine; polypeptides with repeat number from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is ($C_1$-$C_{24}$) alkyl, ($C_2$-$C_{24}$) alkenyl, ($C_2$-$C_{24}$) alkynyl, ($C_3$-$C_8$) cycloalkyl, or ($C_6$-$C_{10}$) aryl, and W and Q are each independently —N(R)C(=O)—, —C(=O)N(R)—, —OC(=O)—, —C(=O)O, —O—, —S—, —S(O), —S(O)$_2$—, —S—S—, —N(R)—, —C(=O)—, wherein each R is independently H or ($C_1$-$C_6$) alkyl.

As used to describe the above linkers, the term "alkyl" refers to a straight or branched chain hydrocarbon group including methyl, ethyl, n-propyl, isopropyl, n-butyl, isobutyl, tert-butyl, n-hexyl, and the like.

As used herein to describe the above linkers to describe the above linkers, "alkenyl" refers to straight or branched chain hydrocarbyl groups having one or more carbon-carbon double bonds.

As used herein to describe the above linkers, "alkynyl" refers to straight or branched chain hydrocarbyl groups having at least one carbon-carbon triple bond.

As used herein to describe the above linkers, "aryl" refers to aromatic groups having in the range of 6 up to 14 carbon atoms.

In certain embodiments, the linker may be a polypeptide having from about 2 up to about 25 amino acids. Suitable peptides contemplated for use include poly-L-glycine, poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, poly-L-lysine-L-tyrosine, and the like.

In one embodiment, the bioactive agent covalently crosslinks the PEA, PEUR or PEU polymer, i.e. the bioactive agent is bound to more than one polymer molecule. This covalent crosslinking can be done with or without additional polymer-bioactive agent linker.

The bioactive agent molecule can also be incorporated into an intramolecular bridge by covalent attachment between two polymer molecules.

A linear polymer polypeptide conjugate is made by protecting the potential nucleophiles on the polypeptide backbone and leaving only one reactive group to be bound to the polymer or polymer linker construct. Deprotection is performed according to methods well known in the art for deprotection of peptides (Boc and Fmoc chemistry for example).

In one embodiment of the present invention, a polypeptide bioactive agent is presented as retro-inverso or partial retro-inverso peptide.

The linker can be attached first to the linear polymer or to the bioactive agent or covering molecule. During synthesis, the linker can be either in unprotected form or protected form, using a variety of protecting groups well known to those skilled in the art. In the case of a protected linker, the unprotected end of the linker can first be attached to the polymer or the bioactive agent or covering molecule. The protecting group can then be de-protected using Pd/$H_2$ hydrogenolysis, mild acid or base hydrolysis, or any other common de-protection method that is known in the art. The de-protected linker can then be attached to the bioactive agent or covering molecule, or to the polymer.

An exemplary synthesis of a biodegradable polymer according to the invention (wherein the molecule to be attached is an aminoxyl) is set forth as follows.

A polyester can be reacted with an amino-substituted aminoxyl (N-oxide) radical bearing group, e.g., 4-amino-2,2,6,6-tetramethylpiperidine-1-oxy, in the presence of N,N'-carbonyldiimidazole to replace the hydroxyl moiety in the carboxyl group at the chain end of the polyester with an amino-substituted aminoxyl-(N-oxide) radical bearing group, so that the amino moiety covalently bonds to the carbon of the carbonyl residue of the carboxyl group to form an amide bond. The N,N'-carbonyl diimidazole or suitable carbodiimide converts the hydroxyl moiety in the carboxyl group at the chain end of the polyester into an intermediate product moiety which will react with the aminoxyl, e.g., 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyl diimidazole to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly- L-lactic acid, a poly-DL-lactic acid or a poly(glycolide-L-lactide) (having a monomer mole ratio of glycolic acid to L-lactic acid 50:50 or less than 50:50), tetrahydrofuran, dichloromethane (DCM) and chloroform at room temperature to 40–50° C. suitably dissolve the polyester.

For example, one residue of the polymer can be directly linked to one residue of the bioactive agent. The polymer and the bioactive agent can each have one open valence. Alternatively, more than one bioactive agent, multiple bioactive agents, or a mixture of bioactive agents having different therapeutic or palliative activity can be directly linked to the polymer. However, since the residue of each bioactive agent can be linked to a corresponding residue of the polymer, the number of residues of the one or more bioactive agents can correspond to the number of open valences on the residue of the polymer.

As used herein, a "residue of a polymer" refers to a radical of a polymer having one or more open valences. Any synthetically feasible atom, atoms, or functional group of the polymer (e.g., on the polymer backbone or pendant group) of the present invention can be removed to provide the open valence, provided bioactivity is substantially retained when the radical is attached to a residue of a bioactive agent. Additionally, any synthetically feasible functional group (e.g., carboxyl) can be created on the polymer (e.g., on the polymer backbone or pendant group) to provide the open valence, provided bioactivity is substantially retained when the radical is attached to a residue of a bioactive agent. Based on the linkage that is desired, those skilled in the art can select suitably functionalized starting materials that can be derived from the polymer of the present invention using procedures that are known in the art.

As used herein, a "residue of a compound of structural formula (*)" refers to a radical of a compound of polymer formulas (I) and (III-VII) as described herein having one or more open valences. Any synthetically feasible atom, atoms, or functional group of the compound (e.g., on the polymer backbone or pendant group) can be removed to provide the open valence, provided bioactivity is substantially retained when the radical is attached to a residue of a bioactive agent. Additionally, any synthetically feasible functional group (e.g., carboxyl) can be created on the compound of formulas (I) and (III-VII) (e.g., on the polymer backbone or pendant group) to provide the open valance, provided bioactivity is substantially retained when the radical is attached to a residue of a bioactive agent. Based on the linkage that is desired, those skilled in the art can select suitably functionalized starting materials that can be derived from the compound of formulas (I) and (III-VII) using procedures that are known in the art.

For example, the residue of a bioactive agent can be linked to the residue of a compound of structural formula (I) or (III-VII) through an amide (e.g., —N(R)C(=O)— or —C(=O)N(R)—), ester (e.g., —OC(=O)— or —C(=O)O—), ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or ($C_1$-$C_6$) alkyl. Such a linkage can be formed from suitably functionalized starting materials using synthetic procedures that are known in the art. Based on the linkage that is desired, those skilled in the art can select suitably functional starting material that can be derived from a residue of a compound of structural formula (I) or (III-VII) and from a given residue of a bioactive agent or adjuvant using procedures that are known in the art. The residue of the bioactive agent or adjuvant can be linked to any synthetically feasible position on the residue of a compound of structural formula (I) or (III-VII). Additionally, the invention also provides compounds having more than one residue of a bioactive agent or adjuvant bioactive agent directly linked to a compound of structural formula (I) or (III-VII).

The number of bioactive agents that can be directly linked to the PEA, PEUR or PEU polymer molecule can typically depend upon the molecular weight of the polymer. For example, for a compound of structural formula (I), wherein n is about 5 to about 150, preferably about 5 to about 70, up to about 150 bioactive agent molecules (i.e., residues thereof) can be directly linked to the polymer (i.e., residue thereof) by reacting the bioactive agent with side groups of the polymer. In unsaturated polymers, the bioactive agents can also be reacted with double (or triple) bonds in the polymer.

The PEA, PEUR and PEU polymers described herein absorb water, (5 to 25% w/w water up-take, on polymer film) allowing hydrophilic molecules to readily diffuse therethrough. This characteristic makes these polymers suitable for use as an over coating on articles of manufacturer to control release rate. Water absorption also enhances biocompatibility of the polymers and the compositions based on such polymers.

Therapeutic and Palliative Agents

Bioactive agents useful in the invention compositions and method include any of a variety of therapeutic and palliative agents, which can be dispersed within the invention compositions to locally or systemically deliver the incorporated diagnostic agents following administration and crosslinking of the composition or implant of an article of manufacture made using or comprising the composition.

Diagnostic Agents

Bioactive agents useful in the invention compositions and methods also include any of a variety of diagnostic agents, which can be dispersed within the invention compositions to locally or systemically deliver the incorporated diagnostic agents following administration and crosslinking of the composition or implant of an article of manufacture containing the composition. For example, imaging agents can be used to allow monitoring of bone repair following implantation of the compositions in a subject. Suitable imaging agents include commercially available agents used in such techniques as positron emission tomography (PET), computer assisted tomography (CAT), single photon emission computerized tomography, x-ray, fluoroscopy, magnetic resonance imaging (MRI), and the like.

Non-limiting examples of suitable materials for use as contrast agents in MRI, which are well known in the art, include the gadolinium chelates currently available, such as diethylene triamine pentaacetic acid (DTPA) and gadopentotate dimeglumine, as well as iron, magnesium, manganese, copper, chromium, and the like. Non-limiting examples of materials useful for CAT and x-rays, which are well known in the art, include iodine based materials, such as ionic monomers typified by diatrizoate and iothalamate, non-ionic monomers such as iopamidol, isohexyl, and ioversol, non-ionic dimers, such as iotrol and iodixanol, and ionic dimers, for example, ioxagalte.

These agents can be detected using standard techniques available in the art and commercially available equipment.

Porosity Forming Agents

The compositions can also include various inorganic salts, proteinaceous materials, such as gelatin, and combinations thereof, that dissolve at a relatively faster rate under physiological conditions than the rate of degradation of the composition. The relatively rapid dissolution of these particles creates porosity in the composition once the particles have dissolved. The materials can be selected to have a desired size or size distribution suitable to these goals, and can be evenly distributed throughout the composition to provide controlled porosity.

Suitable porosity-forming materials include particles of salts. The particles can be any salt that forms crystals or particles with a diameter of approximately 100 to 250 microns, does not react with the polymer, and is non-toxic if some residue remains in the polymer after leaching. Further, the microparticles described above can also be used to provide porosity, if the particles degrade at a faster rate than the crosslinked composition. Non-limiting examples of other porosity forming agents suitable for use in the invention compositions include proteins such as gelatin and agarose, starches, polysaccharides such as alginate, other polymers, and the like. For example, the salt can be a sodium salt, such as sodium chloride, sodium tartrate, sodium citrate, and other water soluble salts not soluble in the polymer solvent, for example, THF.

Preferably, the particles are first sieved through a mesh or a series of screens to provide particles of relatively uniform diameter. The particles are then added to the composition. The initial weight fraction of porosity forming agents is preferably from about 0.02% and about 0.9% by dry weight. The initial weight fraction is instrumental in determining the porosity characteristics, and hence the utilities, of the semi-interpenetrating polymer composition.

A particulate leaching process can be used to create a porous polymeric matrix. In one embodiment, salt particles are suspended in a solution that includes the linear polymer and the reactive cross-linkers, the solvent is removed, and the particles are leached out of the hardened polymer after the monomers and/or macromers are polymerized. Because enzymatically hydrolyzable bonds are present in the composition, it is preferable to avoid using enzymatic solutions to remove salts to create porosity, but rather, to employ water or other aqueous solutions (saline, buffer) of pH 5-8 to create the porosity.

Removal of the particles will create a polymer matrix having a plurality of relatively evenly spaced interconnected interstitial spaces or pores, formerly occupied by the particle crystals, into which cells can migrate, attach, and proliferate. The porosity of the matrix can be very high, typically between 60% and 90%, depending on the amount of incorporated particles.

Formation of an interconnecting network of pores in the cross-linked composition is known to facilitate the invasion of cells and promote an organized growth of the incoming cells and tissue. Porosity also has been demonstrated to influence the biocompatibility and bony integration into various porous materials, with a pore size of over a 100 microns being suitable for regenerating cells and promoting bony ingrowth. Accordingly, the pores in the invention composition can have a pore size in the range from about 100 microns to about 250 microns, which size is accomplished by appropriate selection of the size of the leachable particles.

Solvents

The composition can be dissolved in a solvent that does not adversely affect or react with the components or any particles to be suspended in the solution. The relative amount of solvent will have a minimal effect on the structure of the produced matrix, but will affect the solvent evaporation time. The concentration of the composition in the solvent will typically be in the range of between one and 50 percent, preferably between 10 and 30% w/v.

Solvents used should be non-reactive with the components of the composition. It is preferable that no protic solvents are used since ester linkages are present. Halogenated solvents may be used in those embodiments wherein the composition is polymerized ex vivo so that solvents can be effectively removed prior to implanting articles of manufacture, such as an internal fixation device prepared from the crosslinked composition. It is preferred to use solvents which are non-toxic for in vivo applications. Suitable solvents for these applications include glyme (polyglycol dimethyl ethers), dimethylsulfoxide (DMSO) and other polar aprotic solvents.

Synthesis of Amino Acid-Containing Polymers

Methods for making polymers of structural formulas containing α-amino acids in the general formula are well known in the art. For example, for the embodiment of the polymer of structural formula (I) wherein $R^4$ is incorporated into an α-amino acid, for polymer synthesis the α-amino acid with pendant $R^3$ can be converted through esterification into a bis-α,ω-diamine, for example, by condensing the α-amino acid containing pendant $R^3$ with a diol HO—$R^4$—OH. As a result, di-ester monomers with reactive α,ω-amino groups are formed. Then, the bis-α,ω-diamine is entered into a polycondensation reaction with a di-acid such as sebacic acid, or bis-activated esters, or bis-acyl chlorides, to obtain the final polymer having both ester and amide bonds (PEA). Alternatively, for example, for polymers of structure (I), instead of the di-acid, an activated di-acid derivative, e.g., bis-para-nitrophenyl diester, can be used as an activated di-acid. Additionally, a bis-dicarbonate, such as bis(p-nitrophenyl) dicarbonate, can be used as the activated species to obtain polymers containing a residue of a di-acid. In the case of PEUR polymers, a final polymer is obtained having both ester and urethane bonds.

More particularly, synthesis of the unsaturated poly(ester-amide)s (UPEAs) useful as biodegradable polymers of the structural formula (I) as disclosed above will be described, wherein

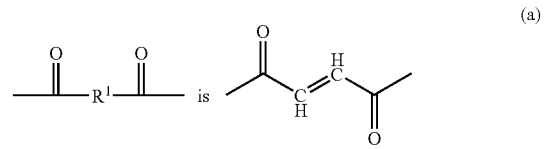

and/or (b) $R^4$ is $CH_2$—CH=CH—$CH_2$—. In cases where (a) is present and (b) is not present, $R^4$ in (I) is —$C_4H_8$— or —$C_6H_{12}$—. In cases where (a) is not present and (b) is present, $R^1$ in (I) is —$C_4H_8$— or —$C_8H_{16}$—.

The UPEAs can be prepared by solution polycondensation of either (1) di-p-toluene sulfonic acid salt of bis(α-amino acid) diesters, comprising at least 1 double bond in $R^4$, and di-p-nitrophenyl esters of saturated dicarboxylic acid or (2) di-p-toluene sulfonic acid salt of bis (α-amino acid) diesters, comprising no double bonds in $R^4$, and di-nitrophenyl ester of unsaturated dicarboxylic acid or (3) di-p-toluene sulfonic acid salt of bis(α-amino acid) diesters, comprising at least one double bond in $R^4$, and di-nitrophenyl esters of unsaturated dicarboxylic acids.

Salts of p-toluene sulfonic acid are known for use in synthesizing polymers containing amino acid residues. The aryl sulfonic acid salts are used instead of the free base because the aryl sulfonic salts of bis(α-amino acid) diesters are easily purified through recrystallization and render the amino groups as unreactive ammonium tosylates throughout workup. In the polycondensation reaction, the nucleophilic amino group is readily revealed through the addition of an organic base, such as triethylamine, so the polymer product is obtained in high yield.

The di-p-nitrophenyl esters of unsaturated dicarboxylic acid can be synthesized from p-nitrophenol and unsaturated dicarboxylic acid chloride, e.g., by dissolving triethylamine and p-nitrophenol in acetone and adding unsaturated dicarboxylic acid chloride drop wise with stirring at −78° C. and pouring into water to precipitate product. Suitable acid chlorides useful for this purpose include fumaric, maleic, mesaconic, citraconic, glutaconic, itaconic, ethenyl-butane dioic and 2-propenyl-butanedioic acid chlorides.

The di-aryl sulfonic acid salts of bis(α-amino acid) diesters can be prepared by admixing α-amino acid, p-aryl sulfonic acid (e.g. p-toluene sulfonic acid monohydrate), and saturated or unsaturated diol in toluene, heating to reflux temperature, until water evolution is minimal, then cooling. The unsaturated diols useful for this purpose include, for example, 2-butene-1,3-diol and 1,18-octadec-9-en-diol.

Saturated di-p-nitrophenyl esters of dicarboxylic acids and saturated di-p-toluene sulfonic acid salts of bis(α-amino acid) di-esters can be prepared as described in U.S. Pat. No. 6,503,538 B1.

Synthesis of the unsaturated poly(ester-amide)s (UPEAs) useful as biodegradable polymers of the structural formula (I) as disclosed above will now be described. UPEAs having the structural formula (I) can be made in similar fashion to the compound (VII) of U.S. Pat. No. 6,503,538 B1, except that $R^4$ of (III) of U.S. Pat. No. 6,503,538 and/or $R^1$ of (V) of U.S. Pat. No. 6,503,538 is ($C_2$-$C_{20}$) alkenylene as described above. The reaction is carried out, for example, by adding dry triethylamine to a mixture of said (III) and (IV) of U.S. Pat. No. 6,503,538 and said (V) of U.S. Pat. No. 6,503,538 in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenol and p-toluene sulfonate. A preferred reactant (IV) is p-toluene sulfonic acid salt of Lysine benzyl ester, the benzyl ester protecting group is preferably removed from (II) to confer biodegradability, but it should not be removed by hydrogenolysis as in Example 22 of U.S. Pat. No. 6,503, 538 because hydrogenolysis would saturate the desired double bonds; rather the benzyl ester group should be converted to an acid group by a method that would preserve unsaturation. Alternatively, the lysine reactant (IV) can be protected by a protecting group different from benzyl that can be readily removed in the finished product while preserving unsaturation, e.g., the lysine reactant can be protected with t-butyl (i.e., the reactant can be t-butyl ester of lysine) and the t-butyl can be converted to H while preserving unsaturation by treatment of the product (II) with acid.

A working example of the compound having structural formula (I) is provided by substituting p-toluene sulfonic acid salt of bis(L-phenylalanine)-2-butenediol-1,4-diester for (III) in Example 1 of U.S. Pat. No. 6,503,538 or by substituting di-p-nitrophenyl fumarate for (V) in Example 1 of U.S. Pat. No. 6,503,538 or by substituting p-toluene sulfonic acid salt of bis(L-phenylalanine)-2-butenediol-1,3-diester for III in Example 1 of U.S. Pat. No. 6,503,538 and also substituting de-p-nitrophenyl fumarate for (V) in Example 1 of U.S. Pat. No. 6,503,538.

In unsaturated compounds having either structural formula (I) or (III), the following hold: Aminoxyl radical e.g., 4-amino TEMPO, can be attached using carbonyldiimidazol, or suitable carbodiimide, as a condensing agent. Bioactive agents, as described herein, can be attached via the double bond functionality. Hydrophilicity can be imparted by bonding to poly(ethylene glycol) diacrylate.

In yet another aspect, polymers contemplated for use in forming the invention compositions include those set forth in U.S. Pat. Nos. 5,516,881; 6,476,204; 6,503,538; and in U.S. application Ser. Nos. 10/096,435; 10/101,408; 10/143,572; and 10/194,965, 10/362,848 11/344,689, 11/344,689, 11/543,321, 11/584,143; the entire contents of each of which is incorporated herein by reference.

The biodegradable PEA, PEUR and PEU polymers and copolymers may contain up to two amino acids per monomer, multiple amino acids per polymer molecule, and preferably have weight average molecular weights ranging from 10,000 to 125,000; these polymers and copolymers typically have intrinsic viscosities at 25° C., determined by standard viscosimetric methods, ranging from 0.3 to 4.0, for example, ranging from 0.5 to 3.5.

Synthesis of polymers contemplated for use in the practice of the invention can be accomplished by a variety of methods well known in the art. For example, tributyltin (IV) catalysts are commonly used to form polyesters such as poly(ε-caprolactone), poly(glycolide), poly(lactide), and the like. However, it is understood that a wide variety of catalysts can be used to form polymers suitable for use in the practice of the invention.

Such poly(caprolactones) contemplated for use have an exemplary structural formula (XVIII) as follows:

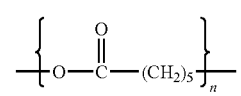

Formula (XVIII)

Poly(glycolides) contemplated for use have an exemplary structural formula (XIX) as follows:

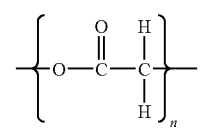

Formula (XIX)

Poly(lactides) contemplated for use have an exemplary structural formula (XX) as follows:

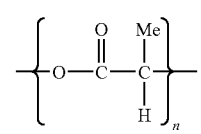

Formula (XX)

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (XXI).

Formula (XXI)

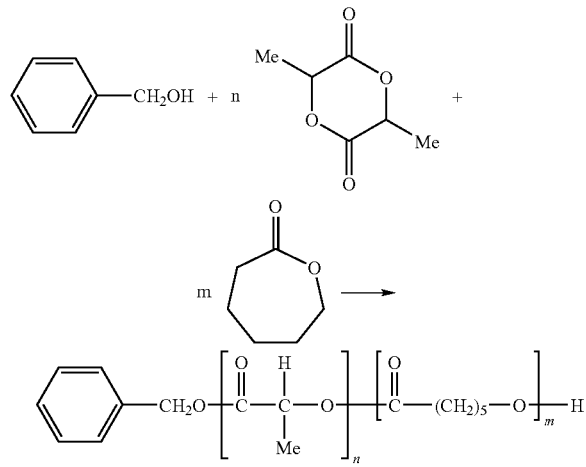

The hydroxy terminated polymer chains can then be capped with maleic anhydride to form polymer chains having structural formula (XXII):

Formula (XXII)

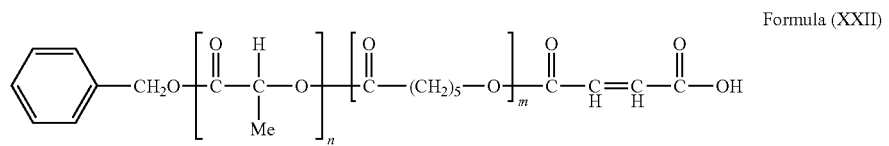

At this point, 4-amino-2,2,6,6-tetramethylpiperidine-1-oxy can be reacted with the carboxylic end group to covalently attach the aminoxyl moiety to the copolymer via the amide bond which results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

In unsaturated compounds having structural formula (VII) for PEU, the following hold: An amino substituted aminoxyl (N-oxide) radical bearing group e.g., 4-amino TEMPO, can be attached using carbonyldiimidazole, or suitable carbodiimide, as a condensing agent. Additional bioactive agents, and the like, as described herein, optionally can be attached via the double bond.

For example, the invention high molecular weight semi-crystalline PEUs having structural formula (VI) can be prepared inter-facially by using phosgene as a bis-electrophilic monomer in a chloroform/water system, as shown in the reaction scheme (1) below:

Scheme (1)

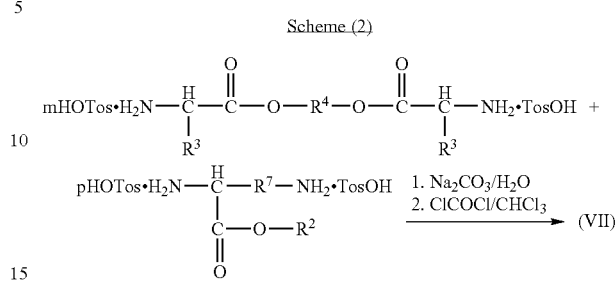

Synthesis of copoly(ester ureas) (PEUs) containing L-Lysine esters and having structural formula (VII) can be carried out by a similar scheme (2):

Scheme (2)

mHOTos•H₂N—C(H)(R³)—C(O)—O—R⁴—O—C(O)—C(H)(R³)—NH₂•TosOH + pHOTos•H₂N—C(H)(R⁷—NH₂•TosOH)(C(O)—O—R²)
1. Na₂CO₃/H₂O
2. ClCOCl/CHCl₃
→ (VII)

A 20% solution of phosgene (ClCOCl) (highly toxic) in toluene, for example (commercially available (Fluka Chemie, GMBH, Buchs, Switzerland), can be substituted either by diphosgene (trichloromethylchloroformate) or triphosgene (bis(trichloromethyl)carbonate). Less toxic carbonyldiimidazole can be also used as a bis-electrophilic monomer instead of phosgene, di-phosgene, or tri-phosgene.

It is necessary to use cooled solutions of monomers to obtain PEUs of high molecular weight. For example, to a suspension of di-p-toluenesulfonic acid salt of bis(α-amino acid)-α,ω-alkylene diester in 150 mL of water, anhydrous sodium carbonate is added, stirred at room temperature for about 30 minutes and cooled to about 2-0° C., forming a first solution. In parallel, a second solution of phosgene in chloroform is cooled to about 15-10° C. The first solution is placed into a reactor for interfacial polycondensation and the second solution is quickly added at once and stirred briskly for about 15 min. Then the chloroform layer can be separated, dried over anhydrous Na₂SO₄, and filtered. The obtained solution can be stored for further use.

All the exemplary PEU polymers fabricated were obtained as solutions in chloroform and these solutions are stable during storage. However, some polymers, for example, 1-Phe-4, become insoluble in chloroform after separation. To overcome this problem, polymers can be separated from chloroform solution by casting onto a smooth hydrophobic surface and allowing the chloroform to evaporate to dryness. No further purification of obtained PEUs is needed. The yield and characteristics of exemplary PEUs obtained by this procedure are summarized in Table 1 herein.

Methods for making the PEU polymers will now be described. For example, for the embodiment of the polymer of formula (VI) or (VII), the α-amino acid can be converted into a bis-(α-amino acid)-α,ω-diol-diester monomer, for example, by esterification the α-amino acid with a diol HO—R¹—OH in the presence of p-toluenesulfonic acid. As a result, ester bonds are formed. Then, acid chloride of carbonic acid (phosgene, diphosgene, triphosgene) is entered into a polycondensation reaction with synthesized di-p-toluenesulfonic acid salt of a bis-(α-amino acid)-alkylene diester to obtain the final polymer having both ester and urea bonds.

The unsaturated PEUs can be prepared by interfacial solution condensation of di-p-toluenesulfonate salts of bis-(α-amino acid)-alkylene diesters, comprising at least one double bond in $R^4$. Unsaturated diols useful for this purpose include, for example, 2-butene-1,4-diol and 1,18-octadec-9-en-diol. Unsaturated monomer can be dissolved prior to the reaction in alkaline water solution, e.g. sodium hydroxide solution. The water solution can then be agitated intensely, under external cooling, with an organic solvent layer, for example chloroform, which contains an equimolar amount of monomeric, dimeric or trimeric phosgene. An exothermic reaction proceeds rapidly, and yields a polymer that (in most cases) remains dissolved in the organic solvent. The organic layer can be washed several times with water, dried with anhydrous sodium sulfate, filtered, and evaporated. Unsaturated PEUs with a yield of about 65%-85% can be dried in vacuum, for example at about 45° C.

To obtain a porous, strong material, L-Leu based PEUs, such as 1-L-Leu-4 and 1-L-Leu-6, can be fabricated using the general procedure described below. Such procedure is less successful in formation of a porous, strong material when applied to L-Phe based PEUs.

The reaction solution or emulsion (about 100 mL) of PEU in chloroform, as obtained just after interfacial polycondensation, is added dropwise with stirring to 1,000 mL of about 80° C.-85° C. water in a glass beaker, preferably a beaker made hydrophobic with dimethyldichlorsilane to reduce the adhesion of PEU to the beaker's walls. The polymer solution is broken in water into small drops and chloroform evaporates rather vigorously. Gradually, as chloroform is evaporated, small drops combine into a compact tar-like mass that is transformed into a sticky rubbery product. This rubbery product is removed from the beaker and put into hydrophobized cylindrical glass-test-tube, which is thermostatically controlled at about 80° C. for about 24 hours. Then the test-tube is removed from the thermostat, cooled to room temperature, and broken to obtain the polymer. The obtained porous bar is placed into a vacuum drier and dried under reduced pressure at about 80° C. for about 24 hours. In addition, any procedure known in the art for obtaining porous polymeric materials can also be used.

Properties of high-molecular-weight porous PEUs made by the above procedure yielded results as summarized in Table 1.

Tensile strength of illustrative synthesized PEUs was measured and results are summarized in Table 2. Tensile strength measurement was obtained using dumbbell-shaped PEU films (4×1.6 cm), which were cast from chloroform solution with average thickness of 0.125 mm and subjected to tensile testing on tensile strength machine (Chatillon TDC200) integrated with a PC using Nexygen FM software (Amtek, Largo, Fla.) at a crosshead speed of 60 mm/min. Examples illustrated herein can be expected to have the following mechanical properties:

1. A glass transition temperature in the range from about 30° C. to about 90° C., for example, in the range from about 35° C. to about 70° C.;

2. A film of the polymer with average thickness of about 1.6 cm will have tensile stress at yield of about 20 Mpa to about 150 Mpa, for example, about 25 Mpa to about 60 Mpa;

3. A film of the polymer with average thickness of about 1.6 cm will have a percent elongation of about 10% to about 200%, for example about 50% to about 150%; and 4. A film of the polymer with average thickness of about 1.6 cm will have a Young's modulus in the range from about 500 MPa to about 2000 MPa. Table 2 below summarizes the properties of exemplary PEUs of this type.

TABLE 2

Mechanical Properties of PEUs

| Polymer designation | $Tg^{a)}$ (° C.) | Tensile Stress at Yield (MPa) | Percent Elongation (%) | Young's Modulus (MPa) |
|---|---|---|---|---|
| 1-L-Leu-6 | 64 | 21 | 114 | 622 |
| $[1\text{-L-Leu-6}]_{0.75}$-$[1\text{-L-Lys(OBn)}]_{0.25}$ | 34 | 25 | 159 | 915 |

The various components of the invention composition can be present in a wide range of ratios. For example, the ratio of polymer repeating unit to bioactive agent is typically 1:50 to 50:1, for example 1:10 to 10:1, about 1:3 to 3:1, or about 1:1. However, other ratios may be more appropriate for specific purposes, such as when a particular bioactive agent is both difficult to incorporate into a particular polymer and has a low activity, in which case a higher relative amount of the bioactive agent is required.

TABLE 1

Properties of PEU Polymers of Formula (VI) and (VII)

| PEU* | Yield [%] | $\eta_{red}{}^{a)}$ [dL/g] | $M_w{}^{b)}$ | $M_n{}^{b)}$ | $M_w/M_n{}^{b)}$ | $Tg^{c)}$ [° C.] | $T_m{}^{c)}$ [° C.] |
|---|---|---|---|---|---|---|---|
| 1-L-Leu-4 | 80 | 0.49 | 84000 | 45000 | 1.90 | 67 | 103 |
| 1-L-Leu-6 | 82 | 0.59 | 96700 | 50000 | 1.90 | 64 | 126 |
| 1-L-Phe-6 | 77 | 0.43 | 60400 | 34500 | 1.75 | — | 167 |
| $[1\text{-L-Leu-6}]_{0.75}$-$[1\text{-L-Lys(OBn)}]_{0.25}$ | 84 | 0.31 | 64400 | 43000 | 1.47 | 34 | 114 |
| 1-L-Leu-DAS | 57 | 0.28 | $55700^{d)}$ | $27700^{d)}$ | $2.1^{d)}$ | 56 | 165 |

*PEUs of general formula (VI), where,
1-L-Leu-4: $R^4 = (CH_2)_4$, $R^3 = i\text{-}C_4H_9$
1-L-Leu-6: $R^4 = (CH_2)_6$, $R^3 = i\text{-}C_4H_9$
1-L-Phe-6: $R^4 = (CH_2)_6$, $R^3 = -CH_2-C_6H_5$
1-L-Leu-DAS: $R^4 = $ 1,4:3,6-dianhydrosorbitol, $R^3 = i\text{-}C_4H$
$^{a)}$Reduced viscosities were measured in DMF at 25° C. and a concentration 0.5 g/dL;
$^{b)}$GPC Measurements were carried out in DMF, (PMMA);
$^{c)}$Tg taken from second heating curve from DSC Measurements (heating rate 10° C./min);
$^{d)}$GPC Measurements were carried out in DMAc, (PS).

As used herein "dispersed" means a molecule, such as an bioactive agent, as disclosed herein, is mixed, or dissolved in, homogenized with, or covalently or non-covalently bound to the linear polymer If more than one bioactive agent is desired, multiple bioactive agents may be dispersed in individual polymers and then mixed as needed to form the final composition, or the bioactive agents may be mixed together and then dispersed into a single polymer that is used as the linear polymer in the invention compositions.

Optionally, the articles of manufacture, e.g., internal fixation devices and other surgical implants, can further comprise a thin covering of the linear polymer to aid in control of their biodegradation and release rates.

For example, The PEA, PEUR and PEU polymers described herein readily absorb water (5 to 25% w/w water up-take, on polymer film), allowing hydrophilic molecules, such as many biologics, to readily diffuse through them. This characteristic makes PEA, PEUR and PEU polymers suitable for use as an over coating on articles of manufacture made thereof to control release rate of any dispersed bioactive agent(s). Water absorption also enhances biocompatibility of the polymers and the articles of manufacture based on such polymers.

An invention elastomeric composition, or an article of manufacture made thereof, when made of a biodegradable linear polymer, may degrade over a time dependent upon a variety of factors, such as type and relative proportions of the linear polymer and the cross-linker, the degree of polymerization (e.g., whether both the linear polymer and the cross-linker are polymerized) and the dimensions of an article of manufacture made thereof. However, due to the great variety of chemical structures that can be employed in the invention compositions, it is contemplated that the composition will degrade over a time from about 30 days to about 24 months, or longer. Biodegradable linear polymers with longer time spans or the use of non-degradable polymers are particularly suitable for providing an implantable device that remains effective for its structural, therapeutic or diagnostic purpose for a sufficient time to eliminate the need to replace the device.

Rate of release of the bioactive agent from the compositions described herein can be controlled by adjusting such factors as the coating thickness, number of bioactive agent molecules covering the exterior of the article or device, and density of the coating. Density of the coating can be adjusted by adjusting loading of the bioactive agents, if any, in the coating. When the coating contains no bioactive agent, the polymer coating is most dense, and the bioactive agent elutes through the coating most slowly. By contrast, when bioactive agent is loaded into the coating, the coating becomes porous once the bioactive agent has eluted out, starting from the outer surface of the coating and, therefore, the bioactive agent at the center of the particle can elute at an increased rate. The higher the loading in the covering, the lower the density of the coating layer and the higher the elution rate.

Once the composition is assembled using the invention methods, as below, the composition can be formulated for subsequent delivery. For example, for injection, the compositions will generally include one or more "pharmaceutically acceptable excipients or vehicles" appropriate for in vivo delivery, such as water, saline, glycerol, polyethyleneglycol, hyaluronic acid, ethanol, and the like. Additionally, auxiliary substances, such as wetting or emulsifying agents, pH buffering substances, and the like, may be present in such vehicles.

For a further discussion of appropriate vehicles to use for particular modes of delivery, see, e.g., *Remington: The Science and Practice of Pharmacy*, Mack Publishing Company, Easton, Pa., 19th edition, 1995. One of skill in the art can readily determine the proper vehicle to use for the particular composition and site of implant.

Methods of Using the Invention Compositions

The compositions contain free-radical polymerizable groups that, when polymerized, crosslink the compositions to form either semi-interpenetrating networks or polymer networks. The invention compositions can be polymerized ex vivo to form solid articles for implantation, or can be polymerized in situ and used as bone cement or, in dental applications, to form artificial teeth or to replace or repair damaged bones, for example, the jawbone.

Ex Vivo Polymerization: When the invention composition is polymerized ex vivo, the viscosity of the composition is preferably that of an injectable paste or a liquid, such that the material can be molded to a desired shape and the cross-linkers can be crosslinked. Suitable shapes include screws, pins, vascular stents, hollow tubes, shunts, and the like. In this embodiment, a solution or dispersion of the composition can be cast onto a flat or molded surface or injected into any appropriate mold, for example in the shape of a tooth or bone segment or in the shape of a desired surgical implant, such as a screw, rod, plate or disc. The semi-interpenetrating polymer network formed after the monomers and/or macromers are polymerized will retain the shape of the surface or mold. The solvent is then evaporated from the composition over a period of time, for example, 24 hours at room temperature. Any residual solvent can be removed subsequently by lyophilization of the composition.

In Situ Polymerization: For certain applications when the composition is to be polymerized in situ, the composition is formulated as a fluid having sufficient viscosity to be injectable. Following injection into a site in a subject, the composition can be crosslinked to form a solid interpenetrating polymer network. In this embodiment, the composition can be used as a bulking agent for hard tissue defects, such as bone or cartilage defects. Examples of this application include injection of the invention composition into a subdural area surrounding the skull (e.g., the face) where a bony deformity exists secondary to trauma. In the case of complex fractures of long bones, such as the femur or tibia, the invention composition can be injected into the bone or area of bone loss or fragmentation. Alternatively, the invention composition can be used in constructive surgery intended to compensate for a malformation or to augment an existing bony formation to achieve a desired aesthetic goal. The injection in these instances can be made directly into the needed area by needle or syringe while the subject being treated is under local or general anesthesia. For use in dental applications, the viscosity of the composition is that of a paste thick enough to maintain a desired shape when applied to the surface of a broken tooth such that the composition will harden into the desired shape when polymerized. The viscosity of the composition can be adjusted by adding appropriate viscosity modifying agents as described herein.

In addition to treatment of humans, the invention polymer particle delivery compositions are also intended for use in veterinary treatment of a variety of non-human subjects, such as pets (for example, cats, dogs, rabbits, and ferrets), farm animals (for example, poultry, swine, horses, mules, dairy and meat cattle) and race horses.

Methods of Polymerizing the Composition

The composition can be polymerized using one or more suitable free-radical, i.e., active species, initiators. For example, photo-initiators and thermally activatable initiators are used for polymerization of the invention composition in a concentration not toxic to cells, such as less than 1% by weight of the composition, more preferably between 0.05 and 0.01% by weight of initiator in the composition.

The free radical polymerizable groups in the composition can be polymerized using photo-initiators that generate active species upon exposure to electromagnetic radiation, such as UV light, or, preferably, using long-wavelength ultraviolet light (LWUV) or visible light, for example, by photon absorption of certain dyes and chemical compounds. LWUV and visible light are preferred because they cause less damage to tissue and other biological materials than UV light. Useful photo-initiators are those which can be used to initiate polymerization of the macromers without cytotoxicity and within a short time frame, minutes at most and most preferably seconds.

Exposure of dyes as photo-initiators and co-catalysts, such as amines, to visible or LWUV light can generate active species. Light absorption by the dye causes the dye to assume a triplet state, and the triplet state subsequently reacts with the amine to form an active species that initiates polymerization. Polymerization can be initiated by irradiation with light at a wavelength of between about 200-700 nm, most preferably in the long wavelength ultraviolet range or visible range, 320 nm or higher, and most preferably between about 365 and 514 nm.

Numerous dyes can be used as initiators for photo-polymerization. Suitable dyes for use in practice of this invention are well known to those of skill in the art and include, but are not limited to erythrosin, phloxime, rose bengal, thionine, camphorquinone, ethyl eosin, eosin, methylene blue, riboflavin, 2,2-dimethyl-2-phenylacetophenone, 2-methoxy-2-phenylacetophenone, 2,2-dimethoxy-2-phenyl acetophenone, other acetophenone derivatives, and camphorquinone. Suitable photo-initiators also include such compounds as diphenyl(2,4,6-trimethylbenzoyl)-phosphine oxide (DAROCUR® TPO), 2-Hydroxy-2-methyl-1-phenyl-1-propanol (DAROCUR® 1173), and 2,2-Dimethoxy-2-phenylacetophenone (DMPA), and the like. Suitable co-catalysts for use in practice of the invention include amines, such as N-methyl diethanolamine, N,N-dimethyl benzylamine, tri ethanol amine, triethylamine, dibenzyl amine, N-benzylethanolamine, N-isopropyl benzylamine, and the like. Triethanolamine is a preferred co-catalyst.

As used herein, the term "electromagnetic radiation" means energy waves of the electromagnetic spectrum including, but not limited to, x-ray, ultraviolet, visible, infrared, far infrared, microwave and radio-frequency.

The term "visible light" as used herein refers to electromagnetic energy waves having a wavelength of at least approximately $4.0 \times 10^{-5}$ cm. The term "ultraviolet light" as used herein refers to energy waves having a wavelength of at least approximately $1.0 \times 10^{-5}$ cm, but less than $4.0 \times 10^{-5}$ cm. "Blue light" as used herein refers to electromagnetic energy waves having a wavelength of at least approximately $4.5 \times 10^{-5}$ cm, but less than $4.9 \times 10^{-5}$ cm.

"Radiation source" as used herein means a source of electromagnetic waves in wavelengths as defined above. Exemplary radiation sources include, but are not limited to, lamps, the sun, blue lamps, and ultraviolet lamps. Such electromagnetic waves can be transmitted to the cross-linkable composition either directly or by means of a fiber optic catheter, or other light transmission device, for in vivo cross-linking.

The depth of penetration can be controlled by the wavelength of the light used to cause the photo-polymerization. For example, visible light penetrates deeper through tissue than UV light. Penetration through tissue can range from a few microns to one cm, with one cm of penetration being common with visible light, Radiation with a wavelength between 200 and 700 nm is optimum to creating active species and polymerize the network.

Preferably, when the crosslinking occurs in vivo, the polymerization conditions are mild enough not to damage surrounding tissue. Although discussed herein principally with regard to administration of a light source external to the skin, the above described conditions are applicable to light applied through tissues, for example, from a catheter in a blood vessel adjacent to where the composition has been injected, or in the space adjacent to a bone to be repaired.

Suitable thermally activatable organic and inorganic initiators include various peroxides, peroxyacids, potassium persulfate, azoinitiators-azobisisobutyronitrile (AIBN), 4,4-azobis(4-cyanovaleric acid), and their organic or water solutions.

The invention compositions can be polymerized ex vivo to provide solid articles of manufacture, such as internal fixation devices. For example, vascular stents, pins and screws, surgical plates, sutures, and the like, which can be used to repair arterial blockage and broken bones, for bone and tooth replacement inserts, and the like, can be fabricated using methods of polymer fabrication well known in the art. Alternatively, the compositions can be injected as a viscous liquid or placed at a desired site as a thick putty and then polymerized in situ to function as bone cement, tooth repair, and the like. For those areas that can be accessed via injection, the composition is preferably fluid when applied (i.e. the cross-linkers are not polymerized), and an elastomeric solid when polymerized.

The invention compositions can be implanted using standard surgical techniques, for example for repair or replacement of bone or tooth, insertion of arterial stents, and the like. The composition can be directly implanted into the site where bone growth or tooth repair is desired. In one embodiment, the composition can be pre-cast or molded into a desired shape as an internal fixation device for repair of a bone, bony defect, or bone segment, in need thereof. The internal fixation device so fabricated is then surgically implanted using standard surgical procedures. Alternatively, a vascular stent can be implanted using surgical techniques well known in the art. In one embodiment, the composition used to manufacture the vascular stent is polymerized in situ to provide ease of insertion and strength post implacement.

The linear polymer preferably constitutes between 10 and 90% by weight of the composition, more preferably between 30 and 70% of the composition. The crosslinked polymer preferably constitutes between about 30 and 70% by weight of the semi-interpenetrating network composition, more preferably, between 40 and 60 percent of the composition, with the balance being initiators, excipients, therapeutic agents, and other components. The invention elastomeric compositions form semi-interpenetrating polymer networks when these components are mixed, and the crosslinkable component is crosslinked.

The following examples are meant to illustrate, and not to limit, the invention.

Example 1

Synthesis of Ester Type Di-Functional Cross-Linkers (ESC-2)

Though ester type di-functional cross-linkers ESC-2, for example, 1,4-butanediol di-acrylate, 1,4-butanediol di-methacrylate, 1,6-hexanediol di-acrylate and 1,6-hexanediol di-methacrylate, are commercially available products, the development of new approaches to synthesis of pure products is desirable for use in preparing new formulations. Especially desirable is development of a convenient method of acylating hydroxyl-groups using unsaturated acid chlorides under mild conditions without generation of free radicals to avoid undesirable premature polymerization of intended products.

In a typical acylation procedure, 10 g of diol was dissolved in 100 mL of DMA, the solution was chilled to 0° C., acryloyl chloride (1.1 mole per each mole of OH-groups) was added stepwise, keeping the temperature 0-5° C. After the whole amount of acid chloride had been added, stirring was continued at room temperature for 24 hours. The reaction mixture (in some cases a white paste-like mass) was then poured into water. The two-layer system obtained was placed into a separating funnel, the organic layer was collected, repeatedly washed with $NaHCO_3$ (5%) solution in water and then with water, dried over molecular sieves 4A and kept in a refrigerator. The yields and characteristics of some new ESC-2 type cross-linkers prepared by this general method are summarized in Table 3 below.

TABLE 3

Water-insoluble ester-type cross-linkers (ESC) of Formula (X)

| Compound[1] ESC-2 | | Yield, | Refractive Index, $n_D$ Found | Solubility | | |
|---|---|---|---|---|---|---|
| # | $(CH_2)_n$—$R^7$ | [%] | Lit. data | Chloroform | Ethanol | Acetone |
| 1 | 3-AA | 94 | 1.4528 N.F. | + | + | + |
| 2 | 4-AA | 92 | 1.4552 1.4560 | + | + | + |
| 3 | 6-AA | 90 | 1.4515 1.4560 | + | + | + |

[1]Designations: 3 = 1,3-propanediol; 4 = 1,4-butanediol; 6 = 1,6-hexanediol; AA = acryloyl.

Example 2

Synthesis of Water Soluble Ester Type Bi-Functional Cross-Linkers (WSEC-2) Based on Maleic Acid This example illustrates a general procedure for synthesis of water soluble ester type bi-functional cross-linkers (WSEC-2). A mixture of 0.05 mole of fatty diol, 10.0 g (0.1025 mole, slight excess) of maleic anhydride, 0.19 g (0.001 mole) of p-toluenesulfonic acid monohydrate in 200 mL of benzene was refluxed for 8 hours. The reaction mixture was cooled to room temperature and a precipitated white solid was filtered off, dried, and recrystallized from benzene. The yields and characteristics of some new WSEC-2 type cross-linkers prepared by this method are summarized in Table 4 below.

TABLE 4

Water soluble ester type bi-functional cross-linkers (WESC-2) of Formula (X)

| Compound[1] ESC-2 | | | | Gross Formula | Solubility | | | |
|---|---|---|---|---|---|---|---|---|
| # | $(CH_2)_n$—$R^7$ | Yield | Mp [° C.] | (Mol Weight) | $H_2O$ pH > 7 | $CHCl_3$ | Ethanol | Acetone |
| 1 | 3-MLA | 38 | 113-115 | $C_{11}H_{12}O_8$ (272.21) | + | − | + | + |
| 2 | 4-MLA | 75 | 91-93 | $C_{12}H_{14}O_8$ (286.23) | + | + | + | + |
| 3 | 6-MLA | 78 | 104-106 | $C_{14}H_{18}O_8$ (314.29) | + | + | + | + |
| 4 | 8-MLA | 89 | 93-95 | $C_{16}H_{22}O_8$ (342.34) | + | + | + | + |
| 5 | PER-MLA (WESC-4) | Insol. gel | | $C_{21}H_{20}O_{16}$ (528.37) | − | − | − | − |

[1]Designations: 3 = 1,3-propanediol; 4 = 1,4-butanediol; 6 = 1,6-hexanediol; 8 = 1,8-octanediol; PER = pentaerythritol; MLA = maleinyl.

Example 3

Diamine Type Non-Photoreactive Cross-Linkers

Synthesis of acid salts of bis(α-amino acid) ester. Synthesis of acid salts of bis(α-amino acid)-diol-diesters is disclosed in U.S. Pat. No. 6,503,538 B1. Procedures were carried out according to Scheme 3.

An exemplary synthesis of Di-p-toluenesulfonic acid salt of bis-L-leucine-hexane-1,6-diester is as follows: L-Leucine (0.132 mol), p-toluenesulfonic acid monohydrate (0.132 mol) and 1,6-hexane diol (0.06 mol) in 250 mL of toluene were placed in a flask equipped with a Dean-Stark apparatus and overhead stirrer. The heterogeneous reaction mixture was heated to reflux for about. 12 hours until 4.3 mL (0.24 mol) of water evolved. The reaction mixture was then cooled to room temperature, filtered, washed with acetone, and recrystallized twice from methanol/toluene (2:1 mixture). Yields and melting points of monomer salts were identical to published data (Katsarava et al. *J. Polym. Sci. Part A: Polym. Chem.* (1999) 37. 391-407).

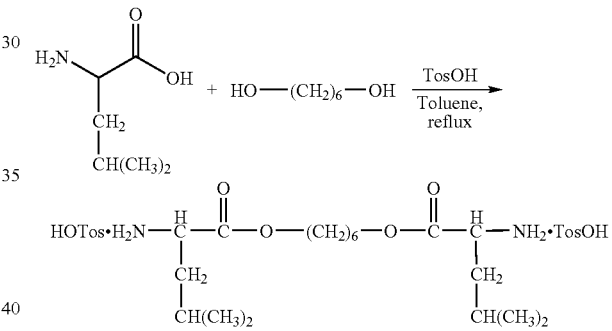

Scheme 3

Free bases from corresponding di-tosilate salts were separated according to Scheme 4:

Scheme 4.

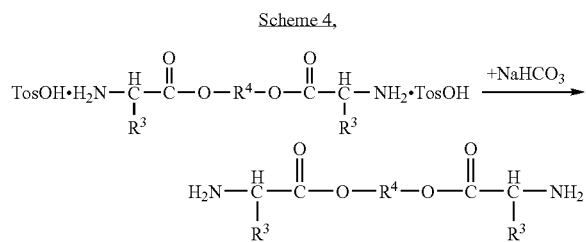

wherein, $R^3=CH_2C_6H_5$, (L-Phe), or $CH_2CH(CH_3)_2$, (L-Leu); and $R^4$: $6=(CH_2)_6$; $8=(CH_2)_8$, or $12=(Cl_2)_{12}$.

General procedure for preparation of free diamines (Scheme 4): In a typical procedure, 0.1 mole of di-p-toluenesulfonic acid salt of bis-(α-amino acid)-α,ω-alkylene diester was dissolved into 500 mL of the 0.21 mole of $Na_2CO_3$ water solution and stirred for 10 hours. Then the bi-layer reaction mixture was kept in a refrigerator overnight to allow the oily product to harden into a tar-like mass. The aqueous layer was decanted and the tar-like mass (free diester-diamine) was washed with distilled water at room temperature. Under these conditions the tar-like mass became oily again. After being returned to the refrigerator, the mass hardened again, water was decanted, and the obtained product dried in vacuum at room temperature over NaOH. The yields of obtained grease-like products are summarized in Table 5 below.

TABLE 5

Yields of bis-α-aminoacyl diols (free bases, scheme 4)

| # | Bis-α-aminoacyl-diol | Yield, in % |
| --- | --- | --- |
| 1 | Leu-6,b | 52 |
| 2 | Leu-8,b | 47 |
| 3 | Leu-12,b | 84 |
| 4 | Phe-6,b | 63 |
| 5 | Phe-8,b | 49 |
| 6 | Phe-12,b | 44 |

The FTIR spectra of the above bis-α-aminoacyl diols, which were greased onto NaCl plates as thin films, are shown in FIG. 1. Strong absorption maxima in the region 3200-3400 $cm^{-1}$ (for $NH_2$) and 1730-1740 $cm^{-1}$ (for ester CO) is consistent with the assumed structure. However, the complexity of the absorption bands at 3200-3400 $cm^{-1}$ and peaks in the region 1650-1670 $cm^{-1}$ (amide CO+benzene ring in case of Phe-based compounds) indicates self-condensation of the obtained di-amino-diesters with a certain extent of amide links formed.

Example 4

The obtained bis-α-aminoacyl diols were used as cross-linking agents for curing unsaturated PEAs (of Formula I) composed of fumaric acid and epoxy-PEAs composed of epoxy-succinic acid. For this curing reaction, 100 mg of PEA was dissolved in 2 mL of chloroform, 20 mg (20 weight %) of di-amino-diester was added to the solution and the solution was cast onto a hydrophobic surface. Chloroform was evaporated under atmospheric conditions up to dryness and the films obtained were kept at room temperature for a week. Then the films were placed again in 2 mL of chloroform at room temperature. The films became insoluble in chloroform (only swelled), which confirms the polymer network formation.

Lipase catalyzed in vitro biodegradation of cross-linked epoxy-PEA: In vitro biodegradation of PEA of Formula I based on trans-epoxy-succinic acid, L-phenylalanine and 1,6-hexanediol: (Poly-t-ES-Phe-6) was cross-linked with various concentrations of Phe-6,b. Studies were conducted to determine the effect of concentration of the cross-linker upon rates of biodegradation of the invention composition. The films used for this study weighed 400 mg each, and contained 5%, 10% or 30% of the cross-linker. The following weight ratios polymer to crosslinker were used in preparation of the films:

Control, 400 mg of t-ES-Phe-6 polymer: with 0% diamine,
5% w/w diamine: 380 mg of t-ES-Phe-6+20 mg of Phe6,b
10% w/w diamine: 360 mg of t-ES-Phe-6+40 mg of Phe6,b
30% w/w diamine: 280 mg of t-ES-Phe-6+120 mg of Phe6, b.

The general procedure is as follows: The predetermined quantity of the polymer was dissolved in 7 mL of chloroform using a magnetic stirrer and the predetermined quantity of crosslinker was added to the polymer solution. The mixture was stirred for an additional 5 hours and the obtained emulsion (crosslinker is not soluble in chloroform) was cast onto Teflon® treated dishes of 4 cm diameter. Chloroform was evaporated at room temperature for 24 hours, films were dried at 50° C. for 5 hours, and then placed into a thermostat-controlled environment at 37° C. for 24 hours before the degradation experiments were started. Crosslinked films were checked for solubility in chloroform to make sure they were crosslinked. Dry films were placed in PBS containing 4 mg of lipase (Sigma Chemicals). After certain time films were removed from the PBS-enzyme solution, washed with distilled water, dried up to constant weight at 50° C. and weighed to determine the weight-loss in mg per square centimeter of the film surface ($Mg/cm^2$).

Figure 2:
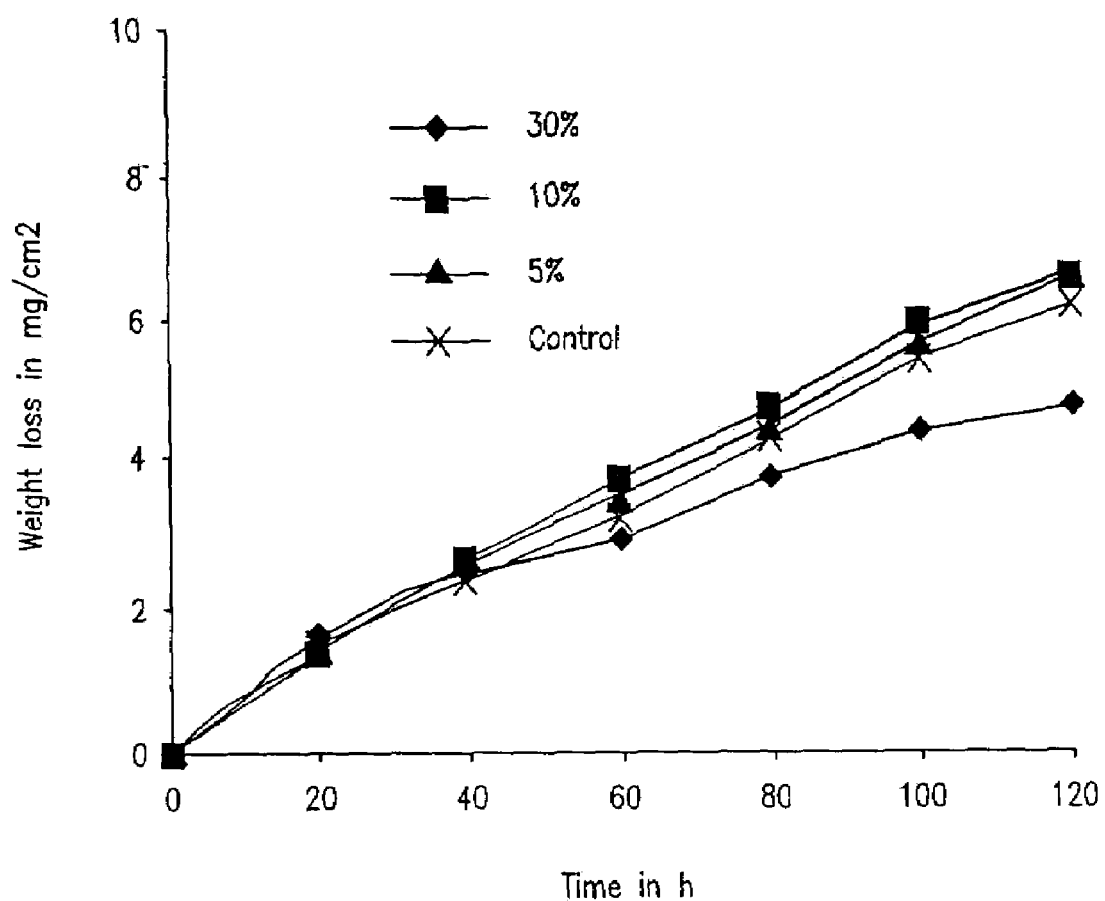
FIG. 2 is a graph showing lipase catalyzed in vitro biodegradation of epoxy-PEA composed of trans epoxy-succinic acid and Phe-6 (t-ES-Phe-6) and cross-linked with various quantities of a free base (Phe-6,b) prepared according to Scheme 4 wherein $R^4=(CH_2)_6$.
Figure 3:
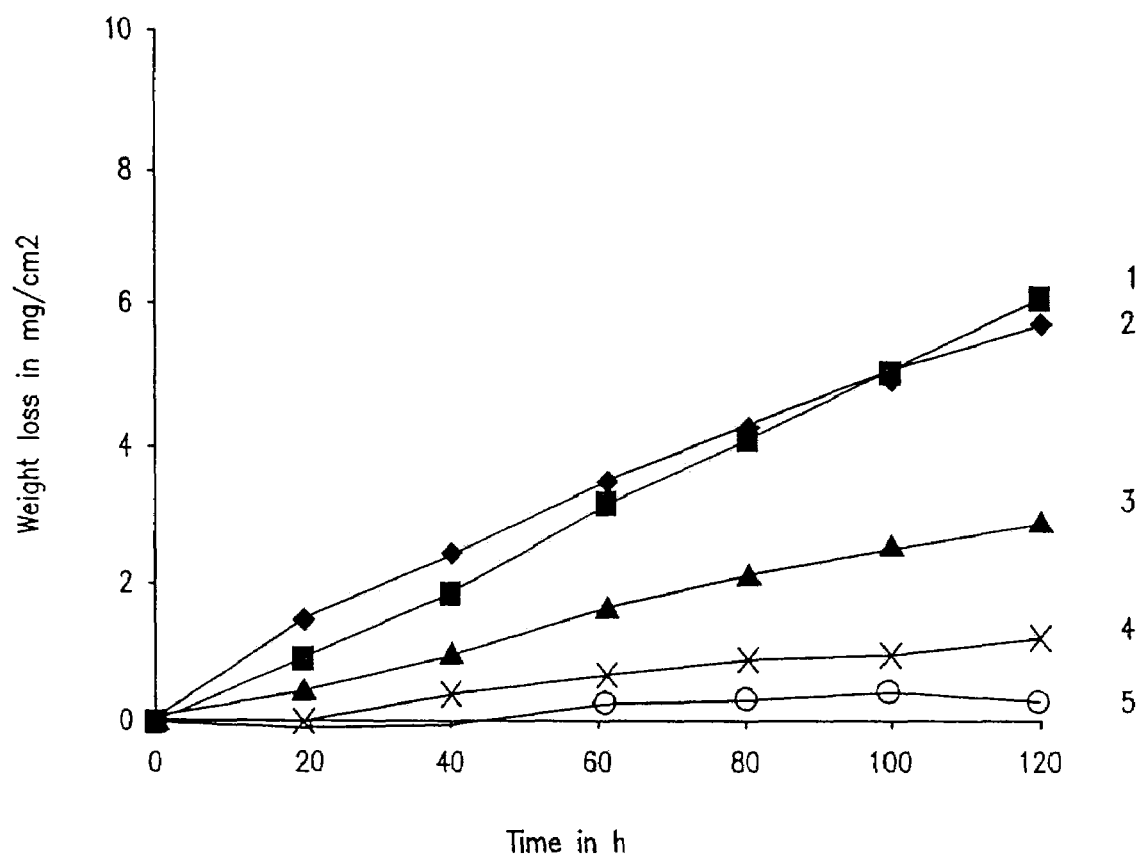
FIG. 3 is a graph showing lipase catalyzed in vitro biodegradation of epoxy-PEA (composed of trans-epoxy-succinic acid and Phe-6 (t-ES-Phe-6)), which was cross-linked thermally at 120° C. for from 1 to 24 hours: 1=1 hour, 2=control film, i.e. without thermal exposure, 3=6 hours, 4=12 hours, and 5=24 hours of thermal exposure.

The results are represented graphically in FIG. 2. As can be seen from these data, the chemical cross-linking with biodegradable cross-linkers only slightly influences biodegradation of the PEA: the weight-loss rates for the 5% and 10% crosslinked films are very close to each other and close to the weight-loss rate of the control film (not-crosslinked). Only the film containing 30% cross-linker showed a somewhat lower biodegradation rate than the control. These data are contrary to the data obtained for thermally crosslinked films (FIG. 3), for which the higher the content of cross-linker, the lower the rate of weight-loss of the PEA (except for the film cross-linked for only one hour, the biodegradation rate of which was virtually the same as the biodegradation rate of the control film).

Example 5

Synthesis of Ester-Amide Type Photo Cross-Linkers (EACs)

For synthesis of ester-amide type cross-linkers, interfacial condensation of di-p-toluenesulfonic acid salts of bis-(α-amino acid) α,ω-alkylene diesters with unsaturated acid chlorides was used. The product EACs retained solubility in organic solvents.

Synthesis of di-functional ester-amide type cross-linkers EAC-2: In the general procedure for synthesis of EAC-2s, two separate solutions were prepared prior to the synthesis reaction:

1. Solution A: 0.005 mole of di-p-toluenesulfonic acid salt of bis-(α-amino acid) α,ω-alkylene diester (prepared as described in U.S. Pat. No. 6,503,538) and 2.12 g (0.02 mole) of $Na_2CO_3$ were placed into 300 mL flask and 60 mL of water was added. After complete dissolution of the solid, the obtained solution was chilled to 0-5° C.

2. Solution B: 0.011 mole of unsaturated acid (acryloyl, methacryloyl or cinnamoyl) chloride was dissolved in 30 mL of chloroform (or in methylene chloride).

3. Solution B was added drop-wise to chilled Solution A while the reaction temperature was maintained between 0-5° C. and the combination was shaken vigorously after each portion of the Solution B was added. After addition of the last portion of Solution B, the reaction solution was shaken for additional 30 min. The obtained two-phase reaction mixture was placed into a separating funnel, an organic phase was collected, and chloroform was evaporated therefrom to dryness. If the obtained product was crystalline, the product was recrystallized from an ethanol/water mixture. If the product was amorphous, the product was dissolved in ethanol, precipitated by addition of water, and the obtained white solid was recrystallized from an ethanol/water mixture. The yields and characteristics of new EAC-2 type cross-linkers obtained by this method are given in Table 6 herein,

Example 6

This example illustrates synthesis of exemplary water insoluble ester-amide type cross-linkers EAC-4 and EAC-P.

Method of Synthesis for EAC-4

Synthesis of tetra-p-toluenesulfonic acid salt of tetrakis-(L-phenylalanine)-2,2-bis-hydroxymethyl-1,3-propanediol tetraester (Phe-PER): 3.40 g (0.025 mole) of pentaerytritol (PER), 18.17 g (0.11 mole) of L-phenylalanine, and 20.92 g (0.11 mole) of p-toluenesulfonic acid monohydrate were placed into a 500 mL three-necked flask equipped with Dean-Stark trap, 250 mL of toluene was added, and the mixture was stirred. The reaction mixture was refluxed for 32 hours and liberated water was collected in the Dean-Stark condenser. In the first stage, the reaction proceeded homogeneously. After about 9 hours of this procedure, a solid product was formed. After removal of a theoretical amount of water, the obtained glassy solid was filtered, dried in vacuum, and the product was dissolved in an added mixture of isopropyl alcohol (20 mL) and diethyl ether (ca. 20 mL). A white crystalline product precipitated from the solution was filtered off and dried. Yield of tetra-p-toluenesulfonic acid salt of tetrakis-(L-phenylalanine)-2,2-bis-hydroxymethyl-1,3-propanediol tetraester (Phe-PER) was 60%, with a melting point of 151-154° C. Titration with 0.1 NaOH showed 4 moles of p-toluenesulfonic acid per 1 mole of the product obtained, thus confirming the formation of the tetrakis-derivative.

Synthesis of tetra-functional ester-amide type cross-linkers: The general method for preparation is illustrated by formation of Phe-PER-CA (Table 7, # 3) as follows: 2.83 g (0.002 mole) of Phe-PER and 1.69 g (0.016 mole) of $Na_2CO_3$ were placed in 300 mL flask, 90 mL of distilled water to form a solution was added and the solution was chilled to 0° C. To this chilled solution 1.34 g (0.0088 mole) of cinnamoyl chloride was added and stirred vigorously at 0° C. for 2 hours. The resulting reaction two-layer mixture was placed into a separating funnel and a chloroform layer was separated. After evaporation of chloroform the obtained solid product was washed with ethanol at room temperature on a glass filter and dried. The yield of Phe-PER-CA cross-linker was 41%, melting point was 232-236° C.; bromine number: calculated 51.39; found 52.91, which data confirms the assigned structure of the compound.

TABLE 6

Di-functional ester-amide type cross-linkers (EAC-2, Formula XIII)

| Compound Formula[1] EAC-2 $R^3$—$R^4$—$R^7$ | Yield in % | m.p., in ° C. | Bromine #, Found Calculated | Acid Number # Found calculated | Gross formula (mol. weight) | Elemental Analysis Found Calculated | | | Solubility | |
|---|---|---|---|---|---|---|---|---|---|---|
| | | | | | | C | H | N | Chloroform | Acetone |
| 1 Phe-4-AA | 81 | 96-97 | 68.36 64.96 | — | $C_{28}H_{32}N_2O_6$ (492.58) | 68.12 68.28 | 5.34 6.55 | 5.67 5.69 | + | + |
| 2 Phe-4-MA | 79 | 94-95 | 69.53 61.46 | — | $C_{30}H_{36}N_2O_6$ (520.63) | 68.97 69.21 | 6.76 6.97 | 5.240 5.38 | + | + |
| 3 Phe-4-CA | 78 | 145-146 | 63.50 61.46 | — | $C_{40}H_{40}N_2O_6$ (644.77) | 74.32 74.51 | 6.02 6.25 | 4.45 4.34 | + | + |
| 4 Phe-6-AA | 80 | 123-124 | 56.90 58.32 | — | $C_{30}H_{36}N_2O_6$ (520.63) | 69.35 69.21 | 6.68 6.97 | 5.65 5.38 | + | + |
| 5 Phe-6-MA | 76 | 83-85 | 47.76 49.63 | — | $C_{32}H_{40}N_2O_6$ (548.68) | 69.87 70.05 | 7.32 7.35 | 5.35 5.11 | + | + |
| 6 Phe-6-CA | 79 | 133-134 | 40.96 47.56 | — | $C_{42}H_{44}N_2O_6$ (672.83) | 74.86 74.98 | 6.35 6.59 | 4.26 4.16 | + | + |
| 7. Leu-4-AA | 85 | Tar | 76.81 75.38 | — | $C_{22}H_{36}O_6N_2$ (424.54) | 61.35 62.24 | 8.23 8.55 | 6.48 6.60 | + | + |
| 8. Leu-4-MA | 80 | 92-95 | 72.93 70.71 | — | $C_{24}H_{40}O_6N_2$ (452.59) | 63.56 63.69 | 8.67 8.91 | 6.03 6.19 | + | + |
| 9. Leu-4-CA | 81 | dec | 56.10 55.31 | — | $C_{34}H_{44}O_6N_2$ (576.74) | 70.14 70.81 | 7.57 7.69 | 4.76 4.86 | + | + |
| 10. Leu-6-AA | 85 | dec | 71.14 70.71 | — | $C_{24}H_{40}O_6N_2$ (452.59) | 62.78 63.69 | 8.46 8.91 | 6.53 6.19 | + | + |
| 11. Leu-6-MA | 85 | dec. | 72.25 70.84 | — | $C_{26}H_{44}O_6N_2$ (480.65) | 64.06 64.97 | 9.02 9.23 | 5.45 5.83 | + | + |
| 12. Leu-6-CA | 88 | dec. | 54.31 52.92 | — | $C_{36}H_{48}O_6N_2$ (604.79) | 69.34 71.50 | 7.62 8.00 | 4.14 4.63 | + | + |
| 13. Phe-4-MLA | 75 | dec. | | 204.65 193.25 | $C_{30}H_{32}N_2O_{10}$ (580.59) | 61.17 62.06 | 5.18 5.56 | 4.67 4.83 | + | + |

TABLE 6-continued

Di-functional ester-amide type cross-linkers (EAC-2, Formula XIII)

| Compound Formula[1] EAC-2 R³—R⁴—R⁷ | Yield in % | m.p., in °C. | Bromine #, Found Calculated | Acid Number # Found calculated | Gross formula (mol. weight) | Elemental Analysis Found Calculated | | | Solubility | |
|---|---|---|---|---|---|---|---|---|---|---|
| | | | | | | C | H | N | Chloroform | Acetone |
| 14. Phe-6-MLA | 81 | dec. | | 193.09 184.34 | $C_{32}H_{36}N_2O_{10}$ (608.65) | 62.24 63.15 | 5.49 5.96 | 4.24 4.60 | + | + |
| 15. Phe-6-MLA | 75 | dec. | | 199.32 207.54 | $C_{26}H_{40}N_2O_{10}$ (540.61) | 56.58 57.76 | 7.44 7.46 | 5.23 5.18 | + | + |

[1]Designations: 3 = 1,3-propanediol; 4 = 1,4-butanediol; 6 = 1,6-hexanediol; AA = acryloyl; MA = methacryloyl; CA = cinnamoyl, MLA = maleic acid; dec = decomposed (formed tar).

TABLE 7

Tetra-functional ester-amide type cross-linkers of Formula XV

| Compound Formula[1] EAC-4 | | Yield, | m.p., | Bromine #, Found[2] | Gross formula | Elemental Analysis Found Calculated | | | Solubility | | |
|---|---|---|---|---|---|---|---|---|---|---|---|
| # | R³—R⁶—R⁵ | in % | in °C. | Calculated | (mol. weight) | C | H | N | Chloroform | Ethanol | Acetone |
| 1 | Phe-PER-AA | 73 | 218-222 | 63.55 68.01 | $C_{53}H_{56}N_4O_{12}$ (941.05) | 67.45 67.65 | 6.18 6.00 | 6.06 5.95 | + | + | + |
| 2 | Phe-PER-MA | 66 | dec. | 59.25 64.18 | $C_{57}H_{64}N_4O_{12}$ (997.16) | 67.89 68.66 | 6.16 6.47 | 5.54 5.62 | + | + | + |
| 3 | Phe-PER-CA | 49 | 232-236 | 52.91 51.39 | $C_{77}H_{72}N_4O_{12}$ (1245.45) | 74.11 74.26 | 5.75 5.83 | 4.48 4.50 | + | − | + |
| 4 | Leu-PER-AA | 68 | 104-107 | 70.53 79.51 | $C_{41}H_{64}N_4O_{12}$ (804.98) | 60.28 61.18 | 7.82 8.01 | 6.40 6.96 | + | + | + |
| 5 | Leu-PER-MA | 56 | dec. | 79.53 74.32 | $C_{45}H_{72}N_4O_{12}$ (861.09) | 62.04 62.77 | 8.12 8.43 | 6.05 6.51 | + | + | + |
| 6 | Leu-PER-CA | 78 | 119-122 | 61.12 57.69 | $C_{65}H_{80}N_4O_{12}$ (1109.38) | 70.25 70.37 | 7.12 7.27 | 5.28 5.05 | + | − | + |

[1]Designations: 3 = 1,3-propanediol; 4 = 1,4-butanediol; 6 = 1,6-hexanediol; PER = pentaerythritol; AA = acryloyl; MA = methacryloyl; CA = cinnamoyl, MLA = maleic acid.
[2]Bromine number: a quantity of $Br_2$ in grams interacted with unsaturated bonds.

Example 7

Synthesis of Maleic Acid Based Water Soluble Ester-Amide Type Cross-Linkers (WEAC-2)

The general procedure for synthesis of a difunctional water soluble ester-amide cross-linker (WEAC-2) is as follows: 0.005 mole of di-p-toluenesulfonic acid salt of bis-(α-amino acid)-α,ω-alkylene diester and 1.53 mL (0.011 mole) of triethyl amine was dissolved in 30 mL of N,N-dimethylformamide (DMF) at room temperature under stirring. To the stirred solution 1.078 g (0.011 mole) of maleic anhydride was added stepwise keeping the reaction temperature at 25° C. (exothermic reaction). After the whole amount of maleic anhydride had been added, the reaction solution was stirred at room temperature for 1 hour. The resulting solution was poured into acidified (pH 1-2) water and the separated white solid product dried under reduced pressure over phosphorus pentoxide. The yields of new WEAC-2 type cross-linkers are found in Table 6, Compound #13-15.

Example 8

Polyamide (PA) Type Poly-Functional Cross-Linkers (EAC-PA)

Synthesis of Polyamide (PA) type poly-functional cross-linkers (EAC-PA) is illustrated by synthesis based on poly(N,N'-sebacoyl-L-lysine). EAC-PA was prepared by multi-step transformations of AABB type PAs as shown in reaction Scheme 3 below. In the first step lysine based PA (8-Lys(Bz)) was prepared by a procedure similar to that described in U.S. Pat. No. 6,503,538, applying the active polycondensation method. Polymer with carboxylic groups in pending chain later was obtained from corresponding benzyl ester by either catalytic hydrogenolysis using Pd/HCOOH or saponification of polyamide by ethanol solution of NaOH.

After deprotection of PA, poly-N,N'-sebacoyl-L-lysine (8-Lyz(H)) first transformed into corresponding poly-alcohol by interaction with di-ethanol amine, with subsequent acylation of the polyol (8-Lys-DEA) by unsaturated acid chlorides in DMA, as shown below (Scheme 5).

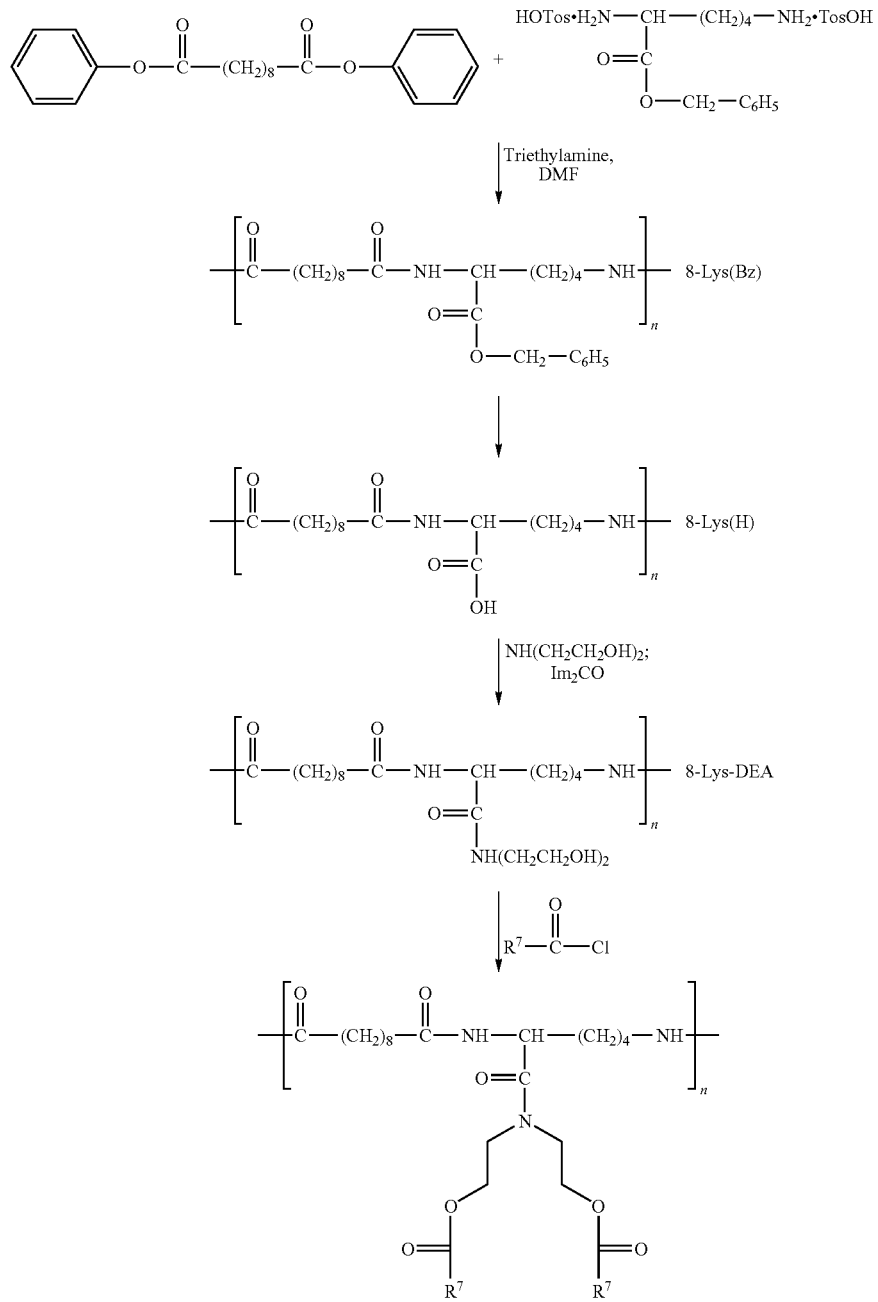

Where,

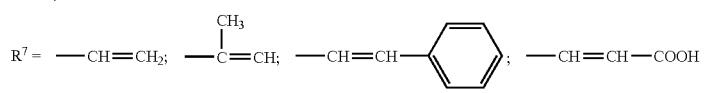

Figure 4:
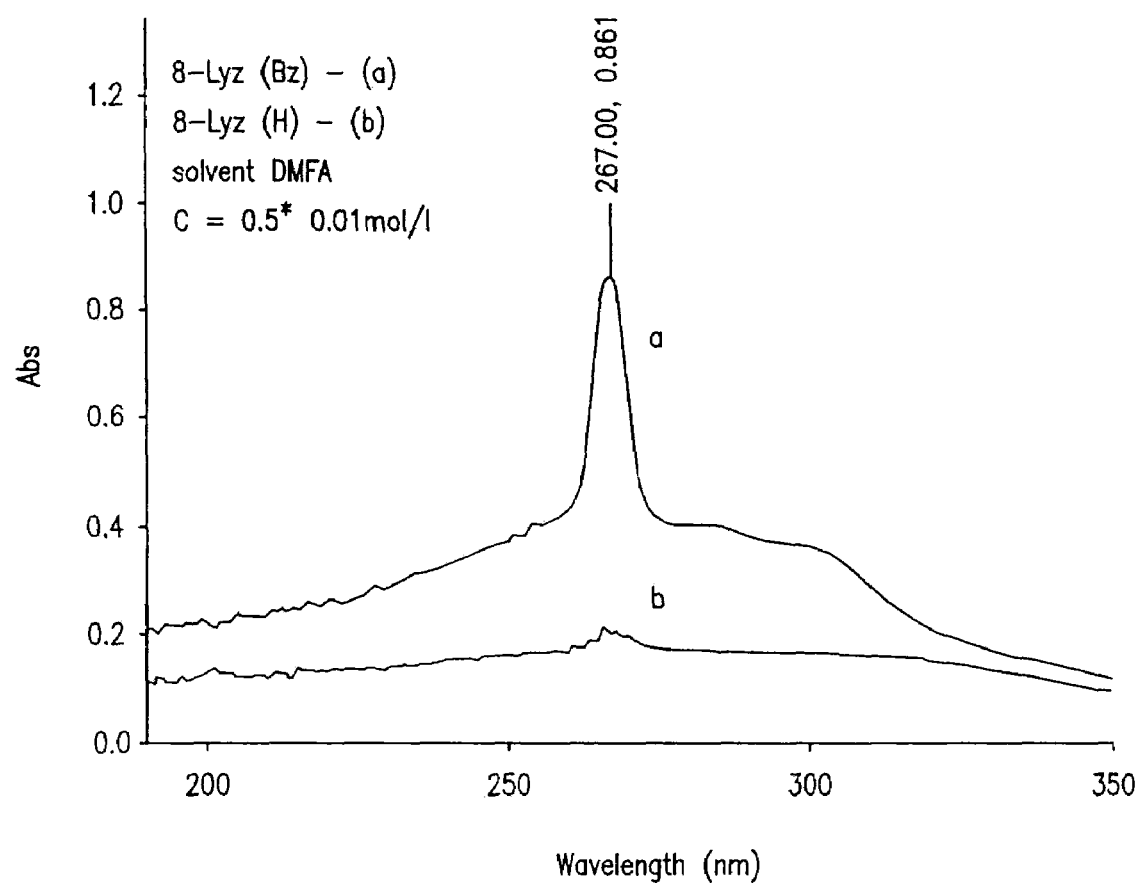
FIG. 4 is a trace of the UV-spectra in DMF of a polyamide (PA)-type poly-functional cross-linker before (a) and after (b) debenzylation obtained by saponification of 8-Lys(Bz), (scheme 5 herein).

In a typical procedure of saponification, 10 g of 8-Lys(Bz) was dissolved in 75 mL of DMSO and a solution of 2.88 g (0.072 mole) of NaOH in 26 mL of ethanol (95%) was added at room temperature. White product precipitated 10-15 minutes later. This product, which was sodium salt of 8-Lys(H), was dissolved in water and dialyzed against water until a neutral reaction of water in the outer zone was achieved. The resulting solution was acidified with hydrochloric acid to pH 2-3. A white plasto-elastic polymer precipitated, was filtered off and then dried until constant weight was reached. The degree of saponification (debenzylation), as determined by potentiometric titration, was 92%. Comparison of UV-spectras of the benzylated PA 8-K(Bz) and of polyacid 8-K shown in FIG. 4, in which very weak benzyl group absorbance at 167 nm indicates a high degree of debenzylation.

Conjugation of 8-Lys(H) with diethanolamine (synthesis of 8-Lys-DEA): Polyacid 8-Lys(H) (5 g) was dissolved in 50 mL of dry DMF under inert atmosphere. Then 2.6 g of N,N'-carbonyldiimidazole (Im$_2$CO) was added at room temperature and stirred for 40 min. To the resulting solution, 1.7 g of di-ethanolamine (DEA) was added and stirring continued for an additional 4 hours. The resulted polymer was separated from the reaction solution by precipitation in dry acetone, filtered off and dried. The obtained polyol 8-Lys-DEA with the yield of 91% was highly hygroscopic and soluble in water. UV-spectrum of polymer in DMF (FIG. 4) showed residual benzyl group absorbance as weak as in the case of 8-Lys(H). The residual carboxylic group content was determined by potentiometric titration, which indicated a degree of conversion of 87%.

Acylation of Poly-8-Lys-DEA with Unsaturated Acid Chlorides

Synthesis of Poly-8-Lys-DEA/MA: One g of poly-8-Lys-DEA was dissolved in 10 mL of dry N,N-dimethylacetamide (DMA) and 1 g (an excess) of methacryloyl chloride was added dropwise at 0-5° C. The resultant solution was stirred for 4 hours, then the temperature was raised to room temperature, and stirring continued for additional 20 hours. The solution was poured into water, the precipitated polymer was washed 5-6 times with NaHCO$_3$ (5%) water solution and then with water again. Polymer with lateral methacrylic moieties was dried at room temperature under reduced pressure. The yield was 89%. The degree of conversion of hydroxy groups achieved, as determined by bromine number, was 94%.

Synthesis of Poly-8-Lys-DEA/CA: The acylation of poly-8-Lys-DEA with cinnamoyl chloride was carried out under the same conditions as for 8-Lys-DEA/MA, above. The yield of final product achieved was 92%. The degree of conversion of OH-groups, as determined by bromine number, corresponded to 92% conversion. Thus, the content of double bonds in moles per 1 mole of poly-8-Lys polymer is: 0.92× 0.87×0.92×2 (taking into account 2 double bonds moieties attached per each COOH group)=1.47.

Figure 5:
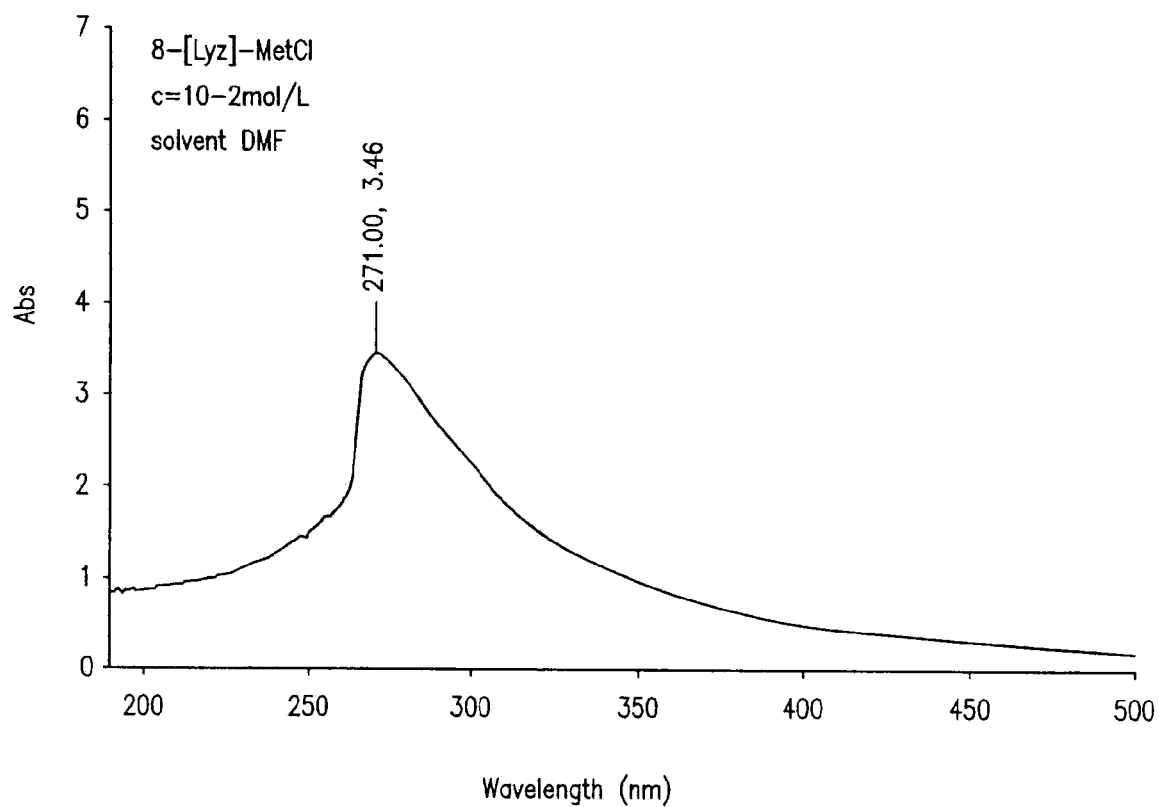
FIG. 5 is a trace of the UV spectra in DMF of polymeric photo cross-linker, poly-8-Lys-DEA/MA, $C=10^{-2}$ mol/L.
Figure 6:
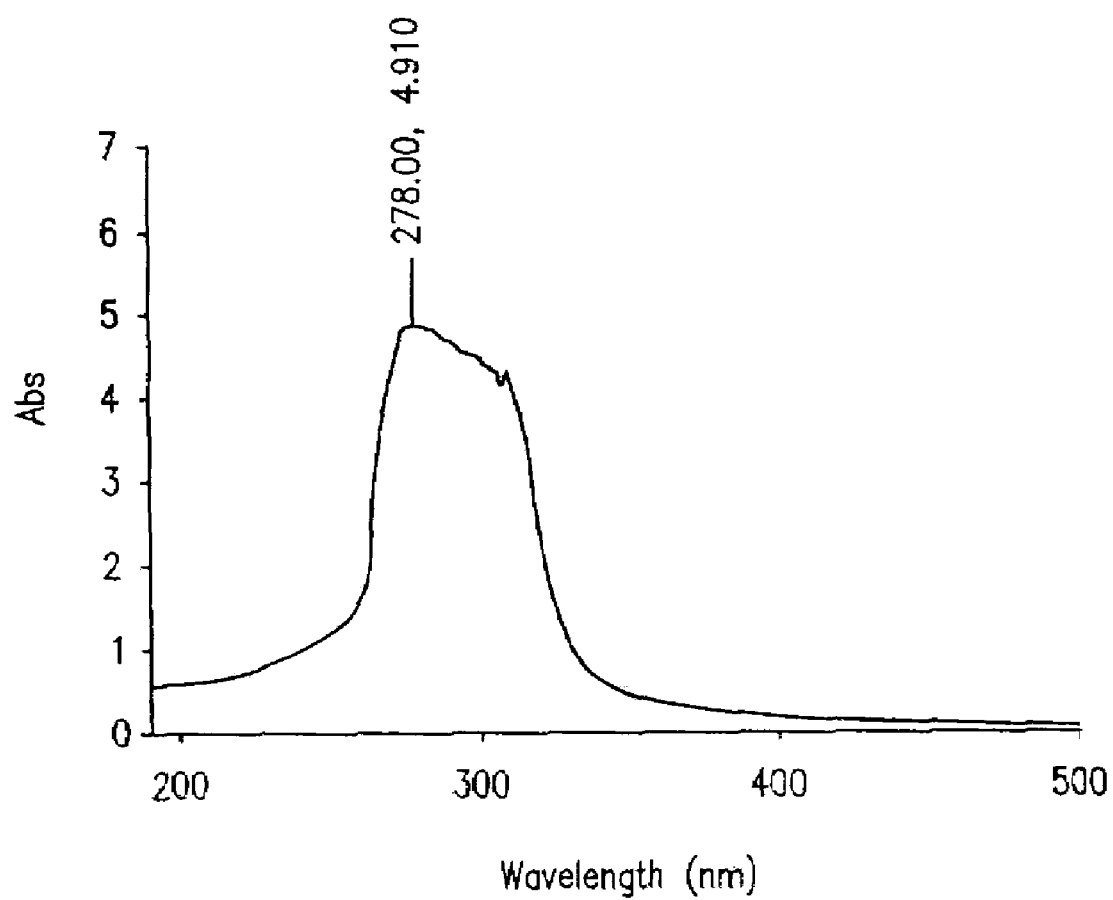
FIG. 6 is a trace of the UV-spectra in DMF of polymeric photo cross-linker poly-8-Lys-DEA/CA, $C=10^{-2}$ mol/L.

UV-spectra of polymeric photo cross-linkers poly-8-Lys-DEA/MA and poly-8-Lys-DEA/CA, in contrast to those for poly-8-Lys and poly-8-Lys-DEA, show new absorption maxima in the UV absorbance region (FIGS. 5 and 6). In the UV spectrum of 8-Lys-DEA/MA (FIG. 5), the absorption maximum is attributed to the double bond of methacrylic acid residue. By contrast, in the UV spectrum of 8-Lys-DEA/CA (FIG. 6), adsorption of the double bond is overlapped with absorption of the phenyl radical of cinnamic acid.

Example 9

Polyamide Type Poly-Functional Cross-Linkers (EAC-PA) with Pending Epoxy Groups

This example describes a multi-step synthesis conducted according to Scheme 4 herein. Poly-N,N'-sebacoyl-L-lysine, (8-Lyz(H)) first was transformed into the corresponding poly-alcohol poly(2-oxyethylamide) of 8-Lys(H) by interaction with monoethanol amine, using carbonyldiimidazole as a condensing agent in a manner analogous to that described in Example 8 for di-ethanolamine (Scheme 6). The hydroxyl number for polyol (calcd—4.31; found—4.03) corresponds to 93.5 mol % of transformation by amidation. Afterwards, acylation was carried out in solvent N,N-dimethylacetamide without using a tertiary amine since the polymers obtained in the presence of triethylamine were insoluble in organic solvents (undesirable crosslinking occurred).

The Bromine number: Acrylic acid derivative (Scheme 6, EAC-PA. wherein R$^7$=CH=CH) addition of bromine to double bonds: calcd—32.82; found—29.94), which corresponds to a transformation degree of 91.2 mol. %, and double bond content in macro-chains of 76.7 mol. %. Cinnamic acid derivative (R$^7$=CH=CH—C$_6$H$_5$) showed transformation of the lateral double bonds (calcd—27.74; found—27.50), which corresponds to a transformation of 99.1 mol. %, and double bond content in macro-chains of 83.4 mol. %).

Figure 7:
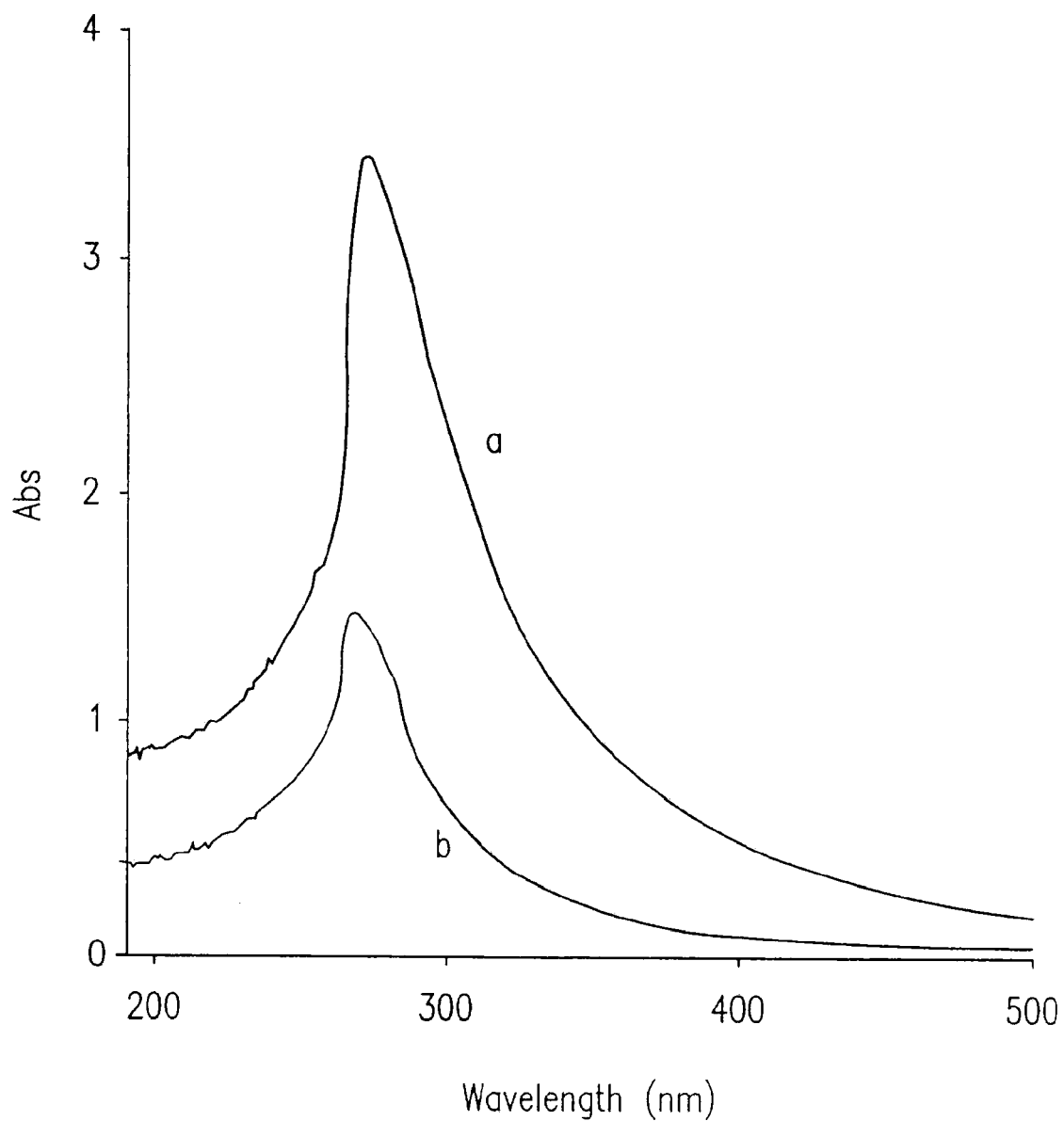
FIG. 7 is a trace of the UV-spectra in DMF of (a) polyamide (PA) type poly-functional cross linker with acrylic residue in lateral groups; and (b) the same polymer after epoxidation of lateral double bonds.

Catalytic epoxidation of the lateral double bonds was carried out in DMA using H$_2$O$_2$ as an oxidizing agent and Na$_2$WO$_4$ as a catalyst. The degree of transformation was determined using UV spectrometry based on the fact that compounds with double bonds, in contrast to epoxidized derivatives, absorb in the UV region of the spectra. The degree of epoxidation for the methyl derivative of acrylic acid corresponded to about 60% (as determined by UV-spectrophotometry, FIG. 7).

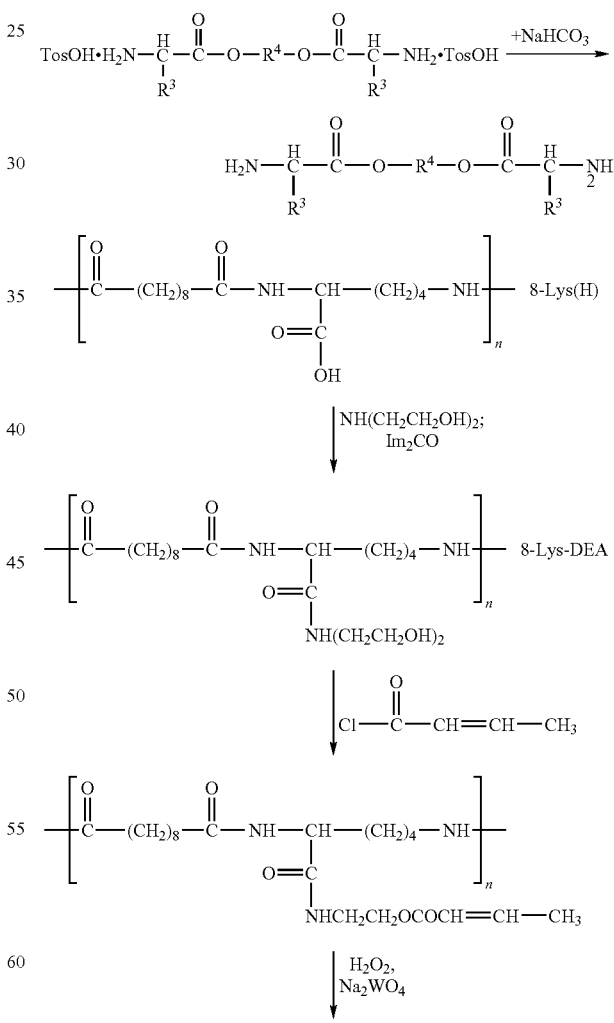

Scheme 6

-continued

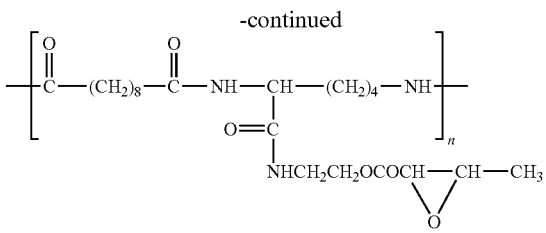

Example 10

Synthesized Cross-Linker Photo-Chemical Activity Test

Fifteen di-functional (EAC-2) and six tetra-functional (EAC-4) ester amide type cross-linking agents were selected to study photo-chemical transformations (from Tables 6 and 7). The selected 21 ester-amide type cross-linking agents were purified by triple re-crystallization (for crystalline products) or by triple re-precipitation from ethanol solution into distilled water (for non-crystallizable viscous liquids). All products were dried in vacuum at 50° C. and stored in a desiccator under reduced pressure.

Photo-transformation of the selected cross-linking agents was carried out as follows: 0.1 g of each compound was dissolved in chloroform and the obtained solution poured into small Teflon® dishes of 2 cm diameter. Chloroform was evaporated up to dryness and Teflon dishes with cross-linking agents (powder in case of crystalline compounds and sticky films in case of non-crystallizable compounds) were placed in vacuum oven and dried for 3 hours. Then the contents of the Teflon® dishes were subjected to UV-irradiation in the presence of atmospheric oxygen for 5, 10, 15, or 30 min (Further in photocuring examples unless otherwise stated metal halide UV-lamp 400 W with radiation flux 72 W employed; distance to the sample 20 cm. Samples were cooled using a fan, so that temperature was not exceeded 40° C.). After irradiation, a small part of cross-linking agent was taken from the Teflon® dish and checked for solubility in chloroform. The compounds that underwent photo-crosslinking lost solubility in chloroform.

Analogous experiments were conducted in presence of 5% w/w photo-initiators. Three widely used radical photoinitiators—di-phenyl(2,4,6-trimethylbenzoyl)-phosphine oxide (Darocur® TPO), 2-hydroxy-2-methyl-1-phenyl-1-propanol (Darocur® 1173), or 2,2-dimethoxy-2-phenylacetophenone (DMPA)—were added to the cross-agents and the mixture was subjected to UV exposure.

From the obtained results summarized in Tables 8 and 9, the following conclusions could be made:

1. the cross-linking agents derived from acrylic and methacrylic acids undergo fast curing;
2. derivatives of cinnamic and maleic acids, which undergo polymerization via 2+2 cycloaddition, showed much slower photo-transformation;
3. tetra-functional cross-linkers are by far more active than bi-functional analogs;
4. the majority of crosslinking-agents (both di- and tetra-functional) underwent photo-transformation and formed gel within 5-10 minutes without the presence of photo-initiators.

TABLE 8

Photo-transformation of di-functional EAC-2 cross-linkers without initiator

| # | Compound EAC-2 Formula (XIII)[1] $R^3$—$R^4$—$R^7$ | Exposure time[2] [min] | | | |
|---|---|---|---|---|---|
| | | 5 | 10 | 15 | 30 |
| 1 | Leu-6-CA | − | − | − | + |
| 2 | Leu-6-MA | + | | | |
| 3 | Leu-6-AA | + | | | |
| 4 | Leu-6-MLA | − | + | | |
| 5 | Leu-4-CA | + | | | |
| 6 | Leu-4-MA | + | | | |
| 7 | Leu-4-AA | + | | | |
| 8 | Phe-6-CA | − | + | | |
| 9 | Phe-6-MA | + | | | |
| 10 | Phe-6-AA | + | | | |
| 11 | Phe-6-MLA | − | + | | |
| 12 | Phe-4-CA | − | + | | |
| 13 | Phe-4-MA | + | | | |
| 14 | Phe-4-AA | + | | | |
| 15 | Phe-4-MLA | + | | | |
| | Compound EAC-2 | | | | |

[1] Designations: 4 = 1,4-butanediol; 6 - 1,6-hexanediol; AA = acryloyl; MA = methacryloyl; CA = cinnamoyl, MLA—maleic acid; (+) = becomes insoluble (crosslinked); (−) = did not crosslink (soluble in chloroform).
[2] 400 W metal halide lamp; distance to the sample 20 cm.

TABLE 9

Photo-transformations of tetra-functional EAC-4 cross-linkers of Formula (XV) without photo initiator

| # | Compound EAS-4[1] $R^3$—$R^7$ | Exposure Time[2] [5 min] |
|---|---|---|
| 1 | Leu-CA | + |
| 2 | Leu-MA | + |
| 3 | Leu-AA | + |
| 4 | Phe-CA | + |
| 5 | Phe-MA | + |
| 6 | Phe-AA | + |

[1] Designations: 3 = 1,3-propanediol; 4 = 1,4-butanediol; 6 = 1,6-hexanediol; PER = pentaerythritol; AA = acryloyl; MA = methacryloyl; CA = cinnamoyl; (+) = becomes insoluble (crosslinked).
[2] 400 W metal halide lamp; distance to the sample 20 cm.

Example 11

This Example illustrates the uses of invention cross-linking agents. Methods: Tensile strength measurements described herein were obtained using dumbbell-shaped PEU films (4×1.6 cm), which were cast from chloroform solution with average thickness of 0.125 mm and subjected to tensile testing on tensile strength machine (Chatillon TDC200) integrated with a PC using Nexygen FM software (Amtek, Largo, Fla.) or on Multitest 1-I (Mecmesin Ltd, UK) at a crosshead speed of 60 mm/min.

The average molecular weights and polydispersities herein were determined by gel permeation chromatography (GPC) using polystyrene standards. More particularly, number and weight average molecular weights ($M_n$ and $M_w$) are determined, for example, using a Model 510 gel permeation chromatography (Water Associates, Inc., Milford, Mass.) equipped with a high-pressure liquid chromatographic pump, a Waters 486 UV detector and a Waters 2410 differential refractive index detector. Solution of 0.1% LiCl in N,N-dimethylformamide (DMF) or N,N-dimethylacetamide (DMAc) was used as the eluent (1.0 mL/min). Polystyrene (PS) or poly(methyl methacrylate) (PMMA) standards having a narrow molecular weight distribution were used for calibrations.

Polymer glass transition (Tg) and melting temperatures (Tm) were determined using any means known in the art, for example by differential scanning calorimetry (DSC), for example, using a Mettler Toledo DSC 822e (Mettler Toledo Inc. Columbus, Ohio) differential scanning calorimeter. For measurement, the samples disclosed herein were placed in aluminum pans. Measurements were carried out at a scanning rate of 10° C./min under nitrogen flow.

Semi-Interpenetrating Networks

For semi-IPN experiments, the linear matrix polymer PEA 4-Phe-4 of general Formula (I) wherein $R^1=(CH_2)_4$; $R^3=CH_2C_6H_5$; $R^4=(CH_2)_4$, was synthesized; Mw=65,500 Da; Mw/Mn=1.80; GPC in DMF, PMMA).

At the first stage, this Example addresses the question of whether invention cross-linking agents can be used as plasticizers without causing the composition to undesirably adhere to the surface of other materials (for example, steel, and other medical device surfaces). For this purpose, composition films were cast in chloroform using predetermined ratios of the poly(4-Phe-4) to invention cross-linker (see Table 10) and plasticizing effect was determined.

Dried films were folded, squeezed together with a double paper clip and immersed in water for 24 hours. Then the samples were removed from water, double-clips were removed, and the "self-adherence" was studied visually. The results of this study summarized in Table 10 herein show that di-functional cross-linkers based on methacrylic, maleic and especially cinnamic acids are most likely to provide optimum results as plasticizers because non-cross-linked films containing these cross-linkers did not become sticky after soaking in water for 24 hours.

Mechanical properties of polymer PEA 4-Phe-4 in the absence of cross-linker were compared with those of the most commonly used synthetic biomedical co-polymer, poly(lactic-co-glycolic) acid, PLLA (Boehringer Ingelheim) in the absence of cross-linker. The mechanical properties of films prepared as described above, but using PEA 4-Phe-4 (Mw=73,000) and polyester PLLA (Mw=100,000) are rather similar (Table 11 herein).

TABLE 11

Mechanical properties of polymers and semi-IPNs:

| Polymer Film[1], or composition | Tensile strength [σ, MPa] | Elongation at break [ε, %] | Young's modulus [GPa] |
|---|---|---|---|
| PEA 4-Phe-4 | 30 | 36 | 1.6 |
| PLLA, 100 KDa | 39 | 10.5 | 2.4 |
| PEA 4-Phe-4 with 30% w/w EAC-2[2] | 6.5 | 144 | 0.8 |
| PEA 4-Phe-4 with 30% w/w EAC-2[2] after exposure[3] | 18 | 93 | 0.9 |

[1]PEA of formula (I), wherein $R^1 = (CH_2)_4$; $R^3 = CH_2C_6H_5$; $R^4 = (CH_2)_4$.
[2]Phe-6-MA was applied as EAC-2 (dimethacrylate of bis(L-Phe)-1,6-hexanediol diester).
[3]Film was exposed for 5 min; 400 W metal halide lamp; distance to the sample 20 cm.

In another experiment, film of PEA 4-Phe4 containing 80/20 w/w cross-linking agent Leu-6-MA (of general Formula EAC-2 where n=6, $R^5=C(CH_3)=CH_2$) was cast (as described above) and tensile properties tested prior to and after UV-exposure for cross-linking. As shown in Table 11 the

TABLE 10

Properties of the mixtures of PEA 4-Phe-4 with di-functional cross-linkers EAC-2[1]

| | PEA 4-Phe-4/EAC-2 [w/w] | | | | | | | | |
|---|---|---|---|---|---|---|---|---|---|
| | 80/20 | | | 60/40 | | | 40/60 | | |
| EAC-2 [$R^3$—$R^4$—$R^7$] | Dry | Wet[2] | Self-adherence[3] | Dry | Wet[2] | Self-adherence | Dry | Wet[2] | Self-adherence |
| Leu-6-AA | Hard | Elastic, Not sticky | — | Wax-like | Brittle | — | Wax-like, sticky | Wax-like | — |
| Leu-6-MA | Hard, Brittle | Hard, Brittle | — | Hard, Brittle | Wax-like, Brittle | — | Elastic, sticky | Wax-like brittle | — |
| Leu-6-CA | Elastic, Not sticky | Elastic, without change | — | Elastic | Elastic, without change | — | Very elastic, Not sticky | Very elastic, Not sticky | — |
| Leu-6-MLA | Hard | Elastic | — | Elastic | Very elastic | — | Very elastic, sticky | Very elastic, sticky | — |
| Phe-6-MA | Hard | Slightly elastic | — | Hard | Elastic | — | Elastic, Not sticky | Very elastic, Not sticky | — |
| Phe-6-CA | Hard | Slightly elastic | — | Brittle | Elastic | — | Brittle | Elastic, Brittle | — |
| Phe-6-MLA | Slightly elastic | Elastic | — | Elastic, Not sticky | Elastic | — | Very elastic, Not sticky | Elastic, Brittle | — |

[1]EAC-2 of general Formula (XIII); $R^4$: 6 = 1,6-hexanediol; $R^7$: AA = acryloyl, MA = methacryloyl, CA = cinnamoyl, MLA = maleic acid.
[2]Samples were pre-soaked in water at room temperature for 24 hours.
[3](—) means: no self-adherence observed.

tensile strength (σ) of the PEA 4-Phe-4 film after mixing with cross-linking agent (but before cross-linking) decreased about 5-fold and elongation at break increased 4-fold, i.e. polymer films became more elastic (ductile) in the presence of the cross-linker, but before photo-irradiation.

After exposure to UV irradiation for 5 min., the tensile strength of the mixture increased about 3-fold and elongation at break (ε) decreased about 2-fold, but the Young's modulus virtually did not change. In other words, the film was somewhat strengthened after irradiation; however, the properties measured were still lower than for PEA 4-Phe4 alone.

Example 13

This example shows that elasticity of polymer can be improved using a crosslinking technique analogous to that used in preparation of vulcanized rubber, where a three-dimensional network of random coils is formed. Such a strategy to achieve tough and elastomeric materials is also found in nature. For example, collagen and elastin, the major fibrous protein components of extracellular matrix, are both cross-linked to achieve elasticity (Voet D. & Voet J. G. *Biochemistry* (John Wiley & Sons, New York, 1995). A biodegradable PEA polymer with unsaturated double bonds in the backbone, which had been cross-linked with photo-reactive biodegradable cross-linking agents ESC or EAC was selected for use in this experiment. An exemplary fumaric acid based unsaturated co-PEA of the following architecture PEA 75/25 Seb/Fum-Leu-6 was prepared by a method similar to that described elsewhere (Guo K. et al., *J. Polym. Sci. Part A: Polym. Chem.*, (2005), 43, 1463-1477).

the tensile strength and Young's modulus increased and elasticity decreased substantially as a result of formation of a solid polymer network.

TABLE 12

Mechanical properties of the unsaturated co-polymers and its networks

| Composition of Polymer Film | Tensile strength [σ, MPa] | Elongation at break [ε, %] | Young's modulus [E, GPa] |
|---|---|---|---|
| PEA Seb/Fum 75/25 | 20 | 141 | 1.8 |
| PEA Seb/Fum 75/25 after exposure[2] | 50.5 | 2.6 | 2.7 |
| PEA 4-Phe-4 with 30% w/w ESC-2[3] | 9 | 323 | 0.13 |
| PEA 4-Phe-4 with 30% w/w ESC-2[3] after exposure[2] | 16 | 142 | 0.53 |

[1]PEA of formula (I), wherein $R^1$ = 75/25 $(CH_2)_8$/CH=CH; $R^3$ = $CH_2C_6H_5$; $R^4$ = $(CH_2)_4$.
[2]Film was exposed for 5 min; metal halide 400 W; distance to the sample 20 cm.
[3]Phe-6-MA was applied as ESC-2 (dimethacrylate of bis(L-Phe)-1,6-hexanediol diester).

In the next experiment, a film of unsaturated co-PEA containing 30% w/w of cross-agent Phe-6-MA (structure shown below) was prepared and the tensile properties were examined:

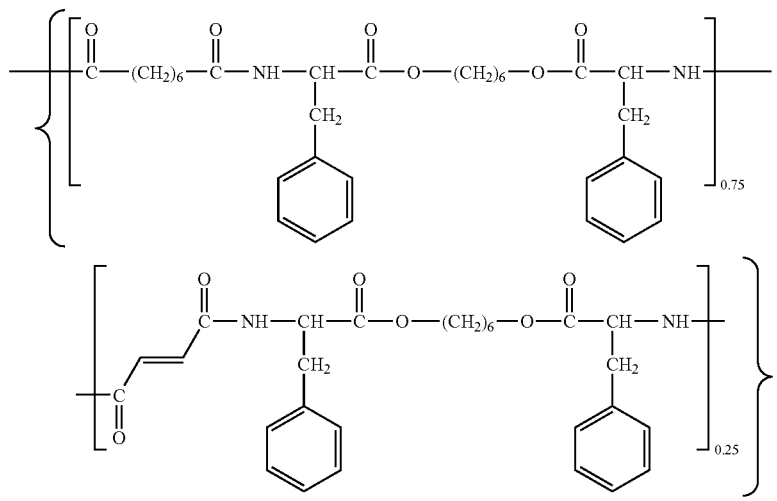

PEA 75/25 Seb/Fum-Leu-6 wherein 75/25 is the mole ratio of sebacic to fumaric acid in the copolymer of formula (I); and wherein $R^3$=$CH_2C_6H_5$; and $R^4$=$(CH_2)_6$.

Tensile properties of a film of pure (i.e. without cross-linker) PEA 75/25 (Seb/Fum)-Leu-6 were determined as shown in Table 12. Then a sample of the same polymer film was exposed to irradiation for 5 min. by light from a broad-band UV lamp. As shown by the data summarized in Table 12 herein, even in the absence of photoinitiator, the irradiated polymer showed desirable changes in mechanical properties:

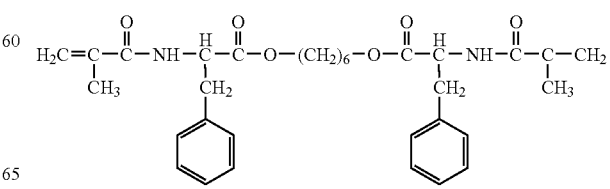

Phe-6-MA

As shown by the data summarized in Table 12, addition of cross-linking agent Phe-6-MA to the PEA 8/FA-75/25-Phe-6 substantially decreased tensile strength and Young's modulus, but increased elasticity. UV irradiation slightly improved mechanical the mechanical properties, which are far from those of the pure PEA 8/FA-75/25-Phe-6 polymer film.

Example 14

In previous examples invention di-functional cross-linking agents were tested. For purposes of comparison, in this example a commercially available cross-linker, pentaerythritol tetra-acrylate, was examined as a model cross-linker for forming a polymer network with PEA of 75/25 Seb/Fum-Leu-6 (formula below) with molecular weight Mw=56000 Da, polydispersity 1.73, and Tg=19.7° C.

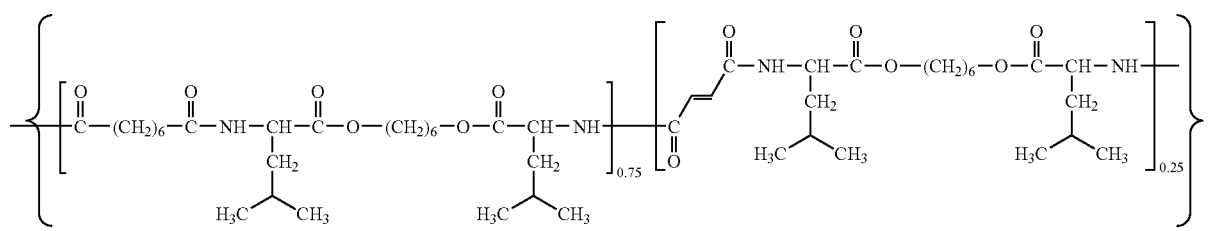

PEA of 75/25 Seb/Fum-Leu-6 Blend

The polymer blend containing 4% w/w of DAROCUR® TPO as photo-initiator and 1 to 5% w/w cross-linker (Table 13) was cast onto a hydrophobic surface. Sample films of about. 0.13 mm thickness mounted 4 cm away from the light source were exposed to a broadband UV (100 W mercury vapor arc) lamp with an exposure intensity of 10000 mW/cm² at light guide end and irradiation time of 5 min. The reaction model is shown in Scheme 7 below:

Scheme 7

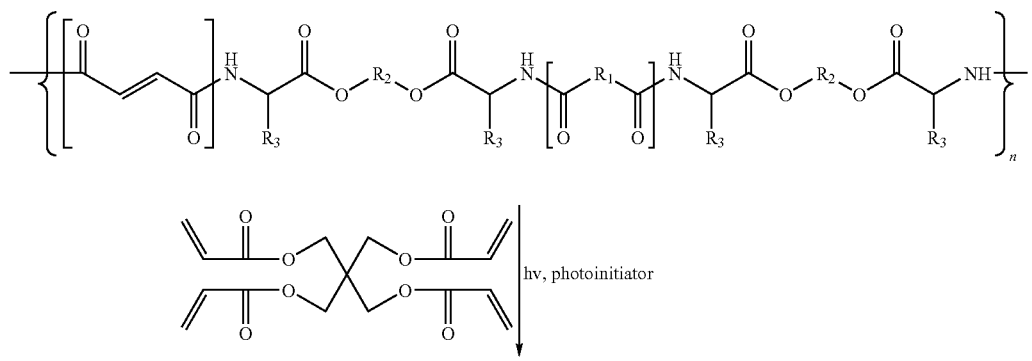

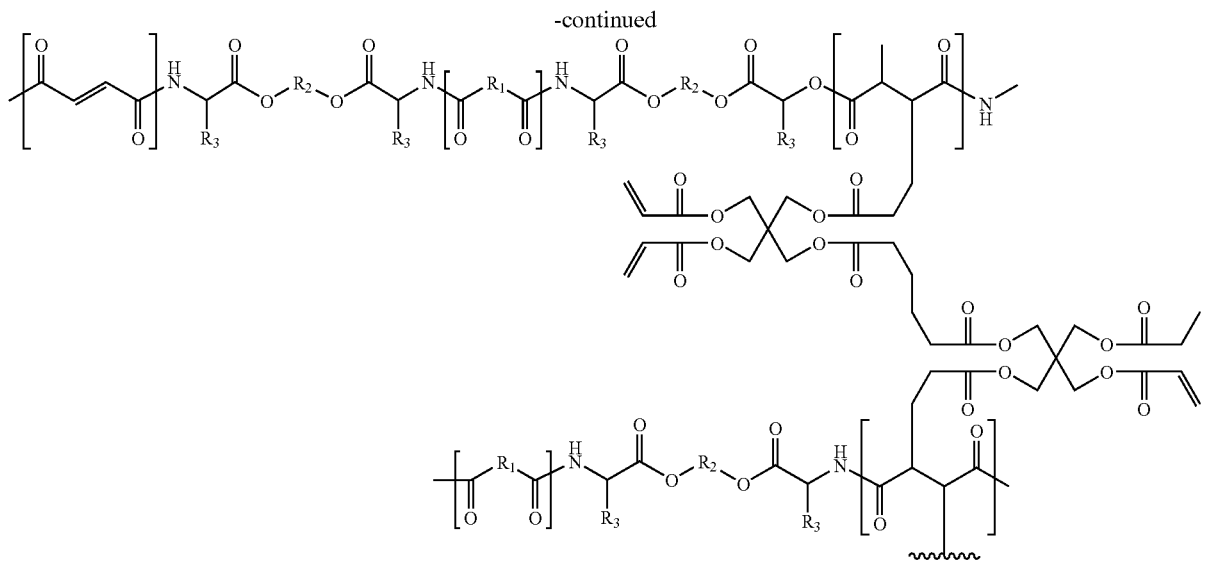

Mechanical properties of the polymer were tested prior to and after UV irradiation and the results are summarized in Table 13 below.

TABLE 13

Mechanical properties of the unsaturated co-polymer PEA[1]/ pentaerythritol tetraacrylate blends containing 4% w/w commercial photo-initiator[2] prior to and after UV exposure

| PEA[1] Polymer Film, | Tensile strength at break [σ, MPa] | Elongation at break [ε, %] | Young's modulus [E, MPa] |
|---|---|---|---|
| PEA with 1% ESC-4; | 8.1, | 322, | 98.7, |
| After exposure | 9.7 | 300 | 80 |
| PEA with 2% ESC-4; | 5.8 | 386 | 17.3 |
| After exposure | 8.2 | 362 | 71.5 |
| PEA with 4% ESC-4, | 1.6 | 582 | 2.3 |
| After exposure | 4.5 | 297 | 59 |
| PEA with 5% ESC-4, | 5.9 | 415 | 20 |
| after exposure | 21.7 | 266 | 468.3 |

[1] PEA employed was Seb/Fum 75/25-Leu-6 was employed.
[2] Diphenyl(2,4,6-trimethylbenzoyl)-phosphine oxide (Darocur TPO ™).
[3] Film was exposed for 5 min; UV 10 000 mW/cm²; distance from source 4 cm.

Figure 8:
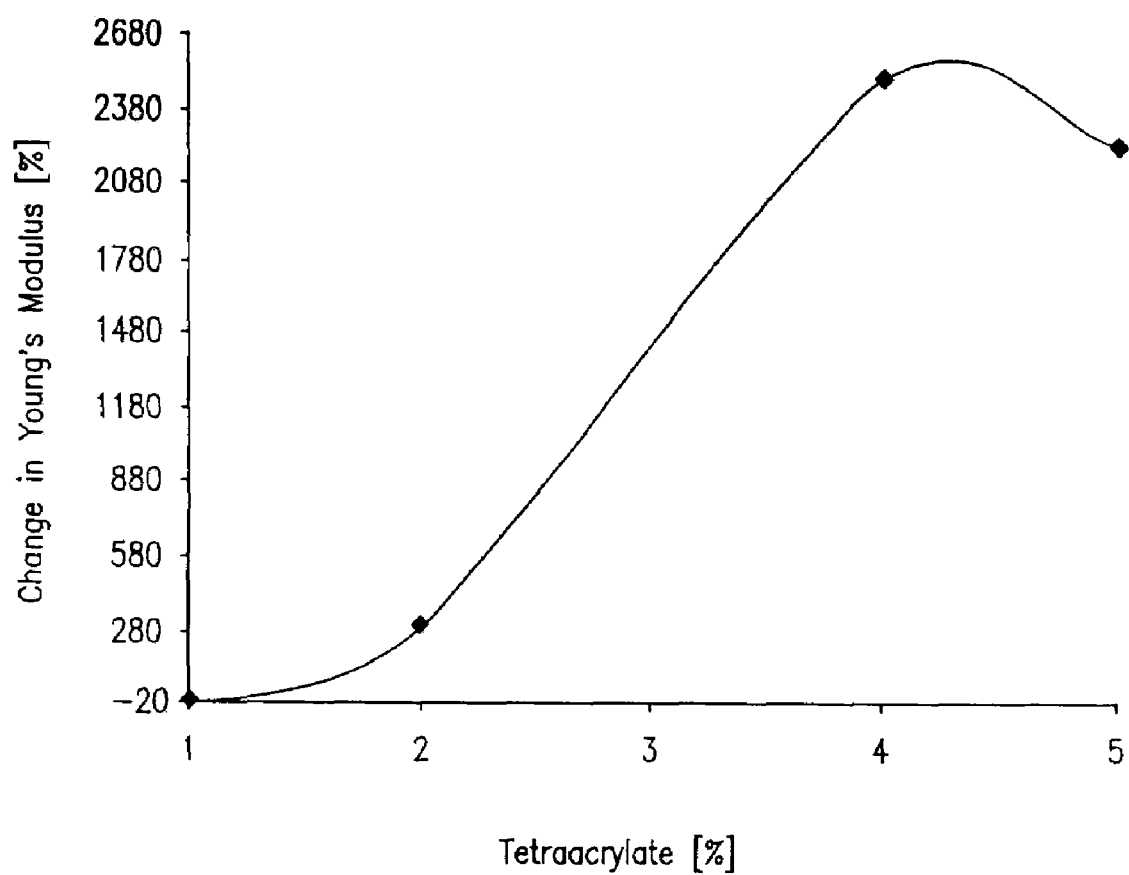
FIG. 8 is a graph showing change in Young's modulus after photocrosslinking of unsaturated polymer UPEA.

Young's modulus of irradiated UPEA increased over 2500% as tetraacrylate content reached 4% w/w (FIG. 8). This result indicates that UPEAs display obvious reactivity and the potential to fabricate into solid scaffolds with a wide range of applications.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention is limited only by the following claims.

What is claimed is:

1. A composition comprising:
   a biodegradable linear polymer comprising at least one of the following:
   a poly(ester amide) (PEA) having a chemical formula described by general structural formula (I):

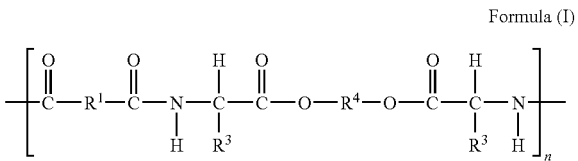

Formula (I)

wherein, n is about 10 to about 150; each $R^1$ is independently selected from the group consisting of $(C_2-C_{20})$ alkylene, $(C_2-C_{20})$ alkenylene, $(C_2-C_{12})$ epoxy-alkylene, residues of α,ω-bis(o,m, or p-carboxy phenoxy)-$(C_1-C_8)$ alkane, 3,3'-(alkenedioyldioxy) dicinnamic acid, 4,4'-(alkanedioyldioxy) dicinnamic acid, and combinations thereof; the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl, and $(CH_2)_2SCH_3$; and $R^4$ in each n monomer is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of general formula (II), and combinations thereof;

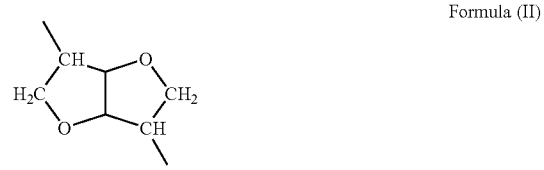

Formula (II)

a PEA having a chemical structure described by general structural formula (III),

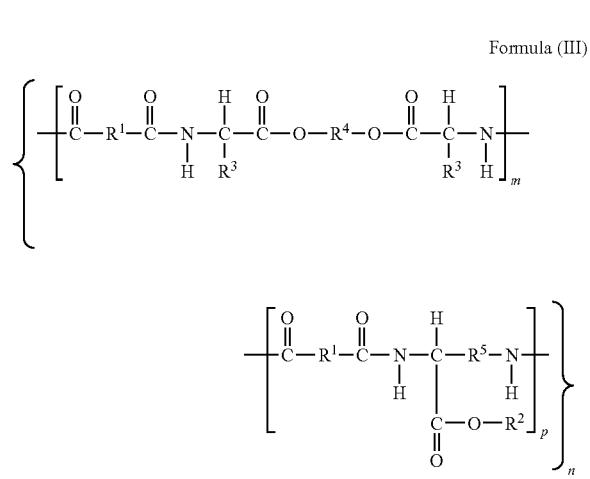

Formula (III)

wherein m is about 0.1 to about 0.9; p is about 0.9 to about 0.1, n is about 10 to about 150, each $R^1$ is independently selected from the group consisting of ($C_2$-$C_{20}$) alkylene, ($C_2$-$C_{20}$) alkenylene, ($C_2$-$C_{12}$) epoxy-alkylene, residues of α,ω-bis(o, m, or p-carboxy phenoxy)-($C_1$-$C_8$) alkane, 3,3'-(alkenedioyldioxy) dicinnamic acid, 4,4'-(alkanedioyldioxy) dicinnamic acid, and combinations thereof; $R^2$ is independently selected from the group consisting of hydrogen, ($C_6$-$C_{10}$) aryl ($C_1$-$C_6$) alkyl and a protecting group; each $R^3$ is independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl and $(CH_2)_2SCH_3$; and each $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of general formula II, and combinations thereof; and $R^5$ is independently ($C_2$-$C_{20}$) alkyl or ($C_2$-$C_{20}$) alkenyl;

a poly(ester urethane) (PEUR) having a chemical formula described by structural formula (IV),

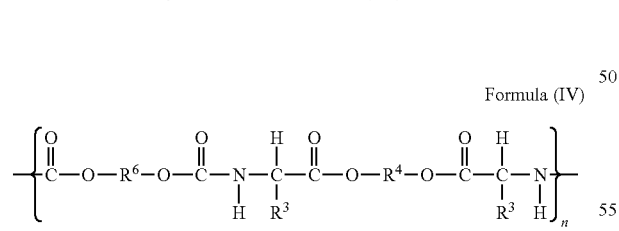

Formula (IV)

wherein n ranges from about 5 to about 150; wherein the $R^3$s in an individual n monomer are independently selected from the group consisting of hydrogen, ($C_1$-$C_6$) alkyl, ($C_2$-$C_6$) alkenyl, ($C_6$-$C_{10}$) aryl($C_1$-$C_6$) alkyl and $(CH_2)_2SCH_3$; $R^4$ and $R^6$ is selected from the group consisting of ($C_2$-$C_{20}$) alkylene, ($C_2$-$C_{20}$) alkenylene, $C_2$-$C_8$) alkyloxy ($C_2$-$C_{20}$) alkylene, bicyclic-fragments of 1,4:3,6-dianhydrohexitols of structural formula (II), and combinations thereof;

a PEUR having a chemical structure described by general structural formula (V),

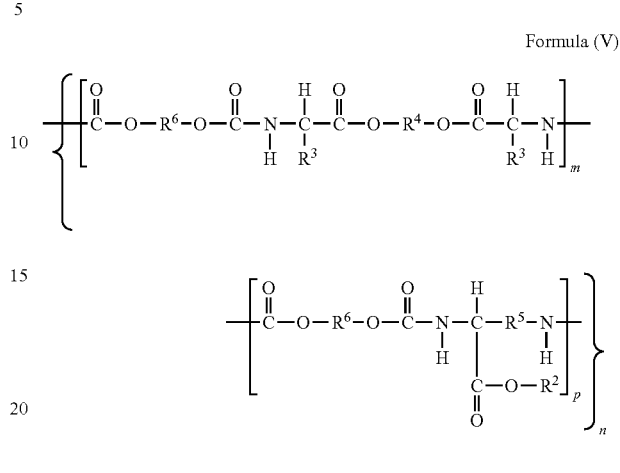

Formula (V)

wherein n ranges from about 5 to about 150, m ranges about 0.1 to about 0.9: p ranges from about 0.9 to about 0.1; $R^2$ is independently selected from the group consisting of hydrogen, ($C_1$-$C_{12}$) alkyl, ($C_2$-$C_8$) alkyloxy, ($C_2$-$C_{20}$) alkyl ($C_6$-$C_{10}$) aryl, and a protecting group; the $R^3$s within an individual m monomer are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl, and $(CH_2)_2SCH_3$; $R^4$ and $R^6$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), and combinations thereof, and $R^5$ is independently selected from the group consisting of ($C_1$-$C_{20}$) alkyl and ($C_2$-$C_{20}$) alkenyl;

a poly(ester urea) (PEU) having a chemical formula described by structural formula (VI),

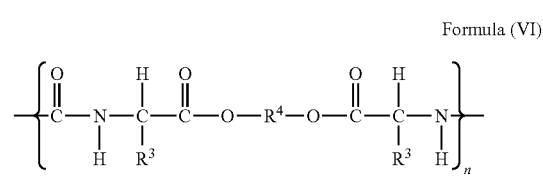

Formula (VI)

wherein n is about 10 to about 150; the $R^3$s within an individual n monomer are independently selected from the group consisting of hydrogen, ($C_1$-$C_6$) alkyl, ($C_2$-$C_6$) alkenyl, ($C_6$-$C_{10}$) aryl ($C_1$-$C_6$) alkyl, and $(CH_2)_2SCH_3$; $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of a 1,4:3,6-dianhydrohexitol of structural formula (II) and combinations thereof;

and a PEU having a chemical formula described by structural formula (VII),

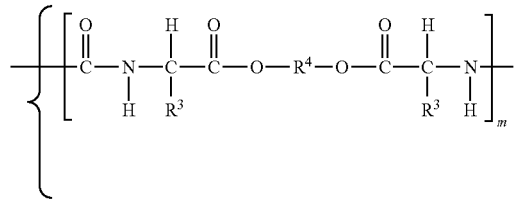

Formula (VII)

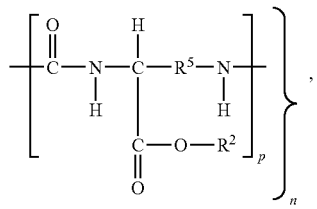

wherein m is about 0.1 to about 1.0; p is about 0.9 to about 0.1; n is about 10 to about 150; each $R^2$ is independently hydrogen, $(C_1-C_{12})$ alkyl, $(C_2-C_8)$ alkyloxy $(C_2-C_{20})$ alkyl, $(C_6-C_{10})$ aryl or a protecting group; and the $R^3$s within an individual m monomer are independently selected from hydrogen, $(C_1-C_6)$ alkyl, $(C_2-C_6)$ alkenyl, $(C_6-C_{10})$ aryl $(C_1-C_6)$ alkyl and $(CH_2)_2SCH_3$; $R^4$ is independently selected from $(C_2-C_{20})$ alkylene, $(C_2-C_{20})$ alkenylene, $(C_2-C_8)$ alkyloxy $(C_2-C_{20})$ alkylene; bicyclic-fragments of a 1,4:3,6-dianhydrohexitol of structural formula (II), and combinations thereof, and $R^5$ is independently selected from the group consisting of $(C_1-C_{20})$ alkyl and $(C_2-C_{20})$ alkenyl;

and at least one di- or poly-functional cross-linker that polymerizes upon exposure to a free radical and contains at least one hydrolyzable functional group, wherein the composition forms a semi-interpenetrating polymer network following exposure to active species.

2. The composition of claim 1, wherein the cross-linker is an ester-amide having a chemical structure described by general structural formula (XIII) below:

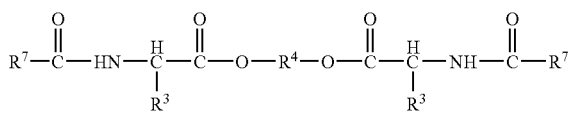

Formula (XIII)

wherein, the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, bicyclic-fragments of 1,4:3,6-dianhydrohexitols of general formula (II), and combinations thereof; and $R^7$ is independently selected from the group consisting of —CH=CH$_2$, —C(CH$_3$)=CH$_2$, —CH=CH—(C$_6$H$_5$), and —CH=CH—COOH.

3. The composition of claim 1, wherein the cross-linker is an ester-amide with a chemical structure described by general structural formula (XIV):

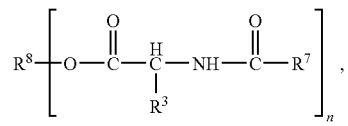

Formula (XIV)

wherein the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; $R^7$ is selected from the group consisting of —CH=CH$_2$, —C(CH$_3$)=CH$_2$, —CH=CH—(C$_6$H$_5$), and —CH=CH—COOH; $R^8$ is selected from branched $(C_2-C_{12})$ alkylene or branched $(C_2-C_8)$ alkyloxy $(C_2-C_{20})$ alkylene, and n is 3, 4, 5 or 6.

4. The composition of claim 3, wherein $R^8$ is selected from the group consisting of —CH(CH$_2$—)$_2$; CH$_3$—CH$_2$—C(CH$_2$—)$_3$; C(CH$_2$—)$_4$, and (—CH$_2$)$_3$C—CH$_2$—O—CH$_2$—C(CH$_2$—)$_3$.

5. The composition of claim 1, wherein the cross-linker is a tetra-functional ester amide cross-linker (EAC-4) with a chemical structure described by general structural formula (XV):

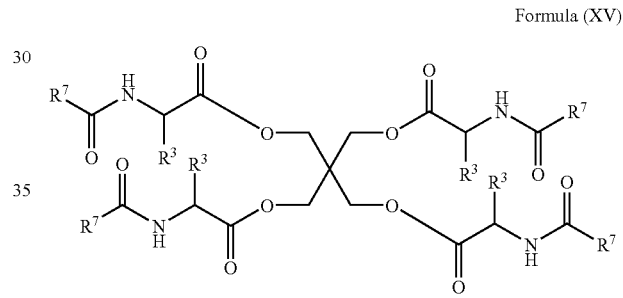

Formula (XV)

wherein, the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; and $R^7$ is selected from the group consisting of —CH=CH$_2$, —C(CH$_3$)=CH$_2$, —CH=CH—(C$_6$H$_5$), and —CH=CH—COOH.

6. The composition of claim 1, wherein the cross-linker is a polyamide type cross-linker (EAC-PA) having a chemical formula described by general structural formula (XVI)

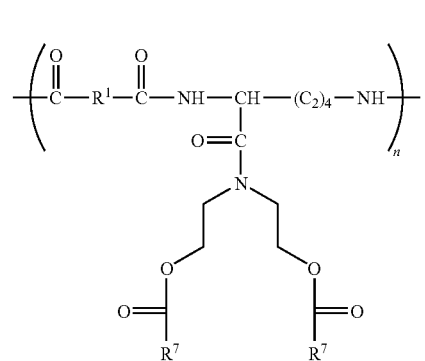

Formula (XVI)

wherein n is about 10 to about 150; $R^1$ is independently $(C_2-C_{20})$ alkylene, $(C_2-C_{20})$ alkenylene, residues of α,ω-bis (o,m, or p-carboxy phenoxy)-$(C_1-C_8)$ alkane, 3,3'-(alkenedioyldioxy)dicinnamic acid, 4,4'-(alkanedioyldioxy)dicinnamic acid, or a combination thereof; and $R^7$ is selected from the group consisting of —CH=CH$_2$, —C(CH$_3$)=CH$_2$, —CH=CH—(C$_6$H$_5$), and —CH=CH—COOH.

7. The composition of claim 1, wherein the cross-linker is a poly(ester amide) crosslinker (EAC-PEA) having a chemical formula described by general structural formula (XVII):

carboxyphenoxy) $(C_1-C_8)$ alkane, or a residue of 4,4'-(alkanedioyl dioxy)dicinnamic acid, or a combination thereof.

12. The composition of claim 1, wherein the polymer comprises a PEA, wherein $R^1$ is a residue α,ω-bis(4-carboxyphenoxy) $(C_1-C_8)$ alkane, such as 1,3-bis(4-carboxyphenoxy) propane (CPP), or 4,4'-(adipoyldioxy)dicinnamic acid, and $R^4$ is a bicyclic-fragment of a 1,4:3,6-dianhydrohexitol of general formula (II).

13. The composition of claim 1, wherein the cross-linker is cross-linked.

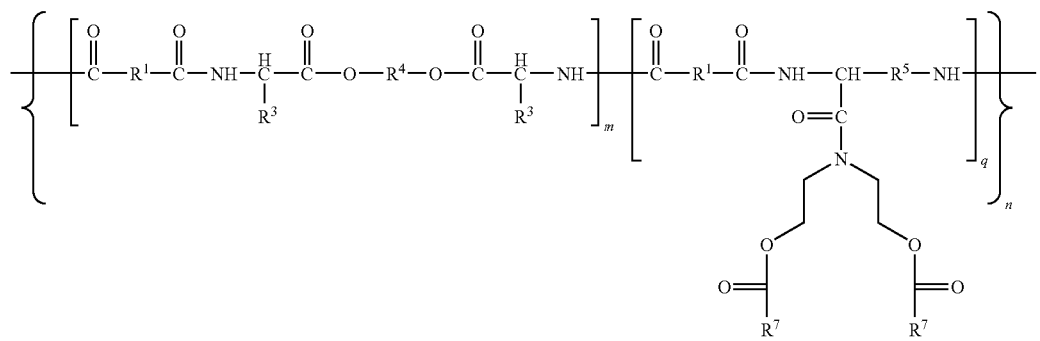

Formula (XVII)

m is about 0.1 to about 0.9; q is about 0.9 to about 0.1, n is about 10 to about 150, each $R^1$ is independently selected from the group consisting of $(C_2-C_{20})$ alkylene, $(C_2-C_{20})$ alkenylene, residues of α,ω-bis(o,m, or p-carboxy phenoxy)-$(C_1-C_8)$ alkane, 3,3'-(alkenedioyldioxy)dicinnamic acid, 4,4'-(alkanedioyldioxy)dicinnamic acid, and combinations thereof; the $R^3$s in an m monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; and $R^4$ is independently selected from the group consisting of $(C_2-C_{20})$ alkylene, $(C_2-C_{20})$ alkenylene, $(C_2-C_8)$ alkyloxy $(C_2-C_{20})$ alkylene, a bicyclic-fragment of 1,4:3,6-dianhydrohexitol of general formula II, and combinations thereof; $R^7$ is independently selected from the group consisting of —CH=CH$_2$, —C(CH$_3$)=CH$_2$, —CH—CH—(C$_6$—H$_5$), and —CH=CH—COOH; and $R^5$ is independently $(C_2-C_{20})$ alkyl or $(C_2-C_{20})$ alkenyl.

8. The composition of claim 1, wherein the composition is photo-activated by exposure to light having a wavelength in the range from about 400 nm to about 700 nm.

9. The composition of claim 1, wherein the cross-linker is cross-linked and the composition forms a semi-interpenetrating network.

10. The composition of claim 1, wherein the polymer comprises at least one double bond in the backbone and the composition forms a polymer network after exposure to photo-activation.

11. The composition of claim 1, wherein the polymer comprises a PEA, wherein the $R^1$ is either a residue of α,ω-bis(4-

14. The composition of claim 1, wherein the composition further comprises a bioactive agent dispersed in the polymer.

15. The composition of claim 1, wherein the composition is formed into a desired shape for implant.

16. A composition being a di- or poly-functional α-amino acid-containing ester-amide cross-linker with at least one hydrolyzable functional group, wherein the cross-linker polymerizes upon exposure to a free radical.

17. The composition of claim 16 having a chemical structure described by general structural formula (XIV):

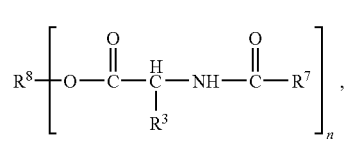

Formula (XIV)

wherein the $R^3$s in each n monomer are independently selected from the group consisting of hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl and $(CH_2)_2SCH_3$; $R^7$ is —CH=CH$_2$, —C(CH$_3$)=CH$_2$, —CH=CH—(C$_6$H$_5$), or —CH=CH—COOH; $R^8$ is selected from branched $(C_2-C_{12})$ alkylene, or branched $(C_2-C_8)$ alkyloxy $(C_2-C_{20})$ alkylene; and; and n is 3, 4, 5 or 6.

18. The composition of claim 16 having a chemical structure described by general structural formula (XV):

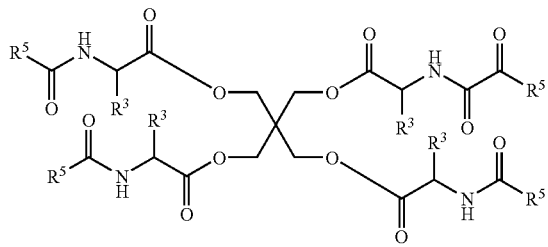

Formula (XV)

wherein, the $R^3$s in each n monomer are independently hydrogen, $(C_1-C_6)$ alkyl, $(C_2-C_6)$ alkenyl, $(C_2-C_6)$ alkynyl, $(C_6-C_{10})$ aryl $(C_1-C_6)$ alkyl or $(CH_2)_2SCH_3$; and $R^7$ is —CH=CH$_2$, —C(CH$_3$)=CH$_2$, —CH=CH—(C$_6$H$_5$), or —CH=CH—COOH, and wherein the composition polymerizes upon exposure to an active species.

19. A composition of claim 16 having a chemical formula described by general structural formula (XVI)

Formula (XVI)

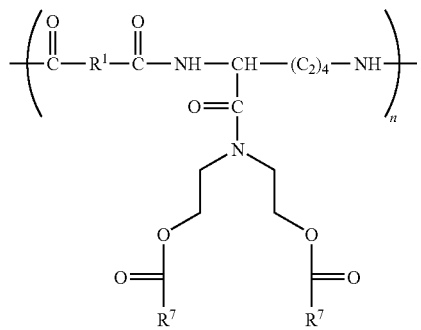

wherein n is about 10 to about 150; $R^1$ is independently selected from the group consisting of $(C_2-C_{20})$ alkylene, $(C_2-C_{20})$ alkenylene, a residue of α,ω-bis(o,m, or p-carboxy phenoxy)-$(C_1-C_8)$ alkane, 3,3'-(alkenedioyldioxy)dicinnamic acid, 4,4'-(alkanedioyldioxy)dicinnamic acid, and combinations thereof; and $R^7$ is selected from the group consisting of —CH=CH$_2$, —C(CH$_3$)=CH$_2$, —CH=CH—(C$_6$H$_5$), and —CH=CH—COOH.

20. The composition of claim 16 having a chemical formula described by general structural formula (XVII):

Formula (XVII)

m is about 0.1 to about 0.9; q is about 0.9 to about 0.1, n is about 10 to about 150; $R^1$ is independently selected from the group consisting of $(C_2-C_{20})$ alkylene, $(C_2-C_{20})$ alkenylene, a residue of α,ω-bis(o,m, or p-carboxy phenoxy)-$(C_1-C_8)$ alkane, 3,3'-(alkenedioyldioxy)dicinnamic acid, 4,4'-(alkanedioyldioxy)dicinnamic acid, and combinations thereof, the $R^3$s in an m monomer are independently selected from the group consisting of hydrogen, $(C_1-C_6)$ alkyl, $(C_2-C_6)$ alkenyl, $(C_2-C_6)$ alkynyl and $(C_6-C_{10})$ aryl $(C_1-C_6)$ alkyl and $(CH_2)_2SCH_3$; and $R^4$ is independently $(C_2-C_{20})$ alkylene, $(C_2-C_{20})$ alkenylene, $(C_2-C_8)$ alkyloxy $(C_2-C_{20})$ alkylene, a bicyclic-fragment of 1,4:3,6-dianhydrohexitol of general formula (II), and combinations thereof; $R^7$ is selected from the group consisting of —CH=CH$_2$, —C(CH$_3$)=CH$_2$, —CH—CH—(C$_6$—H$_5$), and —CH=CH—COOH; and $R^5$ is independently $(C_2-C_{20})$ alkyl or $(C_2-C_{20})$ alkenyl.

21. A method for creating a solid implant in a subject comprising:
   a) introducing into a subject a composition of claim 1 as a liquid; and
   b) exposing the composition to active species to create a solid implant in the subject.

22. The method of claim 21, wherein the composition is injected into a bone or tooth defect in the subject.

23. The method of claim 21, wherein, prior to the introducing, the method further comprises forming the composition into the shape of an internal fixation device prior to being exposed to the active species.

24. The method of claim 21, wherein the composition further comprises one or more diagnostic or therapeutic bioactive agents.

* * * * *